US011142751B2

(12) United States Patent
Wang et al.

(10) Patent No.: US 11,142,751 B2
(45) Date of Patent: Oct. 12, 2021

(54) **CRISPR-CAS SYSTEM FOR *CLOSTRIDIUM* GENOME ENGINEERING AND RECOMBINANT STRAINS PRODUCED THEREOF**

(71) Applicant: AUBURN UNIVERSITY, Auburn, AL (US)

(72) Inventors: Yi Wang, Auburn, AL (US); Jie Zhang, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 0 days.

(21) Appl. No.: 16/811,733

(22) Filed: Mar. 6, 2020

(65) Prior Publication Data

US 2020/0283746 A1 Sep. 10, 2020

Related U.S. Application Data

(60) Provisional application No. 62/815,198, filed on Mar. 7, 2019.

(51) Int. Cl.

| | |
|---|---|
| ***C12N 9/22*** | (2006.01) |
| ***C12N 15/63*** | (2006.01) |
| *C12N 1/20* | (2006.01) |
| *C12R 1/145* | (2006.01) |

(52) U.S. Cl.
CPC ............... *C12N 9/22* (2013.01); *C12N 15/63* (2013.01); *C12N 1/205* (2021.05); *C12N 2310/20* (2017.05); *C12R 2001/145* (2021.05)

(58) Field of Classification Search
CPC ...... C12N 15/63; C12N 9/22; C12N 2310/20; C12R 1/145
See application file for complete search history.

(56) References Cited

U.S. PATENT DOCUMENTS

| | | | |
|---|---|---|---|
| 9,284,580 | B2 | 3/2016 | Yang et al. |
| 2009/0111154 | A1 | 4/2009 | Liao et al. |
| 2011/0027845 | A1 | 2/2011 | Lee et al. |
| 2011/0236941 | A1 | 9/2011 | Koepke et al. |

FOREIGN PATENT DOCUMENTS

| | | | |
|---|---|---|---|
| AU | 2007/332240 | B2 | 6/2008 |
| WO | 2008/052973 | | 5/2008 |
| WO | 2012/045022 | | 4/2012 |
| WO | 2015/159086 | | 10/2015 |
| WO | 2015159087 | | 10/2015 |

OTHER PUBLICATIONS

Jang et al., mBio, 3(5), 2012, pp. 1-9.*
Ou, et al, High butanol production by regulating carbon, redox and energy in Clostridia, Front. Chem. Sci. Eng. 2015, 9(3): 317-323.
Pyne et al, Harnessing heterologous and endogenous CRISPR-Cas machineries for efficient markerless genome editing in Clostridium, Scientific Reports, May 2016, 1-15.
Yu et al, Metabolic engineering of Clostridium tyrobutyricum for n-butanol production, Metabolic Engineering 2011, 13(4), 373-382.
Keis, S., Shaheen, R., Jones, D. T., Emended descriptions of *Clostridium acetobutylicum* and *Clostridium beijerinckii*, and descriptions of *Clostridium saccharoperbutylacetonicum* sp. Nov. and *Clostridium saccharobutylicum* sp. nov. International Journal of Systematic and Evolutionary Microbiology 2001, 51, 2095-2103.
Lee, S. Y., Park, J. H., Jang, S. H., Nielsen, L. K., et al., Fermentative butanol production by clostridia. Biotechnology and Bioengineering 2008, 101, 209-228.
Lee, J., Jang, Y.-S., Han, M.-J., Kim, J. Y., Lee, S. Y., Deciphering *Clostridium tyrobutyricum* metabolism based on the whole-genome sequence and proteome analyses. mBio 2016, 7(3):e00743-16.
Zhang, J., Zong, W., Hong, W., Zhang, Z.-T., Wang, Y., Exploiting endogenous CRISPR-Cas system for multiplex genome editing in *Clostridium tyrobutyricum* and engineer the strain for high-level butanol production. Metabolic Engineering 2018, 47, 49-59.
Lehmann, D., Hönicke, D., Ehrenreich, A., Schmidt, M., et al., Modifying the product pattern of *Clostridium acetobutylicum*: physiological effects of disrupting the acetate and acetone formation pathways. Applied Microbiology and Biotechnology2012, 94, 743-754.
Yu, M. R., Zhang, Y. L., Tang, I. C., Yang, S. T., Metabolic engineering of *Clostridium tyrobutyricum* for n-butanol production. Metabolic Engineering 2011, 13, 373-382.

* cited by examiner

*Primary Examiner* — Maryam Monshipouri
(74) *Attorney, Agent, or Firm* — Barnes & Thornburg LLP

(57) ABSTRACT

A system for modifying the genome of *Clostridium* strains is provided based on a modified endogenous CRISPR array. The application also describes *Clostridium* strains modified for enhanced butanol production wherein the modified strains are produced using the novel CRISPR-Cas system.

11 Claims, 14 Drawing Sheets

Specification includes a Sequence Listing.

Fig. 3A

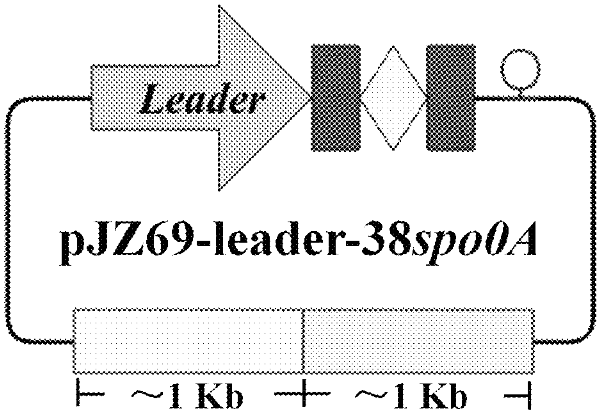

Fig. 3B

| Plasmid | Promoter for *Cas* gene or RNA guide | gRNA or spacer |
|---|---|---|
| pJZ23-Cas9-*spo0A* | P*lac* for Cas9 | 20 nt gRNA |
| pJZ58-nCas9-*spo0A* | P*lac* for nCas9 | 20 nt gRNA |
| pJZ60-AsCpf1-*spo0A* | P*lac* for AsCpf1 | 23 nt crRNA |
| pJZ69-leader-38*spo0A* | Leader for CRISPR array | 38 nt *spo0A* spacer1 |
| pJZ74-P*lac*-10*spo0A* | P*lac* for CRISPR array | 10 nt *spo0A* spacer1 |
| pJZ74-P*lac*-20*spo0A* | P*lac* for CRISPR array | 20 nt *spo0A* spacer1 |
| pJZ74-P*lac*-30*spo0A* | P*lac* for CRISPR array | 30 nt *spo0A* spacer1 |
| pJZ74-P*lac*-38*spo0A* | P*lac* for CRISPR array | 38 nt *spo0A* spacer1 |
| pJZ74-P*lac*-50*spo0A* | P*lac* for CRISPR array | 50 nt *spo0A* spacer1 |
| pJZ75-P*lac*-38*spo0A* | P*lac* for CRISPR array | 38 nt *spo0A* spacer2 |
| pJZ76-P*ara*-38*spo0A* | P*ara* for CRISPR array | 38 nt *spo0A* spacer1 |

Fig. 6A

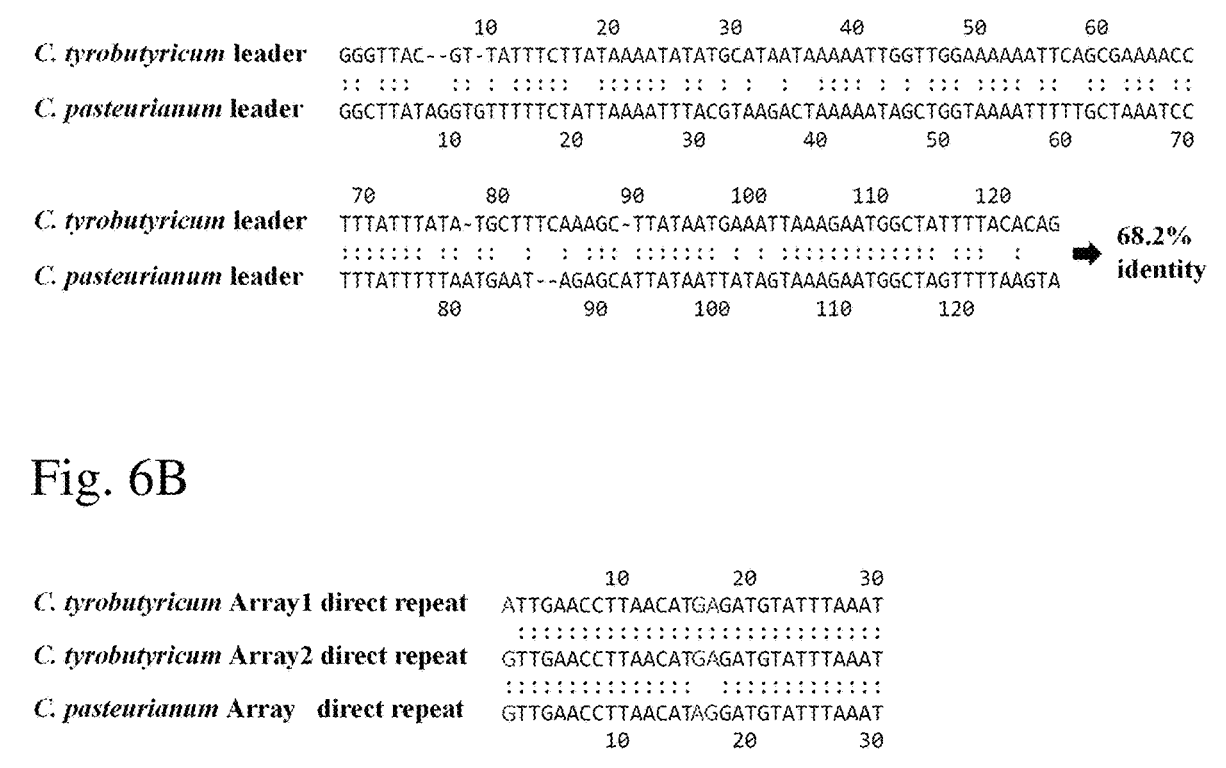

```
                                 10        20        30        40        50        60
C. tyrobutyricum leader     GGGTTAC--GT-TATTTCTTATAAAATATATGCATAATAAAAATTGGTTGGAAAAAATTCAGCGAAAACC

C. pasteurianum leader      GGCTTATAGGTGTTTTTCTATTAAAATTTACGTAAGACTAAAAATAGCTGGTAAAATTTTTGCTAAATCC
                                    10        20        30        40        50        60        70

                            70        80         90       100       110       120
C. tyrobutyricum leader     TTTATTTATA-TGCTTTCAAAGC-TTATAATGAAATTAAAGAATGGCTATTTTACACAG

C. pasteurianum leader      TTTATTTTTAATGAAT--AGAGCATTATAATTATAGTAAAGAATGGCTAGTTTTAAGTA
                                    80          90       100       110       120
```

➡ 68.2% identity

Fig. 6B

```
                                                 10        20        30
C. tyrobutyricum Array1 direct repeat    ATTGAACCTTAACATGAGATGTATTTAAAT

C. tyrobutyricum Array2 direct repeat    GTTGAACCTTAACATGAGATGTATTTAAAT

C. pasteurianum Array   direct repeat    GTTGAACCTTAACATAGGATGTATTTAAAT
                                                 10        20        30
```

CRISPR-CAS SYSTEM FOR *CLOSTRIDIUM* GENOME ENGINEERING AND RECOMBINANT STRAINS PRODUCED THEREOF

CROSS REFERENCE TO RELATED APPLICATIONS

This application claims priority to the following U.S. Provisional Patent Application No. 62/815,198 filed Mar. 7, 2019. The disclosure of which is hereby expressly incorporated by reference in its entirety.

STATEMENT OF GOVERNMENT SUPPORT

This invention was made with government support under Grant number ALA014-1-15017 awarded by the US Department of Agriculture (USDA), National Institute of Food and Agriculture (NIFA). The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: a 40 kilobytes ACII (Text) file named "314658ST25.txt" created on Feb. 20, 2020.

BACKGROUND n-butanol (butanol hereafter) is used as a solvent, paint thinner, perfume, and more recently as a source of renewable fuel. Hence, methods to enhance butanol production are a major focus. However, traditional chemical synthesis methods employed for butanol production are costly and laborious. Furthermore, these methods generate unwanted byproducts and environmental pollutants. Alternative approaches continue to be investigated for their ability to overcome these limitations while also significantly increasing the yield of desired products, particularly butanol. These alternatives include the use of microbial host strains that can be exploited for their natural ability to produce butanol.

Clostridia are a type of bacteria that have long been studied for biobutanol production through their acetone-butanol-ethanol (ABE) fermentation pathway. Although large scale production has already been established using clostridia, there are several obstacles that prevent it from being economically feasible, including high costs and low yields associated with batch fermentation of currently available Clostridia strains.

Recent efforts have focused on modifying the ABE fermentation pathway of clostridia in order to reduce unwanted byproducts while increasing overall yield of butanol. One method used to achieve these modifications involves the use of CRISPR-Cas9 systems which have been widely used as a genome editing tool for numerous types of bacteria. However, conventional CRISPR methods are limited by severe toxicity to the host cells and thus in many cases are difficult to implement. Hence, alternative strategies are needed to improve butanol production while also overcoming existing limitations.

Clustered regularly interspaced short palindromic repeats (CRISPR) and the CRISPR-associated (Cas) system is an RNA guided immune system in bacteria and archaea that can provide defense against foreign invaders, such as phages and plasmids. Most currently identified CRISPR-Cas systems share similar features, consisting of identical direct repeats separated by variable spacers, along with a suite of associated cas genes. CRISPR-Cas systems can be classified into two classes and six types based on the signature Cas proteins and the architecture of CRISPR-cas loci. A complex of multiple Cas proteins are involved in degrading the invading genetic elements in Types I, III and IV, which all belong to the Class 1 system; while Types II, V and VI in the Class 2 system can carry out the same operation by using a single large Cas protein. Among the various CRISPR-Cas systems, Type I, II, and III are the most widespread in both archaea and bacteria, and distinguished by the presence of the unique signature protein: Cas3, Cas9, and Cas10, respectively. Among them, Type I systems exhibit the most diversity, and are further divided into six subtypes: I-A to I-F.

Three functional stages, termed adaptation, expression, and interference, are generally included in the development of the immunity of CRISPR-Cas systems for the defense of the potential foreign invaders. During the adaptation phase, spacer sequences derived from the invading genetic elements are identified and integrated into the host genome right between the leader sequence and the first spacer, generating the new spacers of the CRISPR array. A promoter located within the CRISPR leader sequence then drives the transcription of CRISPR array (including the new spacers) to form a long precursor CRISPR RNA (crRNA) followed by the cleavage of the precursor crRNAs to make mature crRNAs. Once the invasion happens again to the host cells, a ribonucleoprotein complex (crRNP) will be formed by the mature crRNAs and specific Cas proteins to recognize the same or similar foreign genetic elements though sequence matching between the spacer on the crRNA and the protospacer on the foreign invaders, and degrade the invading DNA or RNA via interference. During the interference in Type I and Type II systems, the targeting efficiency is greatly improved if the protospacer is flanked by a short conserved sequence defined as protospacer-adjacent motif (PAM). The PAM sequence is usually 2-5 nucleotides long and located at the 5'- or 3'-end of the protospacer. The presence of PAM sequence in the target DNA rather than in the CRISPR array of the host genome is used to discriminate 'self' and 'non-self'.

Although the Class 2 system is less abundant in the nature, their acting machineries are much simpler and more programmable. In the past few years, the *Streptococcus pyogenes* CRISPR-Cas9 (spCRISPR-Cas9) system has been engineered to be a high efficient genome editing tool that has been implemented in a broad range of organisms, such as bacteria, yeast, plants, mammal cells, and human cells. Besides single gene knock-in or knock-out, successes have also been reported for multiplex genome editing and transcriptional regulation, including repression and activation. Recently, another Class 2 CRISPR effector, Cpf1, was characterized and repurposed for genome editing. Compared to the CRISPR-Cas9 system, the CRISPR-Cpf1 system exhibited higher targeting efficiency and capability under particular circumstances.

CRISPR-Cas9/Cpf1 systems have proven to be powerful genome engineering tools with which versatile genome editing purposes can be achieved. However, as a heterologous protein, in many cases, either Cas9 or Cpf1 is hard to introduce into bacteria and archaea due to their intrinsic toxicity, leading to low transformation efficiency and thus difficulty for genome editing.

It has been reported that, based on genome analysis, approximately 47% of sequenced bacteria and 87% of sequenced archaea harbor CRISPR-cas loci. Therefore, endogenous CRISPR-Cas systems have the potential to be repurposed for genome editing and transcriptional regulation. Through the deletion of cas3 gene which is responsible for degrading the target DNA, the endogenous Type I-E CRISPR-Cas system in *Escherichia coli* was harnessed as a programmable gene expression regulator. Pyne et al. engineered the Type I-B CRISPR-Cas system in *Clostridium pasteurianum* to be an efficient genome editing tool, and successfully deleted the cpaAIR gene (Pyne et al., 2016, Sci. Rep. 6, 25666).

In recent years, the genus *Clostridium* has drawn tremendous attentions as it contains various strains with great potentials for the production of commodity chemicals and fuels, such as butanol. Butanol can be naturally produced in solventogenic clostridia through the Acetone-Butanol-Ethanol (ABE) fermentation. Although tremendous efforts have been invested on the metabolic engineering of solventogenic clostridial strains for enhanced biobutanol production, only very limited success has been achieved. This is because, on one hand, there are several intrinsic byproducts in ABE fermentation including fatty acids, acetone and ethanol that are hard to eliminate; on the other, the ABE fermentation for butanol production goes through a biphasic process and is subjected to complicated metabolic regulation.

Yu et al. engineered *C. tyrobutyricum* ATCC 25755 (a hyper-butyrate producer) for butanol production by inactivating the native acetate kinase (ack) gene or the phosphate++(ptb) gene and introducing the aldehyde/alcohol dehydrogenase (adhE2) from *C. acetobutylicum*, to generate a strain that produces a butanol titer of 10.0 g/L (Yu et al., 2011, Metab. Eng. 13, 373-82). Recently, the butyrate-producing metabolism of *C. tyrobutyricum* was further elucidated through whole-genome sequencing and proteomic analysis. Interestingly, contradictory with the results by Yu et al. (Yu et al., 2011), it was demonstrated that the ptb gene actually does not exist in *C. tyrobutyricum* and the ack gene can't be deleted because the deletion would lead to no end product and inefficient ATP generation. Additionally, it was revealed that the butyrate production in *C. tyrobutyricum* is in fact dependent on the butyrate:acetate CoA transferase gene (cat1), which is very different from the ptb-butyrate kinase (buk) pathway for butyrate production in solventogenic clostridial strains. However, the disruption of cat1 using mobile group II intron was unsuccessful, because the inactivation of cat1 would likely lead to the inability of the strain to carry out NADH oxidization.

Accordingly a need still exists for a bacterial strain that has high levels of butanol production with decreased levels of undesirable by products such as fatty acids and acetone. Applicants provide herein a modified endogenous *C. tyrobutyricum* CRISPR-Cas system under the control of an inducible promoter for modifying the genome of clostridia. This system was used to generate a modified *C. tyrobutyricum* that produces at least 20 g/L of butanol after 72 hours in a standard batch fermentation process.

SUMMARY

As disclosed herein, an efficient genome editing tool for *C. tyrobutyricum*, is provided, based on the endogenous Type I-B CRISPR-Cas system. The PAM sequences for DNA targeting purposes were identified through in silico CRISPR array analysis and in vivo plasmid interference assays. By using a lactose inducible promoter to drive the transcription of the CRISPR array, multiplex genome engineering purposes have been achieved, with an editing efficiency as high as 100%.

In accordance with one embodiment a method of editing a bacterial genome is provided wherein the method utilizes an endogenous CRISPR-Cas system. One component of the system is a synthetic CRISPR array that is optionally expressed under the control of an inducible promoter. The CRISPR array encodes a spacer RNA that targets a protospacer sequence contained within the bacterial genome. The encoded array in conjunction with the native *Clostridium* Cas protein forms a complex that will cleave the targeted DNA. In one embodiment the method comprises introducing an exogenous nucleic acid into the bacterial cell wherein the exogenous nucleic acid comprises a sequence that encodes a synthetic CRISPR array that is operably linked to an inducible promoter, and optionally the exogenous nucleic acid further comprises nucleic acid sequences that are homologous to sequences flanking the target protospacer sequence to facillitate the modification of the target genome loci through homologous recombination.

In accordance with one embodiment the endogenous CRISPR-Cas system of *C. tyrobutyricum*, was used to successfully engineer *C. tyrobutyricum* for enhanced butanol production. By introducing an adhE2 gene and inactivating the native cat1 gene, the obtained mutant produced a record high of 26.2 g/L butanol in a batch fermentation. This mutant bacterial strain of *Clostridium tyrobutyricum* JZ100 was deposited in accordance with the provisions of the Budapest Treaty on Nov. 5, 2017, with the Agriculture Research Culture Collection (NRRL), an International Depository Authority located at 1815 N. University Street, Peoria, Ill. 61604 and assigned accession number B-67519. This deposited strain can be used as a robust workhorse for efficient biobutanol production from low-value carbon sources, and can be further engineered for enhanced butanol and other valuable biochemical production.

In accordance with one embodiment a vector for introducing modifications into a target genomic site of bacteria, optionally a *Clostridium* strain, via an endogenous CRISPR-Cas complex is provided. In one embodiment the vector comprises a synthetic CRISPR array, an inducible promoter operably linked to the synthetic CRISPR array, and a first homology arm polylinker site. In one embodiment the vector further comprises a native *Clostridium tyrobutyricum* Cas encoding sequence. In one embodiment the synthetic CRISPR array comprises a first spacer polylinker site, a first and second direct repeat sequence, and a CRISPR terminator sequence. In one embodiment the first and second direct repeat sequence have greater than 95% sequence identity to one another, or optionally, have 100% sequence identity to one another, and the first spacer polylinker site is located between the first and second direct repeat sequence.

In one embodiment a vector for introducing modifications into a target genomic site of a *Clostridium* strain is provided wherein the vector comprises a synthetic CRISPR array, a lactose inducible promoter operably linked to the synthetic Type I-B CRISPR array, a first homology arm polylinker site, and optionally a CRISPR terminator sequence. In one embodiment the synthetic CRISPR array comprises a first spacer polylinker site, and a first and second direct repeat sequences, wherein the first and second direct repeat sequences each comprise a sequence of SEQ ID NO: 2; and the first spacer polylinker site located between the first and second direct repeat sequences. In a further embodiment the CRISPR terminator sequence comprises the sequence of SEQ ID NO 3.

In accordance with one embodiment a vector for multiplex modification of a bacterial genome, optionally a *Clostridium* strain, via a CRISPR-Cas complex is provided. In one embodiment the vector comprises a synthetic CRISPR array, an inducible promoter operably linked to the synthetic CRISPR array, a first homology arm polylinker site and a second homology arm polylinker site. In one embodiment the synthetic CRISPR array comprises a first spacer polylinker site a second spacer polylinker site, and a first, second and third direct repeat sequences, wherein the first, second and third direct repeat sequences each have greater than 95% sequence identity, or optionally at least 99% sequence identity to the sequence of SEQ ID NO: 2, and the first spacer polylinker site is located between the first and second direct repeat sequences and the second spacer polylinker site located between the second and third direct repeat sequences, and a CRISPR terminator sequence located after the third direct repeat sequence.

In accordance with one embodiment a recombinant *Clostridium* strain is provided that has been modified for enhanced butanol production. In one embodiment, the *Clostridium* strain produces at least 20 g/L of butanol after 72 hours of culture in a standard batch culture procedure using glucose as the carbon source. In one embodiment the modified *Clostridium* strain comprises an exogenous gene encoding for aldehyde dehydrogenase activity, optionally wherein the exogenous gene has been inserted into the native cat1 gene and prevents expression of a functional cat1 gene product. In one embodiment the exogenous aldehyde dehydrogenase gene is a dual aldehyde/alcohol dehydrogenase gene including for example a *C. acetobutylicum* gene selected from the group consisting of adhE1 and adhE2. In one embodiment the recombinant *Clostridium* strain is selected from the group consisting of *Clostridium butyricum, Clostridium thermobutyricum, Clostridium cellulovorans, Clostridium carboxidivorans, Clostridium tyrobutyricum, Clostridium polysaccharolyticum, Clostridium populeti*, and *Clostridium kluyveri*. In one embodiment the *Clostridium* strain is *Clostridium tyrobutyricum.*

In one embodiment a method of biosynthetically producing butanol is provided, wherein a modified *Clostridium* strain is cultured under conditions suitable for growth of the strain, and the butanol produce by the cell is recovered. In one embodiment the modified *Clostridium* strain comprises a modification to the native cat1 gene (wherein the modification inhibits or prevents expression of a functional cat1 gene product); and an exogenous aldehyde dehydrogenase gene, optionally wherein the aldehyde dehydrogenase gene is inserted in to the genome of the *Clostridium* strain. Optionally the exogenous aldehyde dehydrogenase gene encodes a polypeptide having alcohol dehydrogenase and aldehyde dehydrogenase activity. In one embodiment the exogenous aldehyde dehydrogenase gene is selected from the group consisting of adhE1 and adhE2, optionally wherein the adhE1 gene encodes a polypeptide having at least 95% sequence identity to the polypeptide of SEQ ID NO: 133 and the adhE2 gene encodes a polypeptide having at least 95% sequence identity to the polypeptide of SEQ ID NO: 134. In accordance with one embodiment the *Clostridium* strain comprises a cat1 gene modified by the insertion of an adhE1 or adhE2 gene into the cat1 gene, rendering the cat1 gene incapable of expressing a functional gene product. In one embodiment the culturing step comprises culturing the modified *Clostridium* strain at a temperature less than 37° C., optionally at a temperature selected from the range of about 20° C. to about 30° C.

BRIEF DESCRIPTION OF THE DRAWINGS

FIG. 1A is a schematic diagram showing the structure of the central Type I-B CRISPR-Cas locus in the genome of *C. tyrobutyricum*. The central CRISPR-Cas locus possesses a representative Type I-B cas operon including cas6-cas8b-cas7-cas5-cas3-cas4-cas1-cas2 (labeled "cas68b753412") followed by a leader sequence and the Array2 containing 8 distinct spacers (diamonds) separated by 30-nt direct repeats (rectangles) and a CRISPR terminator sequence (open circle). The transcription of Array2 is driven by a promoter within the leader sequence. FIG. 1B provides sequence assignments providing an identification of putative protospacer matches via in silico analysis of *C. tyrobutyricum* CRISPR spacers. Only five nt of the 5'- and 3'-end adjacent sequences are provided. Array1-17 (SEQ ID NO: 19); *C. themocellum* ATCC 27405 (SEQ ID NO: 20) and *Geobacillus* sp. Y4.1MC1 (SEQ ID NO: 21).

FIG. 2A provides a map of plasmids used in systematic mutagenesis assays, including the protospacer (SEQ ID NO: 21) with a 5' PAN sequence. Mutation positions were indicated on the PAM sequence. Array2-1 (Table 1) was used as the protospacer. FIG. 2B presents data in a bar graph testing several variant PAM sequences used in the assay and their corresponding transformation efficiencies. The plasmid pMTL82151 (PAM, –; Mutation position, –) was used as the control. Data are based on at least two independent replicates.

FIGS. 3A-3D: Markerless genome editing in *C. tyrobutyricum* using the endogenous Type I-B CRISPR-Cas system. FIG. 3A provides a schematic drawing that illustrates the steps involved in deleting the spo0A gene via a lactose inducible CRISPR-Cas system. The lactose inducible promoter was used to drive the transcription of synthetic CRISPR array, wherein the array comprises a spacer (diamonds) separated by 30-nt direct repeats (rectangles). ~1 kb upstream and downstream homology arms (flanking the native spo0A gene) were used for the deletion of spo0A gene. Two screening steps are involved in the process. In the first step, the plasmid was transformed into *C. tyrobutyricum* under the selection of thiamphenicol (Tm). In the second step, lactose was applied to induce the transcription of synthetic CRISPR array and eliminate the wild type background cells, thus selecting for the desirable mutant. Pairs of half arrows and the numbers in the figure indicate the cPCR target regions and the PCR amplicon sizes, respectively. FIG. 3B is a table presenting the various plasmids carrying the CRISPR-Cas9/nCas9/AsCpf1 and Type I-B CRISPR-Cas systems that were tested for the deletion of spo0A. Promoters and the length of spacers were optimized for the CRISPR-Cas system in order to improve the transformation efficiency and editing efficiency. The inducible promoters tested include the lactose inducible promoter (Plac) and the arabinose inducible promoter (Para). FIG. 3C provides data in a bar graph format showing the transformation efficiency of different plasmids. Data are based on at least two independent replicates. FIG. 3D provides data in a bar graph format demonstrating the genome editing efficiency of different plasmids that can be transformed into *C. tyrobutyricum*. Fifteen colonies of each transformant were picked and screened for mutation. The editing efficiency were calculated as the ratio of the number of spo0A mutants to the total of fifteen colonies.

FIG. 4A provides a schematic drawing illustrating the use of the lactose inducible CRISPR-Cas system to conduct a double deletion of both the spo0A and pyrF genes. The deletion vector comprises a CRISPR array under the control of a lactose promoter and including spacers (diamonds) targeting the spo0A and pyrF genes, respectively, where each spacer is flanked by a 30 nucleotide direct repeat (rectangles) and a nucleic acid sequence of ~1.2 kb upstream and downstream of both spo0A and pyrF, respectively (~300 bp each) used to create homology arms to induce homologous recombination after cleavage by the CRISPR-Cas system. The screening procedure of double deletion was similar with that for single deletion, except that a series of subculturing was required before plating the culture on the TGYLTU plates. Pairs of half arrows and the numbers in the figure indicate the cPCR target regions and the PCR amplicon sizes, respectively. Detection of gene deletion events was carried out at the 8th (FIG. 4B) and 15th (FIG. 4C) generations during the subculturing. Single deletion vectors pJZ77-Plac-30spo0A and pJZ77-Plac-30pyrF were used as controls. 47 colonies of each transformant were picked and screened for mutations. The white rectangles, grey rectangles, and black rectangles represent wild type strain, single deletion mutant of spo0A or pyrF, and double deletion mutant, respectively.

FIGS. 6A & 6B show alignments of the *C. tyrobutyricum* and *C. pasteurianum* leader sequences (FIG. 6A; SEQ ID NO: 23 and 24, respectively) and the *C. tyrobutyricum* Array1, Array2 and *C. pasteurianum* direct repeat sequences (FIG. 6B; SEQ ID NO: 18, 2 and 25, respectively) of the CRISPR array.

FIG. 7A provides the results from culturing WT(pJZ98-Pcat1-adhE1) at 37° C.; FIG. 7B provides the results from culturing mutant Δcat1::adhE1 at 37° C.; FIG. 7C provides the results from culturing mutant Δcat1::adhE1 at 30° C.; FIG. 7D provides the results from culturing mutant Δcat1::adhE1 at 25° C.; and FIG. 7E provides the results from culturing mutant Δcat1::adhE1 at 20° C. Values are based on at least two independent replicates.

FIG. 8A provides the results from culturing WT(pJZ98-Pcat1-adhE2) at 37° C.; FIG. 8B provides the results from culturing mutant Δcat1::adhE2 at 37° C.; FIG. 8C provides the results from culturing mutant Δcat1::adhE2 at 30° C.; FIG. 8D provides the results from culturing mutant Δcat1::adhE2 at 25° C.; and FIG. 8E provides the results from culturing mutant Δcat1::adhE2 at 20° C. Values are based on at least two independent replicates.

DETAILED DESCRIPTION

Definitions

Figure 1A:
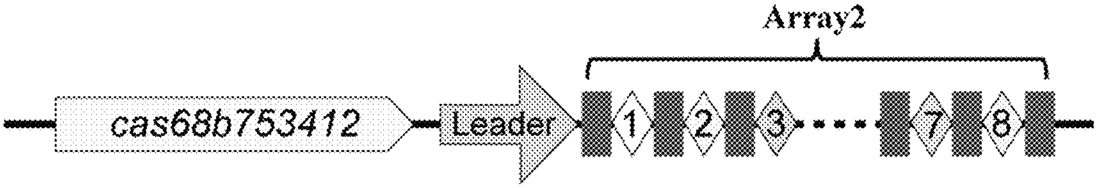
FIGS. 1A & 1B Characterization of the Type I-B CRISPR-Cas system in *C. tyrobutyricum*.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein an "amino acid modification" defines a substitution, addition or deletion of one or more amino acids, and includes substitution with or addition of any of the 20 amino acids commonly found in human proteins, as well as atypical or non-naturally occurring amino acids.

The term "substantially purified polypeptide/nucleic acid" refers to a polypeptide/nucleic acid that may be substantially or essentially free of components that normally accompany or interact with the polypeptide/nucleic acid as found in its naturally occurring environment.

A "recombinant host cell" or "host cell" refers to a cell that includes an exogenous polynucleotide, regardless of the method used for insertion. The exogenous polynucleotide may be maintained as a nonintegrated vector, for example, a plasmid, or alternatively, may be integrated into the host genome.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or an amino acid with a chemically similar amino acid. Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

The term "linkage" or "linker" is used herein to refer to groups or bonds that normally are formed as the result of a chemical reaction and typically are covalent linkages.

An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of an RNA.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

As used herein a general reference to a polypeptide is intended to encompass polypeptides that have modified amino and carboxy termini. For example, an amino acid chain comprising an amide group in place of the terminal carboxylic acid is intended to be encompassed by an amino acid sequence designating the standard amino acids.

As used herein an amino acid "substitution" refers to the replacement of one amino acid residue by a different amino acid residue.

As used herein, the term "CRISPR-Cas system" defines a complex comprising a Cas protein and a spacer RNA.

The terms "target sequence," "target DNA," and "target site" are used interchangeably to refer to the specific sequence in chromosomal DNA to which the engineered CRISPR-Cas system is targeted, and the site at which the engineered CRISPR-Cas system modifies the DNA.

The terms "upstream" when used in the context of a nucleic acid sequence, identifies a nucleic acid sequence that is located on the 5' side of a reference nucleic acid sequence. For example a promoter is located upstream of a nucleic acid coding sequence.

The terms "downstream" when used in the context of a nucleic acid sequence identify nucleic acid sequence that are located on the 3' side of a reference nucleic acid sequence. For example a transcriptional terminator sequence is located downstream of a nucleic acid coding sequence.

The term "direct repeat sequence" defines an RNA strand that participates in recruiting a CRISPR endonucleases to the target site.

As used herein the term "guide sequence" or "spacer" defines a DNA sequence that transcribes an RNA strand that hybridizes with the target DNA.

The term "protospacer" refers to the DNA sequence targeted by a spacer sequence. The protospacer typically comprises the spacer sequence covalently linked to a protospacer adjacent motif (PAM). PAM is a 2-6-base pair DNA sequence immediately preceding or following the DNA sequence targeted by the Cas nuclease in the CRISPR-Cas system. In some embodiments, the protospacer sequence hybridizes with the spacer sequence of the CRISPR-Cas system.

The term "endogenous" as used herein, refers to a natural state. For example a molecule (such as a direct repeat sequence) endogenous to a cell is a molecule present in the cell as found in nature. A "native" compound is an endogenous compound that has not been modified from its natural state.

As used herein, the term "exogenous" refers to a molecule not present in the composition found in nature. A nucleic acid that is exogenous to a cell, or a cell's genome, is a nucleic acid that comprises a sequence that is not native to the cell/cell's genome.

EMBODIMENTS

As disclosed herein, an efficient genome editing tool for *C. tyrobutyricum*, is provided, based on the endogenous Type I-B CRISPR-Cas system. Advantageously, this novel genome editing tool has been used to modify the genome of *Clostridium* strain to produce a novel strain having improved production of butanol.

In accordance with one embodiment a recombinant microorganism is provided that produces butanol while the microorganism is cultured under conditions favorable for growth. In particular, in one embodiment a microorganism has been modified for increased expression of aldehyde dehydrogenase activity by the addition of an exogenous gene that encodes for aldehyde dehydrogenase activity, optionally wherein the ability of the cat1 gene to produce a functional protein has been decreased or eliminated. In one embodiment the recombinant microorganism has been modified by the integration of an exogenous gene encoding for aldehyde dehydrogenase activity, optionally wherein the exogenous gene also encodes for alcohol dehydrogenase activity. In one embodiment the dehydrogenase activity is an alcohol dehydrogenase activity. In one embodiment the exogenous gene encodes for both aldehyde dehydrogenase activity and alcohol dehydrogenase activity. In one embodiment the exogenous gene is an aldehyde/alcohol dehydrogenase gene having at least about 80%, 85%, 90%, 95% or 99% sequence identity to SEQ ID NO: 133 or SEQ ID NO: 134. In one embodiment the exogenous gene is the adhE1 or adhE2 gene from *C. acetobutylicum.*

In one embodiment the modified microorganism is a *Clostridium* strain, including for example a *Clostridium* strain selected from the group consisting of *Clostridium butyricum, Clostridium thermobutyricum, Clostridium cellulovorans, Clostridium carboxidivorans, Clostridium tyrobutyricum, Clostridium polysaccharolyticum, Clostridium populeti*, and *Clostridium kluyveri*. In one embodiment the *Clostridium* strain is *Clostridium tyrobutyricum.*

In one embodiment a recombinant *Clostridium* strain modified for enhanced butanol production is provided wherein the *Clostridium* strain comprises an exogenous aldehyde dehydrogenase gene inserted in to the genome of the *Clostridium* strain and a modification to the native cat1 gene, wherein the modification inhibits or prevents expression of a functional cat1 gene product. In one embodiment the exogenous aldehyde dehydrogenase gene encodes for both alcohol dehydrogenase and aldehyde dehydrogenase activity, including for example a *C. acetobutylicum* gene selected from the group consisting of adhE1 and adhE2. In one embodiment the dehydrogenase gene is an adhE1 gene that encodes a protein having at least 80%, 85%, 90%, 95% or 99% sequence identity to SEQ ID NO: 133. In one embodiment the dehydrogenase gene is an adhE2 gene that encodes a protein having at least 80%, 85%, 90%, 95% or 99% sequence identity to SEQ ID NO: 134. In accordance with one embodiment a modified *Clostridium* is provided wherein the cat1 gene is modified by the insertion of an adhE1 or adhE2 gene into the cat1 gene rendering the cat1 gene incapable of expressing a functional gene product.

In accordance with one embodiment a modified strain of *Clostridium* is provided wherein butanol is produced by the organism at a level of at least 15 g/L, when the cells are cultured at a temperature selected from about 20° C. to about 30° C. in the presence of a carbon source such as glucose. In accordance with one embodiment a modified strain of *Clostridium* is provided wherein butanol is produced by the organism at a level of at least 20 g/L, when the cells are cultured at a temperature selected from about 20° C. to about 30° C. In accordance with one embodiment a modified strain of *Clostridium* is provided wherein butanol is produced by the organism at a level of at least 15 g/L wherein the levels of acetate and ethanol are less than 10 g/L, when the cells are cultured at a temperature selected from about 20° C. to about 30° C.

In accordance with one embodiment a recombinant *Clostridium* strain is provided, wherein the strain when cultured at a temperature of less than 30° C. using glucose as a carbon source, produces at least 20 g/L of butanol, and less than 15 g/L of acetate, after 72 hours of culture. In accordance with one embodiment a recombinant *Clostridium* strain is provided, wherein the strain when cultured at a temperature of selected from a range of about 20° C. to about 30° C. using glucose as a carbon source, produces at least 25 g/L of butanol, and less than 15 g/L of acetate, after 120 hours of culture. In one embodiment the *Clostridium* strain is *Clostridium tyrobutyricum.*

In one embodiment a *Clostridium* strain modified for enhanced butanol production is provided wherein the strain comprises an exogenous gene encoding for aldehyde dehydrogenase activity, and a modified native *Clostridium* cat1 gene, wherein the modification prevents expression of a functional cat1 gene product, further wherein the modified strain, when cultured at a temperature of less than 30° C. using glucose as a carbon source, produces at least 20 g/L of butanol after 72 hours of culture. In one embodiment the exogenous gene is inserted into the cat1 gene rendering the cat1 gene incapable of expressing a functional gene product. In one embodiment the exogenous gene is an adhE gene having at least 95% sequence identity to SEQ ID NO: 133 or SEQ ID NO: 134. In one embodiment the exogenous gene is an adhE1 or adhE2 gene.

In one embodiment a *Clostridium* strain modified for enhanced butanol production is provided wherein the strain comprises a modification to the native cat1 gene, wherein the modification preventing expression of a functional cat1 gene product, and an exogenous sequence encoding i) an aldehyde dehydrogenase;
ii) a bifunctional aldehyde/alcohol dehydrogenase; or
iii) an aldehyde dehydrogenase and an alcohol dehydrogenase. In one embodiment the *Clostridium* strain is a recombinant organism wherein the cat1 gene is modified by the insertion of the exogenous sequence into the cat1 gene rendering the cat1 gene incapable of expressing a functional gene product. More particularly, in one embodiment the recombinant *Clostridium* strain the inserted exogenous sequence comprises an bifunctional alcohol/aldehyde dehydrogenase gene selected from the group consisting of adhE1 and adhE2, wherein the strain, when cultured at a temperature of less than 30° C. using glucose as a carbon source, produces at least 20 g/L of butanol after 72 hours of culture.

In accordance with one embodiment a recombinant *Clostridium* strain modified for enhanced butanol production is provided wherein the *Clostridium* strain comprises an exogenous gene encoding for aldehyde dehydrogenase activity inserted into the genome of the strain, and a modified native *Clostridium* cat1 gene, wherein the modification to the native *Clostridium* cat1 gene prevents expression of a functional cat1 gene product. In one embodiment, the recombinant *Clostridium* strain, when cultured at a temperature of less than 30° C. using glucose as a carbon source, produces at least 20 g/L of butanol and less than 15 g/L of acetate after 72 hours of culture. In one embodiment the exogenous gene encoding for aldehyde dehydrogenase activity is an adhE1 or adhE2 gene that is inserted into the *Clostridium* native cat1 gene rendering the cat1 gene incapable of expressing a functional gene product. In one embodiment a modified *Clostridium tyrobutyricum* strain (*Clostridium tyrobutyricum* JZ100) is provided that has enhanced production of butanol relative to the native strain. A representative sample of this modified strain was deposited in accordance with the provisions of the Budapest Treaty on Nov. 5, 2017, with the Agriculture Research Culture Collection (NRRL), an International Depository Authority located at 1815 N. University Street, Peoria, Ill. 61604, and assigned accession number B-67519.

In accordance with one embodiment the novel modified microorganisms described herein are used in methods of producing butanol and other biofuels. In certain of these embodiments, the methods include culturing one or more different recombinant microorganisms in a culture medium, and accumulating butanol in the culture medium. In one embodiment a method of producing butanol is provided wherein a recombinant *Clostridium* strain modified for enhanced butanol production is cultured under conditions suitable for growth of the strain, and the butanol produced by the cells are recovered. In one embodiment the cultured *Clostridium* strain is a strain that has been modified to inactivate the native cat1 gene, and further modified to have enhanced aldehyde dehydrogenase and alcohol dehydrogenase activity. In one embodiment the enhanced aldehyde dehydrogenase activity is provided by introducing an exogenous aldehyde dehydrogenase gene into the *Clostridium* strain, optionally inserting an exogenous aldehyde dehydrogenase into genome of the cell and in one embodiment inserting the aldehyde dehydrogenase gene into the native cat1 gene and thus inactivating the cat1 gene. In one embodiment the exogenous aldehyde dehydrogenase gene is a bifunctional aldehyde/alcohol dehydrogenase including for example adhE1 or adhE2.

In one embodiment the method of producing butanol comprises culturing a novel *Clostridium* strain as disclosed herein at a temperature less than 37° C. Optionally the *Clostridium* strain is cultured at a temperature selected from the range of about 20° C. to about 35° C., or about 20° C. to about 30° C., or about 25° C. to about 30° C., or about 20° C. to about 25° C., or at about 30° C., or at about 25° C. or at about 20° C.

In accordance with one embodiment a method of editing a bacterial genome is provided that is based on a modified endogenous CRISPR array. One embodiment of the present disclosure is directed to an enhanced butanol producing *Clostridium* strain produced by the novel CRISPR-CAS system disclosed herein and the use of such novel strains to produce butanol.

In one embodiment the novel CRISPR-CAS system comprises an endogenous CRISPR array under the control of an inducible promoter that drives the expression of a spacer RNA that targets a protospacer sequence contained within a bacterial genome, resulting in a double strand break in the targeted DNA. In one embodiment a method of modifying a *Clostridium* strain comprises introducing an exogenous nucleic acid (i.e., a vector) into the bacterial cell wherein the exogenous nucleic acid comprises a sequence that encodes a synthetic CRISPR array under the control of an inducible promoter. In one embodiment the synthetic CRISPR array comprises a first and second direct repeat, a spacer polylinker site, wherein the spacer polylinker site is located between the first and second direct repeat, and a CRISPR terminator sequence located after the second direct repeat. The spacer polylinker site provides a plurality of restriction enzyme target sequences that allow for the easy insertion of a spacer sequence of choice. Advantageously, this vector allows one to substitute sequences to direct the CRISPR-CAS system to modify a target protospacer sequence of choice present in the bacterial genome. The modification of the target sequence can be enhanced by including sequences that are homologous to the upstream and/or downstream regions of the target protospacer. Accordingly, in one embodiment the exogenously introduced nucleic acid (vector) comprises a homology arm polylinker site, wherein the homology arm polylinker site comprises a plurality of restriction enzyme target sequences, that differ from those of the spacer polylinker site, and allow for the easy insertion of sequences homologous to the upstream and/or downstream regions of the target protospacer.

In one embodiment the first and second direct repeat are based on the endogenous Type I-B CRISPR-Cas system of *C. tyrobutyricum*. The direct repeats will typically be identical in sequence relative to one another but in one embodiment the directs repeat sequences can vary by one or two nucleotide differences or the two direct repeats can have greater than 95% or 99% sequence identity to one another and are orientated relative to each other as direct repeated sequences on either side of a spacer polylinker/spacer sequence. In one embodiment the direct repeats comprise a sequence that has at least 80%, 85%, 90% 95% or 99% sequence identity to SEQ ID NO: 2. In one embodiment the two direct repeat sequences independently comprise a sequence having at least 95% sequence identity to the sequence of SEQ ID NO: 2. In one embodiment the two direct repeat sequences each comprise the sequence of SEQ ID NO: 2.

In one embodiment the exogenously nucleic acid sequence further comprises sequence encoding for a *Clostridium tyrobutyricum* Cas protein. A vector that further comprises the *Clostridium tyrobutyricum* Cas protein can beneficially be used to induce modifications into *Clostridium* strains other than *Clostridium tyrobutyricum* through the use of the CRISPR-Cas system disclosed herein.

In accordance with one embodiment a vector for introducing modifications into a target genomic site of bacteria via a CRISPR-Cas complex is provided, wherein the target genomic site is a contiguous nucleic acid sequence comprising a first protospacer sequence, a first upstream sequence and a first downstream sequence. More particularly, in one embodiment the vector comprises a synthetic CRISPR array, an inducible promoter operably linked to the synthetic CRISPR array and a first homology arm polylinker site, wherein the synthetic CRISPR array comprises a first and second direct repeat, a first spacer polylinker site, wherein the first spacer polylinker site is located between the first and second direct repeat and a CRISPR terminator sequence located after the second direct repeat. In one embodiment first and second direct repeat independently comprise a sequence having at least 95% sequence identity to the sequence of SEQ ID NO: 2, and the CRISPR terminator sequence comprises a sequence having at least 95% sequence identity to the sequence of SEQ ID NO: 3. In one embodiment the first and second direct repeat each comprise the sequence of SEQ ID NO: 2, and the CRISPR terminator sequence comprises the sequence of SEQ ID NO: 3. In one embodiment the inducible promoter is any bacterial promoter known to those skilled in the art whose promoter activity can be regulated by one or more inducer agents. In one embodiment the inducible promoter is a lactose inducible promoter and the inducing agent is lactose or a lactose analog such as IPTG. In one embodiment the vector further comprises a native *Clostridium tyrobutyricum* Cas encoding sequence, optionally wherein the native *Clostridium tyrobutyricum* Cas encoding sequence is operably linked to an inducible promoter.

The vectors described herein can be further modified for multiplex editing of multiple target sites based on the number of spacer sequences are present in the inducible CRISPR array. For example, in one embodiment a vector is provided for introducing modifications into a first and second target genomic site of bacteria via a CRISPR-Cas complex of the present disclosure. In this embodiment a first target genomic site is a contiguous nucleic acid sequence comprising a first protospacer sequence, a first upstream sequence and first downstream sequence, and the second target genomic site is a contiguous nucleic acid sequence comprising a second protospacer sequence, a second upstream sequence and second downstream sequence, and the vector comprises a first and second homology arm polylinker site. The synthetic CRISPR array of such a vector comprises a first, second and third direct repeat, wherein the wherein the first second and third direct repeat comprises a sequence having at least 95% sequence identity to the sequence of SEQ ID NO: 2. Optionally the first, second and third direct repeat sequence are identical to SEQ ID NO: 2. The synthetic CRISPR array further comprises a first and second spacer polylinker site, wherein the first spacer polylinker site located between the first and second direct repeat, and wherein the second spacer polylinker site located between the second and third direct repeat, optionally wherein the synthetic CRISPR array further comprises a CRISPR terminator sequence is located after the third direct repeat. In one embodiment the CRISPR terminator sequence comprises the sequence of SEQ ID NO: 3.

In one embodiment the vector comprises a first spacer sequence inserted into the first spacer polylinker site and a first and second homology arm sequence inserted into the first homology arm polylinker site, wherein the first homology arm sequence comprises a nucleotide sequence sharing at least about 90%, 95% or 99% sequence identity to the first upstream sequence, and the second homology arm comprises a nucleotide sequence sharing at least about 90%, 95% or 99% sequence identity to the first downstream sequence. In one embodiment the spacer sequence is 10 to 100, or 20 to 60, or 20 to 50, or 25 to 50 or 30 to 40 nucleotides in length. In one embodiment the spacer comprises the sequence of SEQ ID NO: 4. In one embodiment the first homology arm sequence comprises a nucleotide sequence having 100% sequence identity to the first upstream sequence, and the second homology arm comprises a nucleotide sequence having 100% sequence identity to the first downstream sequence.

In embodiments targeting two or more target protospacer sequences in a bacterial genome the vector comprises a first spacer sequence inserted into the first spacer polylinker site;

a second spacer sequence of inserted into the second spacer polylinker site;

a first and second homology arm sequence inserted into the first homology arm polylinker site, wherein the first homology arm sequence comprises a nucleotide sequence sharing at least about 90%, 95% or 99% sequence identity to the first upstream sequence, and the second homology arm comprises a nucleotide sequence sharing at least about 90%, 95% or 99% sequence identity to the first downstream sequence; and a third and fourth homology arm sequence inserted into the second homology arm polylinker site, wherein the third homology arm sequence comprises a nucleotide sequence sharing at least about first homology arm sequence comprises a nucleotide sequence sharing at least about 90%, 95% or 99% sequence identity to the second upstream sequence, and the second homology arm comprises a nucleotide sequence sharing at least about 90%, 95% or 99% sequence identity to the second downstream sequence.

The present disclosure further encompasses any bacterial strain comprising an inducible CRISPR array vector of the present disclosure.

In accordance with one embodiment a method of producing butanol is provided wherein the method comprises the steps of culturing a *Clostridium* strain modified in accordance with the present disclosure to produce increased levels of butanol relative to the unmodified strain under conditions suitable for growth of the strain. In one embodiment the method comprises culturing the strain in the presence of a carbon source such as glucose or other sugar at a temperature at or below 37° C. In one embodiment the cells are cultured at a temperature below 37° C., optionally at a temperature selected from a range of about 20° C. to about 35° C.; or about 20° C. to about 30° C.; or about 25° C. to about 30° C.; or about 30° C., about 25° C.; or about 20° C. to about 20° C. The butanol produce by the modified cells can be collected after 48 or 72 hours of culture or longer.

In accordance with one embodiment a method of modifying a target site of a bacterial cell genome is provided wherein the method comprises transforming a bacterial cell with the vector of the present disclosure and selecting for transformants comprising the vector;

inducing the expression of the Type I-B CRISPR array; and identifying recombinant bacteria having a modification to the target site of the genome. Subsequent to the modification to the genome, the originally introduced vector can be eliminated from the cell. In one embodiment the introduced vector exists as an extra-chromosomal vector that is maintained in the bacterial by a selectable marker such as an antibiotic resistance gene. In one embodiment the method comprises targeting the endogenous cat1 gene and the vector comprises a spacer sequence of

```
                                      (SEQ ID NO: 4)
CTTGTAGAAGATGGATCAACCCTACAACTTGGTA.
```

Example 1

Exploitation of Type I-B CRISPR-Cas of *Clostridium tyrobutyricum* for Genome Engineering.

The endogenous Type I-B CRISPR-Cas of *Clostridium tyrobutyricum* was analyzed for its ability to function as a tool for modifying targeted sequence present in the genome of *Clostridium tyrobutyricum*. In silico CRISPR array analysis and plasmid interference assay revealed that TCA or TCG at the 5'-end of the protospacer was the functional protospacer adjacent motif (PAM) for CRISPR targeting. With use of a lactose inducible promoter for CRISPR array expression, applicant significantly decreased the toxicity of CRISPR-Cas and enhanced the transformation efficiency of constructs that encoded the CRISPR-Cas complex. Applicants the effectiveness of the endogenous Type I-B CRISPR-Cas by successfully deleting the native spo0A gene with an editing efficiency of 100%. Applicant further evaluated effects of the spacer length on genome editing efficiency. Interestingly, spacers ≤20 nt led to unsuccessful transformation consistently, likely due to severe off-target effects; while a spacer of 30-38 nt is most appropriate to ensure successful transformation and high genome editing efficiency. Moreover, multiplex genome editing for the deletion of spo0A and pyrF was achieved in a single transformation, with an editing efficiency of up to 100%. Finally, with the integration of the aldehyde/alcohol dehydrogenase gene (adhE1 or adhE2) to replace cat1 (the key gene responsible for butyrate production and previously could not be deleted), two mutants were created for n-butanol production, with the butanol titer reached historically record high of 26.2 g/L in a batch fermentation. Altogether, these results demonstrate the programmability and high efficiency of endogenous CRISPR-Cas. The developed protocol herein has a broader applicability to other prokaryotes containing endogenous CRISPR-Cas systems. *C. tyrobutyricum* could be employed as an excellent platform to be engineered for biofuel and biochemical production using the CRISPR-Cas based genome engineering toolkit.

Materials and Methods

Bacterial Strains and Cultivation

All the strains used in this study are listed in Table 3. The *E. coli* strain NEB Express (New England BioLabs Inc., Ipswich, Mass.) was used for general plasmid propagation. *E. coli* CA434 was employed as the donor strain for conjugation. All *E. coli* strains were routinely cultivated in Luria-Bertani (LB) broth or on solid LB agar plate supplemented with 30 μg/mL chloramphenicol (Cm) or 50 μg/mL kanamycin (Kan) when required. *C. tyrobutyricum* ATCC 25755 (KCTC 5387) was obtained from the American Type Culture Collection (ATCC, Manassas, Va., USA) and propagated anaerobically at 37° C. in Tryptone-Glucose-Yeast extract (TGY) medium. 15 μg/mL thiamphenicol (Tm), 250 g/mL D-cycloserine, 40 mM lactose or 20 μg/mL uracil was added into the medium when required.

Identification and Analysis of Putative Protospacer Matching CRISPR Spacers of *C. tyrobutyricum*

Nucleotide BLAST was used to analyze the CRISPR spacers of *C. tyrobutyricum*, by aligning the spacer sequences against the existing genome sequences in the National Center for Biotechnology Information (NCBI) database. Putative protospacers were inspected for their matching with the spacers as the putative invading DNA elements, such as phage (prophage), plasmid, transposon, integrase, and so on. For the analysis, we set a maximum of 15% (a maximum of 5/34 mismatching nucleotides) for the mismatches between the putative protospacer and the corresponding CRISPR spacer of *C. tyrobutyricum.*

Plasmid Construction

All the plasmids and primers used in this study are listed in Table 3 and Table 4, respectively. The Phanta Max Super-Fidelity DNA Polymerase (Vazyme Biotech Co., Ltd., Nanjing, China) was used for the PCR to amplify DNA fragments for cloning purposes. For the attempt to delete spo0A gene (CTK_RS09345) in *C. tyrobutyricum* using the Type II CRISPR-Cas9 and CRISPR-Cas9 nickase (nCas9) systems derived from *S. pyogenes*, the plasmid pYW34-BtgZI was chosen as the mother vector. This vector contains the Cas9 open reading frame (ORF) driven by the lactose inducible promoter and the chimeric gRNA sequence preceded by two BtgZI sites (for easy re-targeting purpose by inserting the small RNA (sCbei_5830) promoter along with the 20-nt guiding sequence). The vector pJZ23-Cas9 was constructed from pYW34-BtgZI through Gibson Assembly as follows. The erythromycin (Erm) marker and CAK1 replicon of pYW34-BtgZI were replaced with Cm marker and pBP1 replicon, respectively, through an in vitro double digestion with Cas9 nuclease following the procedure as described previously (Wang et al., 2016, ACS Synth. Biol. 5, 721-732). The Cm marker and the pBP1 replicon were amplified from pMTL82151. The TraJ component which is essential for the conjugation was also amplified from pMTL82151 and cloned into the ApaI restriction site of pYW34-BtgZI through Gibson Assembly, generating vector pJZ23-Cas9. To construct pJZ58-nCas9, the Plac-Cas9 expression cassette within pJZ23-Cas9 was replaced with the Plac-nCas9 expression cassette as follows. A partial fragment of the nCas9 ORF which contains the mutation (D10A) was obtained by PCR using plasmid pMJ841 (Addgene, Cambridge, Mass., USA) as the template. Then the partial fragment of nCas9 was fused with lactose inducible promoter (which was amplified from pYW34-BtgZI) through Splicing by Overlap Extension (SOE) PCR, yielding the Plac-nCas9 expression cassette. The Plac-nCas9 expression cassette was cloned into pJZ23-Cas9 by replacing the Plac-Cas9 fragment between ApaI and NheI restriction sites, generating pJZ58-nCas9.

Based on pJZ23-Cas9 and pJZ58-nCas9, the small RNA (sCbei_5830) promoter fused with the 20-nt guiding sequence (5'-GACATGCTATTGAAGTAGCG-3'; SEQ ID NO: 6) targeting on spo0A and two homology arms (~1 kb each) were cloned into the BtgZI and NotI sites, respectively, as described previously (Wang et al., 2017 Appl. Environ. Microbiol. 83, e00233-17), generating pJZ23-Cas9-spo0A and pJZ58-nCas9-spo0A.

In order to employ the CRISPR-AsCpf1 system derived from *Acidaminococcus* sp. BV3L6 to delete spo0A in *C. tyrobutyricum*, the plasmid pJZ60-AsCpf1-spo0A was constructed as follows. First, AsCpf1 was amplified from pDEST-hisMBP-AsCpf1-EC and fused with the lactose inducible promoter (amplified from pYW34-BtgZI) through SOE PCR, yielding the Plac-AsCpf1 expression cassette. The Plac-AsCpf1 expression cassette was then cloned into the NdeI restriction site of pMTL82151 with Gibson Assembly, yielding the plasmid pWH36-AsCpf1. Based on pWH36-AsCpf1, the small RNA (sCbei_5830) promoter fused with a synthetic CRISPR-AsCpf1 array and two homology arms (~1 kb each) were cloned into the BamHI site with Gibson Assembly, generating pJZ60-AsCpf1-spo0A. The synthetic CRISPR-AsCpf1 array was designed to contain two 20-nt direct repeat sequences (5'-TAATTTCTACTCTTGTAGAT-3'; SEQ ID NO: 7) separated by one 23-nt guide sequence (5'-CCGAGAGTAATCGTGCTTTCAGC-3'; SEQ ID NO: 8) targeting on the spo0A gene. The small RNA promoter was used to drive the expression of the CRISPR-AsCpf1 array (See Wang et al., 2016).

For the plasmid interference assay, the two primers (see the 'Plasmid interference assays' section in Table 4) for each plasmid (carrying the protospacer with 5' or 3' PAM) were first annealed, and then ligated into pMTL82151 which was pre-digested with EcoRI and BamHI. Plasmid pJZ69-leader-38spo0A was constructed through Gibson Assembly by cloning a synthetic CRISPR expression cassette and two homology arms (for spo0A deletion through homologous recombination) into the vector pMTL82151 between EcoRI and KpnI sites, and between KpnI and BamHI sites, respectively. The synthetic CRISPR expression cassette contained a 291 bp native CRISPR leader sequence, a 38-nt spo0A spacer1 sequence (5'-ATACCGTTTTCTTGCTCTCACTACTATTAGCTATATCA-3') flanked by two 30-nt direct repeat sequences (5'-GTTGAACCTTAACATGAGATGTATTTAAAT-3'; SEQ ID NO: 2) and a 342 bp terminator sequence which was found at the downstream of the endogenous CRISPR array of *C. tyrobutyricum*. The leader sequence, terminator sequence, upstream and downstream homology arms (~1 kb each) of spo0A were obtained by PCR using the genomic DNA (gDNA) of *C. tyrobutyricum* as the template (Table 4). Spacer and direct repeat sequences were included in the reverse primer for amplifying the leader sequence and the forward primer for amplifying the terminator. The synthetic CRISPR expression cassette was obtained by fusing the spacer and direct repeat sequences through SOE PCR. To construct pJZ74-Plac-38spo0A and pJZ76-Para-38spo0A, a lactose inducible promoter and an arabinose inducible promoter were used respectively to replace the native leader sequence in pJZ69-leader-38spo0A. The lactose inducible promoter and arabinose inducible promoter were amplified from the plasmid pYW34-BtgZI and the gDNA of *C. acetobutylicum* ATCC 824, respectively. Based on pJZ74-Plac-38spo0A, plasmid pJZ75-Plac-38spo0A was constructed by replacing the 38-nt spo0A spacer1 sequence with the 38-nt spo0A spacer2 sequence (5'-GCAACCATAGCTATAAATTCTGAATTTGTTGGTTTACC-3'; SEQ ID NO: 10) which targeted on another locus of the spo0A gene (Table 4). Plasmids pJZ74-Plac-10spo0A, pJZ74-Plac-20spo0A, pJZ74-Plac-30spo0A and pJZ74-Plac-50spo0A (for evaluating spacers of various lengths) were constructed by replacing the 38-nt spo0A spacer1 sequence in pJZ74-Plac-38spo0A with the 10-nt spacer1 (5'-ATACCGTTTT-3'; SEQ ID NO: 11), 20-nt spacer1 (5'-ATACCGTTTTCTTGCTCTCA-3'; SEQ ID NO: 12), 30-nt spacer1 (5'-ATACCGTTTTCTTGCTCTCACTACTATTAG-3'; SEQ ID NO: 13), and 50-nt spacer1 (5'-ATACCGTTTTCTTGCTCTCACTACTATTAGCTATATCATTATTAAACATT-3'; SEQ ID NO: 14), respectively.

For the double deletion of the spo0A gene and pyrF gene (CTK_RS12430), the plasmid pJZ77-Plac-30spo0A/30pyrF was constructed to contain the synthetic CRISPR expression cassette comprised of the lactose inducible promoter, the native terminator and a synthetic array sequence carrying two spacer sequences insulated by three 30-nt direct repeat sequences. The synthetic CRISPR expression cassette and four homology arms (for deleting the two genes respectively) were cloned through Gibson Assembly into pMTL82151 between EcoRI and KpnI sites, and between KpnI and BamHI sites, respectively. The 30-nt spacer1 targeting on spo0A and the 30-nt spacer3 (5'-TTGGATGTTCTTATAAGGACAAATACTCCT-3'; SEQ ID NO: 15) targeting on pyrF were used in pJZ77-Plac-30spo0A/30pyrF. The upstream and downstream homology arms for spo0A deletion (~300 bp each) and for pyrF deletion (~300 bp each) respectively were amplified using the gDNA of *C. tyrobutyricum* as template (Table 4). The plasmid pJZ77-Plac-30spo0A (30-nt spacer1, two arms of ~300 bp for each) for spo0A single deletion and the plasmid pJZ77-Plac-30pyrF (30-nt spacer3, two arms of ~300 bp for each) for pyrF single deletion were constructed as the control for the double deletion using the 'two-spacer' approach.

To delete the phosphotransacetylase/acetate kinase operon (pta-ack; CTK_RS08755-CTK_RS08750), plasmids pJZ86-Plac-34pta/ack was constructed by replacing the 38-nt spo0A spacer1 sequence in pJZ74-Plac-38spo0A with the 34-nt pta-ack spacer4 (5'-GATTGTGCTGTAAATCC-TGTACCTAATACTGAAC-3'; SEQ ID NO: 16). Upstream and downstream homology arms (~500 bp each; containing additional KpnI and BamHI recognition sequences in the middle) for pta-ack operon deletion were amplified using the gDNA of *C. tyrobutyricum* as template (Table 4) and cloned into pMTL82151 through Gibson Assembly between KpnI and BamHI sites. The adhE1 gene (CA_P0162) and adhE2 gene (CA_P0035) amplified from the total DNA of *C. acetobutylicum* ATCC 824 was inserted into the middle of the two homology arms of plasmid pJZ86-Plac-34pta/ack between the additional KpnI and BamHI sites, yielding pJZ86-Plac-34pta/ack(adhE1) and pJZ86-Plac-34pta/ack (adhE2), respectively. The constructions of plasmids pJZ95-Plac-34cat1, pJZ95-Plac-34cat1(adhE1) and pJZ95-Plac-34cat1(adhE2), used for cat1 gene (CTK_RS03145) deletion or replacement, were similar with plasmids pJZ86-Plac-34pta/ack, pJZ86-Plac-34pta/ack(adhE1) and pJZ86-Plac-34pta/ack(adhE2), respectively. The spacer used for targeting cat1 gene was 34-nt spacer5 (5'-CTTGTAGAAGATG-GATCAACCCTACAACTTGGTA-3'; SEQ ID NO: 4). To construct the plasmid-based adhE1 or adhE2 overexpression vectors, the promoter of cat1 gene was amplified from the gDNA of *C. tyrobutyricum* and cloned into pMTL82151 through Gibson Assembly between EcoRI and KpnI sites, generating plasmid pJZ98-Pcat1. Then adhE1 gene and adhE2 gene were cloned into plasmid pJZ98-Pcat1 through Gibson Assembly between BtgZI and EcoRI sites, yielding pJZ98-Pcat1-adhE1 and pJZ98-Pcat1-adhE2, respectively.

Transformation of *C. tyrobutyricum*

Plasmids used in this study were transformed into *C. tyrobutyricum* via conjugation following published protocols with modifications (Yu et al., 2012 Appl. Microbiol. Biotechnol. 93, 881-889). The donor strain *E. coli* CA434 carrying the recombinant plasmid was cultivated in LB medium supplemented with 30 μg/mL Cm and 50 μg/mL Kan. When the $OD_{600}$ reached 1.5-2.0, about 3 mL *E. coli* CA434 cells were centrifuged and washed twice (with 1 mL fresh LB medium for each wash) to remove the antibiotics. The obtained donor cells were then mixed with 0.4 mL of the recipient culture of *C. tyrobutyricum* (which had an $OD_{600}$ of 2.0-3.0 after an overnight growth in TGY medium). The cell mixture was spotted onto a well-dried TGY agar plate and incubated in the anaerobic chamber at 37° C. for mating purposes. After 24 hours, the transconjugants were collected by washing them off the conjugation plate using one mL of TGY medium, and were then spread onto TGY plates containing 15 g/mL Tm and 250 μg/mL D-cycloserine (for eliminating the residual *E. coli* CA434 donor cells). Transformant colonies could be generally observed after 48-96 h of incubation.

Mutant Screening

The screening of mutants was performed following the protocol as described previously with modifications (see Wang et al., 2017). The transformant colonies of *C. tyrobutyricum* were picked and inoculated into TGY liquid medium with addition of 15 g/mL Tm (TGYT). The obtained cultures were then diluted serially and spread onto TGY plates supplemented with 40 mM lactose and 15 μg/mL Tm (TGYLT). The plates were incubated anaerobically at 37° C. until colonies were observed. Colony PCR (cPCR) was then performed to screen the putative mutants. When the deletion of pyrF is involved, 20 μg/mL uracil was added into TGYLT medium (TGYLTU) to support the growth of ΔpyrF strain. When shorter spacer sequence (30 bp) and shorter homology arms (~300 bp) were used for the gene deletion, a series of subculturing (1% v/v inoculum) was carried out using either TGYLT or TGYLTU liquid medium to enrich the desirable homologous recombination, before plating the culture onto the TGYLT or TGYLTU plates for selection.

Batch Fermentation

Batch fermentations with various *C. tyrobutyricum* strains were carried out in 500 mL bioreactors (GS-MFC, Shanghai Gu Xin biological technology Co., Shanghai, China) with a 250 mL working volume. The fermentation medium used in this study was prepared as described previously (Zhang et al., 2017, Biotechnol. Bioeng. 114, 1428-1437), which comprised (per liter of distilled water): 110 g glucose; 5 g yeast extract; 5 g tryptone; 3 g $(NH_4)_2SO_4$; 1.5 g $K_2HPO_4$; 0.6 g $MgSO_4.7H_2O$; 0.03 g $FeSO_4.7H_2O$, and 1 g L-cysteine. The *C. tyrobutyricum* strain was first incubated anaerobically at 37° C. in TGY medium until $OD_{600}$ reached 1.5 and then the active seed culture was inoculated into the bioreactor at a volume ratio of 5%. The fermentation was carried out at pH 6.0 under various temperatures (20, 25, 30, 37° C.). Batch fermentations with *C. beijerinckii* NCIMB 8052 and *C. saccharoperbutylacetonicum* N1-4 under various temperatures (20, 25, 30, 35° C.) were carried out as described previously. Samples were taken every 12 hours for the analysis.

Analytical Methods

Cell growth was determined by measuring the optical density at 600 nm ($OD_{600}$) using a cell density meter (Ultrospec 10, Biochrom Ltd., Cambridge, England). Glucose, acetate, ethanol, butyrate and butanol concentrations in the fermentation broth were analyzed using an HPLC (Agilent 1260 series, Agilent Technologies, Santa Clara, Calif., USA) equipped with a refractive index detector (RID) and an Aminex HPX-87H column (Bio-Rad, Hercules, Calif., USA). 5 mM $H_2SO_4$ was used as the mobile phase a flow rate of 0.6 mL/min at 25° C.

Results

Attempts of Genome Editing in *C. tyrobutyricum* with CRISPR-Cas9/Cpf1 Systems

Figure 3C:
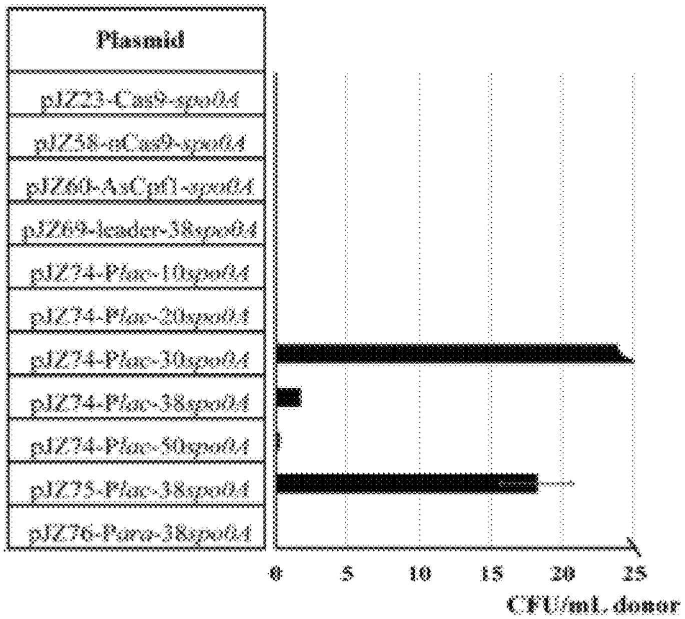

Recently, genome editing tools have been developed for several Gram-positive bacteria based on the Type II CRISPR-Cas9/nCas9 system derived from *S. pyogenes*, and various Type V CRISPR-Cpf1 systems. These systems were first considered by applicants for genome engineering in *C. tyrobutyricum*. The spo0A gene which is the master regulator for sporulation was selected as the target gene to delete. To abate the strong toxicity of the nuclease/nickase, we constructed CRISPR-Cas9/nCas9/AsCpf1 based vectors by placing the Cas9/nCas9/AsCpf1 encoding gene under the control of a lactose inducible promoter, whereas the gRNA/crRNA were expressed from the constitutive small RNA promoter from *C. beijerinckii*. (Wang et al., 2016) In addition, the homology arms for spo0A deletion through homologous recombination were inserted into the same plasmid (Wang et al., 2016). The resultant plasmid (pJZ23-Cas9-spo0A, pJZ58-nCas9-spo0A and pJZ60-AsCpf1- spo0A, respectively; FIG. 3A) was attempted to be transformed into *C. tyrobutyricum*. Although numerous attempts were implemented, no transformant could be obtained (FIG. 3C). This indicated that, due to the high toxicity of the heterologous nuclease/nickase and the limited transformation efficiency of *C. tyrobutyricum*, the genome editing is difficult to be realized in this microorganism with the CRISPR-Cas9/nCas9/Cpf1 system. It has been reported that the endogenous CRISPR-Cas system within bacteria and archaea can be harnessed for genome editing for the host microorganism (Li et al., 2015 Nucleic Acids Res. 44, e34). From the genome sequence, we noticed that *C. tyrobutyricum* possesses a Type I-B CRISPR-Cas system. Therefore, we next turned to exploit this endogenous CRISPR-Cas system for genome editing in *C. tyrobutyricum.*

In Silico Analysis of the Type I-B CRISPR-Cas System of *C. tyrobutyricum*

Based on the genome sequence, two CRISPR arrays were identified located at two different loci within the *C. tyrobutyricum* genome. The first CRISPR array (Array1) contains 17 spacers (length: 34-38 nt) flanked by direct repeat sequences of 30 nt (5'-ATTGAACCTTAACATGAGATGTATTTAAAT-3'; SEQ ID NO: 18). However, no putative Cas-encoding gene was found at the upstream or downstream of Array1. The second CRISPR array (Array2) was comprised of eight spacers (length: 34-38 nt) flanked by direct repeat sequences of 30 nt (5'-GTTGAACCTTAACATGAGATGTATTTAAAT-3'; SEQ ID NO: 2) which is only one nucleotide different from that of Array1). A core cas gene operon (cas6-cas8b-cas7-cas5-cas3-cas4-cas1-cas2) was found at the upstream of Array2, indicating that this CRISPR-Cas system belongs to the Type I-B subtype (FIG. 1A).

Figure 1B:

The CRISPR-Cas system is known as an immune system, and its spacer sequences are typically derived from the invading genetic elements during the 'adaptation' stage. Therefore, we set out to analyze all the 25 spacer sequences specified in Array1 and Array2 using Nucleotide BLAST, aiming to elucidate whether any spacer sequence matches the putative invading DNA elements, including phage (prophage), plasmid, transposon, and integrase. In order to determine the putative protospacers, a mismatch of less than 15% (5/34 mismatching nucleotides or less) was defined (Shariat et al., 2015). Among all the 25 spacers in the CRISPR-Cas system of *C. tyrobutyricum*, only one spacer sequence (the $17^{th}$ spacer within Array 1, Array1-17: 5'-TGGTATCACCAACTTTTGTCCAGGATATATGAGGTT-3'; SEQ ID NO: 19) hit (with five mismatches) the putative protospacers found in phage sequence from *C. thermocellum* and prophage sequence from *Geobacillus thermoglucosidasius* (FIG. 1B).

Identification of Protospacer Adjacent Motif (PAM) Sequences

A plasmid transformation interference assay was carried out to test the activity of the Type I-B CRISPR-Cas system of *C. tyrobutyricum* and meanwhile identify the putative PAM sequences. The plasmid employed in interference assay contains a protospacer for the DNA targeting purpose and a 5-nt putative PAM sequence located at the 5'- or 3'-end of the protospacer which is essential for the recognition by the Type I CRISPR-Cas system (Table 1). Though the spacer Array1-17 was the only spacer found to match the invading DNA elements, there was no adjacent Cas-encoding genes associated with Array1 discovered. Therefore, additionally we decided to employ another spacer (Array2-1: GCATTCAGACTTGCAACTGTAACTCCCTAGTACTCCCC; SEQ ID NO: 21) derived from Array2 as the protospacer for the plasmid interference purpose. The 5-nt sequences derived from the upstream or downstream of identified putative protospacers were tested as putative PAM sequences (FIG. 1B & Table 1). Our in silico analysis revealed that the *C. tyrobutyricum* CRISPR array possessed high homology to the CRISPR array of *C. pasteurianum*, for both the leader and direct repeat sequences (FIGS. 6A & 6B). Therefore, we hypothesized that the CRISPR-Cas system of *C. tyrobutyricum* may share the same or similar PAM with that of *C. pasteurianum*. Hence, the PAM sequences for *C. pasteurianum* Type I-B CRISPR-Cas system were also employed in the plasmid interference assay (Table 1). Altogether, 14 interference plasmids were constructed by combining different protospacer and PAMs (Table 1). Since both a protospacer and PAM sequence have been included on the interference plasmid, there would be no transformants (the specific plasmid is cleaved and eliminated; we define this as the 'interference response') if the CRISPR-Cas system is functional with a particular combination of the protospacer and PAM. As shown in Table 1, no matter what PAM sequences were employed, there was no interference response observed when the protospacer Array1-17 was used. This result suggests that Array1 which does not have an adjacent cas gene operon may be silent in the genome of *C. tyrobutyricum*, or it was possibly derived from a gene transfer event which was unrelated to the development of the CRISPR-Cas immunity system in *C. tyrobutyricum*. While combinations of protospacer Array2-1 with 5' adjacent PAM sequences 5'-CATCA-3' or 5'-TTTCA-3', derived from *C. tyrobutyricum* and *C. pasteurianum* respectively, successfully triggered the interference response (Table 1). Plasmids contained combinations of Array2-1 (as the protospacer) and other PAMs were transformed efficiently into *C. tyrobutyricum* (Table 1). These results indicated that Array2 along with the associated core cas gene operon in *C. tyrobutyricum* is active and highly functional. Furthermore, the specific PAM sequence located at the 5'-end of the protospacer is essential for the target recognition of Cas proteins.

Figure 2A:
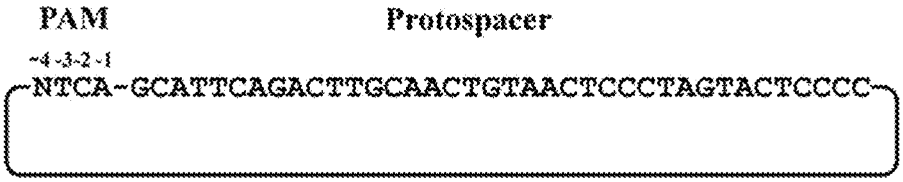
FIGS. 2A & 2B Identification of protospacer adjacent motif (PAM) sequences of the Type I-B CRISPR-Cas system in *C. tyrobutyricum*.
Figure 2B:
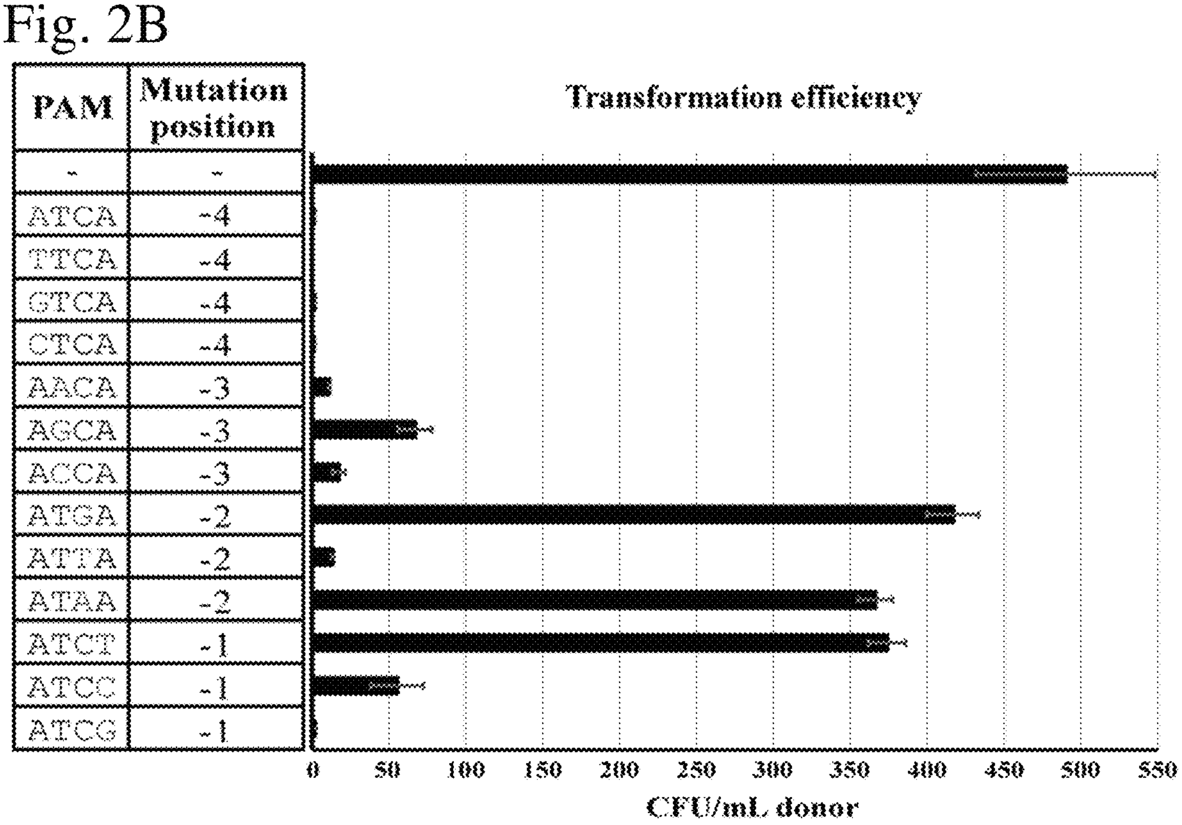

We used 5-nt PAM sequences in the plasmid transformation interference assay on the basis that most identified PAMs within various microorganisms vary between 2-5 nt (Shah et al., 2013). However, it is noteworthy that the two functional PAM sequences contain a conserved 3-nt sequence 5'-TCA-3' which may play the critical role for the target recognition for *C. tyrobutyricum* Type I-B CRISPR-Cas system. To test our hypothesis, various PAMs (5'-NTCA-3' with point mutations at different positions) built upon 5'-TCA-3' were systematically evaluated for their functionality (FIG. 2). As shown in FIG. 2B, significant differences in the transformation efficiency were observed with plasmids containing different PAMs (along with Array2-1 as the protospacer). All the plasmids contained point mutations at position −4 triggered the interference response, suggesting that the first three nucleotides (5'-TCA-3') encompass the core PAM sequence. When 'T' located at position −3 was mutated, only slightly increased transformation efficiency was obtained, indicating that the nucleotide on position −3 had a minor effect on target recognition. Nevertheless, high transformation efficiency (comparable to the control plasmid pMTL82151) was observed when 'C' located at position −2 was mutated to 'G' or 'A' or 'A' located at position −1 was mutated to 'T'. The transformation efficiency was slightly increased (compared to that with 5'-NTCA-3') when 'A' located at position −1 was mutated to 'C', while 'TCG' kept the similar level of transformation efficiency with 5'-NTCA-3'. These data demonstrated that, for the appropriate function of the PAM sequence, pyrimidine nucleotides ('C' and 'T'), rather than purine nucleotides ('G' and 'A'), are more preferable at the position −2, and conversely, purine nucleotides are better options than pyrimidine nucleotides at the position −1. Overall, 3-nt sequences 5'-TCA-3' (TCA) and 5'-TCG-3' (TCG) (also written as TCR collectively for both) which led to an approximately 1,000-fold drop in plasmid transformation efficiency (compared to the control plasmid pMTL82151, FIG. 2B) were concluded to be the functional PAM sequences of the Type I-B CRISPR-Cas system in *C. tyrobutyricum*.

thetic CRISPR expression cassette (SEQ ID NO: 4) comprising the native CRISPR leader (SEQ ID NO: 1) and terminator sequences (SEQ ID NO: 3) were used to drive the transcription of synthetic CRISPR array which contained the 38-nt spo0A spacer1 (SEQ ID NO: 9) (flanked by 30-nt direct repeat sequences (SEQ ID NO: 2). Conjugation was carried out. However, no transformants were obtained with pJZ69-leader-38spo0A, although the expected transformation efficiency was obtained with pMTL82151 as the control. Many attempts have been conducted, and the results were consistently the same (data not shown).

TABLE 1

Effect of different combinations of protospacers and PAM sequences on the transformation efficiency.

| Plasmid | 5' PAM | Protospacer[a] | 3' PAM | Transform efficiency ($\times 10^2$ CFU/mL donor)[b] |
|---|---|---|---|---|
| pMTL82151 | | | | 4.9 ± 0.6 |
| pIF-1 | CATCT | TGGTATCACCAACTTTTGTCCAGGATATATGAGGTT (SEQ ID NO: 19) | | 4.2 ± 0.8 |
| pIF-2 | CATCA | TGGTATCACCAACTTTTGTCCAGGATATATGAGGTT (SEQ ID NO: 19) | | 3.7 ± 0.4 |
| pIF-3 | | TGGTATCACCAACTTTTGTCCAGGATATATGAGGTT (SEQ ID NO: 19) | AGGAT | 4.8 ± 0.1 |
| pIF-4 | | TGGTATCACCAACTTTTGTCCAGGATATATGAGGTT (SEQ ID NO: 19) | CGGAT | 4.2 ± 0.7 |
| pIF-5 | AATTG | TGGTATCACCAACTTTTGTCCAGGATATATGAGGTT (SEQ ID NO: 19) | | 3.9 ± 0.5 |
| pIF-6 | TTTCA | TGGTATCACCAACTTTTGTCCAGGATATATGAGGTT (SEQ ID NO: 19) | | 3.3 ± 0.4 |
| pIF-7 | TATCT | TGGTATCACCAACTTTTGTCCAGGATATATGAGGTT (SEQ ID NO: 19) | | 5.1 ± 0.2 |
| pIF-8 | CATCT | GCATTCAGACTTGCAACTGTAACTCCCTAGTACTCCCC (SEQ ID NO: 22) | | 3.8 ± 0.3 |
| pIF-9 | CATCA | GCATTCAGACTTGCAACTGTAACTCCCTAGTACTCCCC (SEQ ID NO: 22) | | 0 ± 0 |
| pIF-10 | | GCATTCAGACTTGCAACTGTAACTCCCTAGTACTCCCC (SEQ ID NO: 22) | AGGAT | 3.5 ± 0.9 |
| pIF-11 | | GCATTCAGACTTGCAACTGTAACTCCCTAGTACTCCCC (SEQ ID NO: 22) | CGGAT | 4.1 ± 0.1 |
| pIF-12 | AATTG | GCATTCAGACTTGCAACTGTAACTCCCTAGTACTCCCC (SEQ ID NO: 22) | | 4.0 ± 0.7 |
| pIF-13 | TTTCA | GCATTCAGACTTGCAACTGTAACTCCCTAGTACTCCCC (SEQ ID NO: 22) | | 0 ± 0 |

[a]Two kinds of protospacers were used here: Array1-17 and Array2-1).
[b]Values are average ± standard deviation based on at least two independent replicates.

Development of an Inducible CRISPR-Cas System for Genome Editing in *C. tyrobutyricum*

Figure 3D:
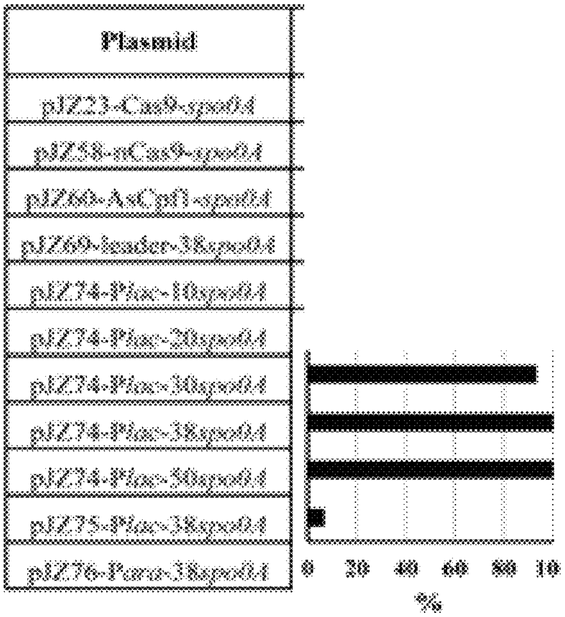

After establishing that the endogenous Type I-B CRISPR-Cas system of *C. tyrobutyricum* was functional and had high interference activity against plasmids possessing proper protospacer and PAM sequences, we then attempted to engineer this system to be a genome editing tool for *C. tyrobutyricum*. Two parts are required for such a system: 1) a synthetic CRISPR expression cassette, containing a spacer targeting on the specific genome sequence; 2) gene editing cassette, comprised of a pair of homology arms to achieve homologous recombination (FIG. 3A). The spo0A gene was selected as the first target gene to be deleted. The 816 bp spo0A ORF contains a total of 28 potential PAMs (TCR) including 24 TCA and 4 TCG. One of the PAM (TCA) along with its downstream protospacer sequence (38-nt spo0A spacer1) was selected as the target site. Plasmid pJZ69-leader-38spo0A, comprised of a synthetic CRISPR expression cassette and a spo0A editing cassette (upstream and downstream homology arms, ~1 kb each), was constructed to delete the spo0A gene in *C. tyrobutyricum*. In the syn- Therefore, even with the endogenous CRISPR-Cas system, the instant expression could be highly toxic to the cells and thus no transformants could be obtained. Generally, the leader sequence of the CRISPR array contains a promoter for CRISPR array transcription and a regulatory signal for the uptake of new spacer-repeat elements. In this study, however, for the genome editing purposes, only the promoter function of the leader sequence is needed. In order to reduce the toxicity of endogenous CRISPR-Cas system, a lactose inducible promoter and an arabinose inducible promoter were evaluated for the transcription of the synthetic CRISPR array in place of the native leader sequence (FIGS. 3A & B). The resultant plasmids pJZ74-Plac-38spo0A and pJZ76-Para-38spo0A were transformed into *C. tyrobutyricum*. Transformants were generated with pJZ74-Plac-38spo0A, with an overall transformation efficiency of 1.7 CFU/mL donor (FIG. 3C); while the transformation with pJZ76-Para-38spo0A failed, suggesting that the arabinose inducible promoter was less stringent than the lactose inducible promoter for the expression of the CRISPR array in *C. tyrobutyricum* (FIG. 3C). As a control (or as a means to further confirm the appropriate PAM sequence), a 38-nt spo0A spacer2 (corresponding PAM: TCT) was employed to replace the 38-nt spo0A spacer1 in pJZ74-Plac-38spo0A, generating plasmid pJZ75-Plac-38spo0A. Results demonstrated that the transformation efficiency with pJZ75-Plac-38spo0A (~18.2 CFU/mL donor) increased more than an order of magnitude compared to that with pJZ74-Plac-38spo0A (FIG. 3C). The obtained transformants (with either pJZ74-Plac-38spo0A or pJZ75-Plac-38spo0A) were cultivated in TGYT medium, and then spread onto TGYLT plates to induce the expression of the synthetic CRISPR array. Colony PCR was carried out with randomly picked colonies to screen the spo0A deletion mutants. Results showed that one out of fifteen (6.7%) of the tested colonies was spo0A deletion mutant (Δspo0A) from the transformants with pJZ75-Plac-38spo0A (FIG. 3D). While all tested colonies were Δspo0A mutants from the transformants with pJZ74-Plac-38spo0A, representing an editing efficiency of 100% (FIG. 3D). These results confirmed our above conclusion concerning the PAM sequence: the targeting efficiency of TCA is much higher than TCT. The Δspo0A mutant was further verified by Sanger sequencing (data not shown). Collectively, we proved that with the inducible endogenous CRISPR-Cas system, efficient genome editing could be achieved in *C. tyrobutyricum.*

Effects of Spacer Length on Transformation Efficiency and Genome Editing Efficiency In the *C. tyrobutyricum* genome, a total of 25 spacer sequences were identified in Array1 and Array2 with lengths ranging from 34 to 38 nt. In order to mimic the feature of the native Type I-B CRISPR array, the 38-nt spo0A spacer1 was employed to develop the genome editing platform for the deletion of spo0A. However, it is reasonable to question whether the length of the spacer has an effect on the transformation efficiency and genome editing efficiency of the CRISPR-Cas genome engineering platform. To answer this question, we replaced the 38-nt spo0A spacer1 in plasmid pJZ74-Plac-38spo0A with 10 nt, 20 nt, 30 nt, and 50 nt of spo0A spacer1 (while the PAM sequence TCA was kept the same), yielding pJZ74-Plac-10spo0A, pJZ74-Plac-20spo0A, pJZ74-Plac-30spo0A, and pJZ74-Plac-50spo0A, respectively (FIG. 3B). Surprisingly, no transformant was obtained after several attempts with pJZ74-Plac-10spo0A or pJZ74-Plac-20spo0A. This might be because the shorter spacer sequences (<20 nt) led to severe off-target effects which killed the host cells (FIG. 3C). However, when 30-nt, 38-nt and 50-nt spacers were used, transformation efficiencies of 103.0 CFU/mL donor, 1.7 CFU/mL donor and 0.2 CFU/mL donor were obtained, respectively (FIG. 3C). The longer spacers can bind more tightly to the target and thus increase the self-targeting activity of the endogenous CRISPR-Cas system, which may contribute to the decreased transformation efficiency. The genome editing efficiency was also assessed for the transformants obtained with pJZ74-Plac-30spo0A, pJZ74-Plac-38spo0A or pJZ74-Plac-50spo0A. Interestingly, colonies of various sizes were observed for the transformants harboring pJZ74-Plac-30spo0A on the TGYLT plates, while the colonies from the other two transformants appeared homogeneous in sizes. Large and small colonies of the transformant harboring pJZ74-Plac-30spo0A were picked separately to screen for the Δspo0A mutant, and editing efficiencies of 93.3% and 13.3% were obtained, respectively. The different genome editing efficiency for large and small colonies might be due to the low self-targeting activity of the endogenous CRISPR-Cas system when 30-nt spacer was employed. In this case, some of the host cells could survive from the selection of the endogenous CRISPR-Cas system, but their growth was still inhibited. Most of the observed small colonies were wild type cells with growth inhibited, whereas most of the large colonies were mutant cells without growth interference because their target site for the CRISPR-Cas system had been eliminated. On the other hand, the editing efficiencies of transformants obtained with pJZ74-Plac-38spo0A or pJZ74-Plac-50spo0A were both 100% (FIG. 3D).

Multiplex Genome Engineering

Figure 4A:
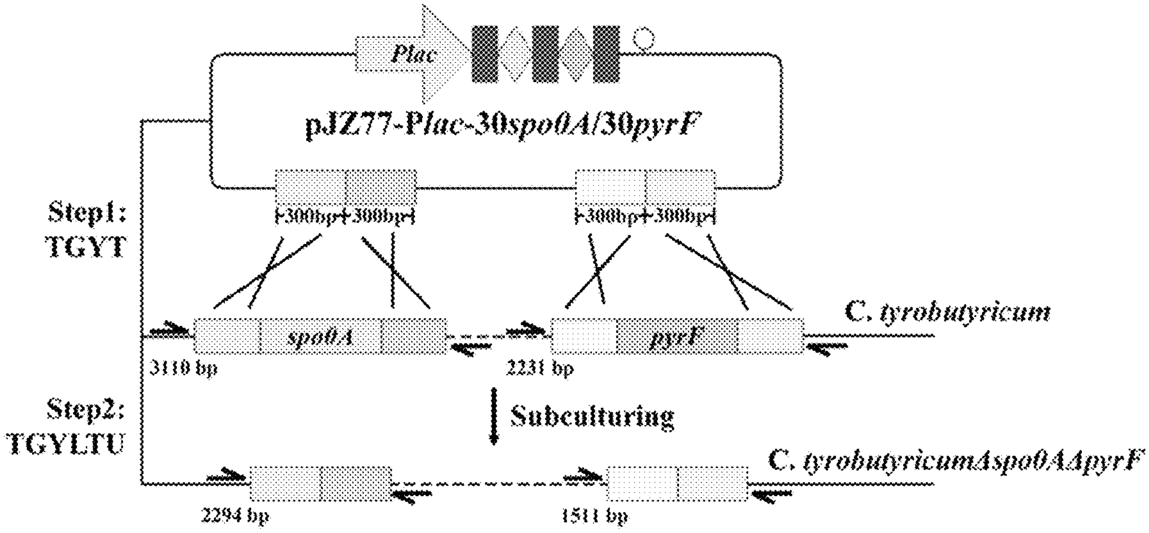
FIGS. 4A-4C: Multiplex gene editing in *C. tyrobutyricum* using the inducible endogenous Type I-B CRISPR-Cas system.
Figure 4B:
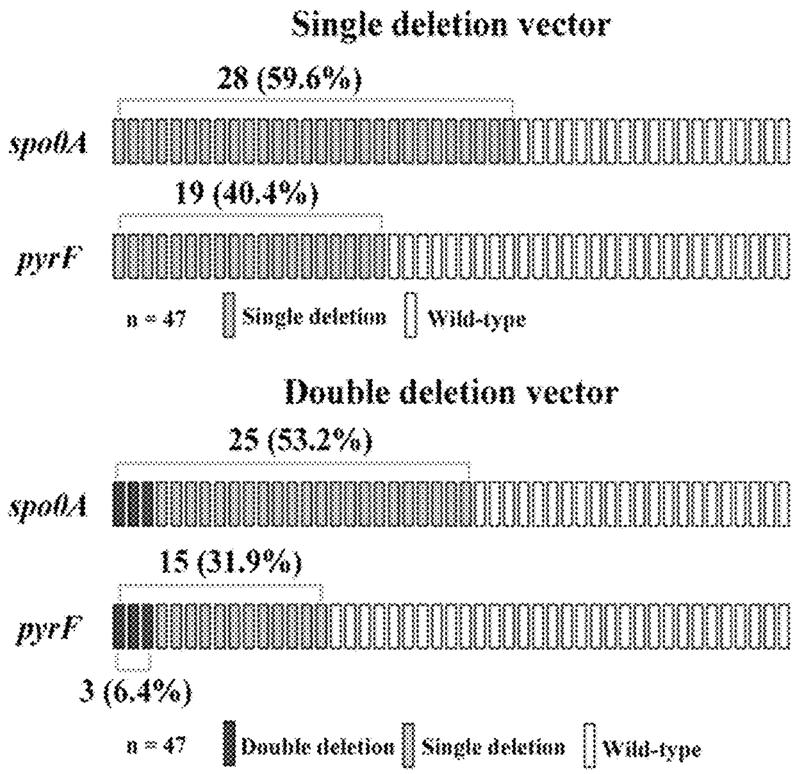
Figure 4C:
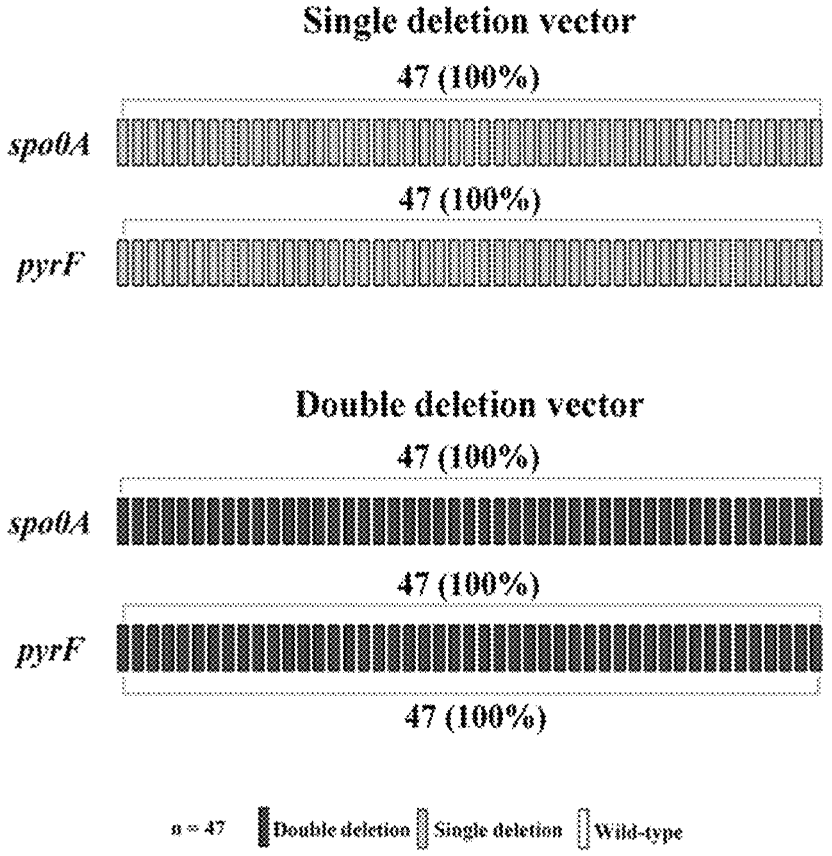

As described above, single gene deletion was achieved with high efficiency using the inducible endogenous CRISPR-Cas system. Here, we further explored this system for multiplex genome editing in *C. tyrobutyricum*. The pyrF gene encoding the enzyme orotidine 5-phosphate decarboxylase (involved in the de novo pyrimidine biosynthesis) together with the spo0A gene were selected as targets to delete. In order to have the CRISPR-Cas system target onto two loci at the same time, we inserted two spacers targeting on spo0A and pyrF respectively into the same CRISPR array insulated by three direct repeats (FIG. 4A). Considering that the longer spacer is more toxic to the host cells as we demonstrated above, 30 nt was used for both spacers (spo0A spacer1 and pyrF spacer3). In addition, as we noticed that, with the increase of the plasmid size, the transformation efficiency decreases dramatically (especially when the vector size >10 kb; data not shown), we used shorter homology arms for the deletion of both genes (two homology arms for the deletion of each gene, with the length of each arm is ~300 bp), to keep the final vector size <9 kb (FIG. 4A). Control plasmids pJZ77-Plac-30spo0A and pJZ77-Plac-30pyrF were also constructed for deleting spo0A and pyrF individually by using the same corresponding modules (spacer and homology arms) in pJZ77-Plac-30spo0A/30pyrF for deleting spo0A and pyrF, respectively. The three plasmids were successfully transformed into *C. tyrobutyricum*, and the resulting transformants were then spread onto TGYLTU plates. However, no mutant was detected (47 colonies from each transformant were screened with cPCR) for any of the three transformants, which was not surprising considering the reduced editing efficiency when shorter spacers and homology arms were used. In order to enrich the desirable homologous recombination, a series of subculturing was performed in TGYLTU liquid medium. Then mutant screening was performed with cPCR for the $8^{th}$ and $15^{th}$ generations of the subculture. For the $8^{th}$ generation, for spo0A and pyrF deletion respectively, editing efficiencies of 59.6% and 40.4% were obtained with the one-spacer approach (using pJZ77-Plac-30spo0A and pJZ77-Plac-30pyrF, respectively), while editing efficiencies of 53.2% and 31.9% were obtained with the two-spacer approach (using pJZ77-Plac-30spo0A/30pyrF) (FIG. 4B). In addition, double deletion was also detected with the two-spacer approach, but at a much lower rate (6.4%) (FIG. 4B). For the $15^{th}$ generation, up to 100% editing efficiencies were observed for spo0A and pyrF deletion with both one-spacer and two-spacer approaches, which meant that as high as 100% editing efficiency for the double deletion was also achieved with the two-spacer approach (FIG. 4C).

Engineered *C. tyrobutyricum* for Butanol Production

Figure 5:
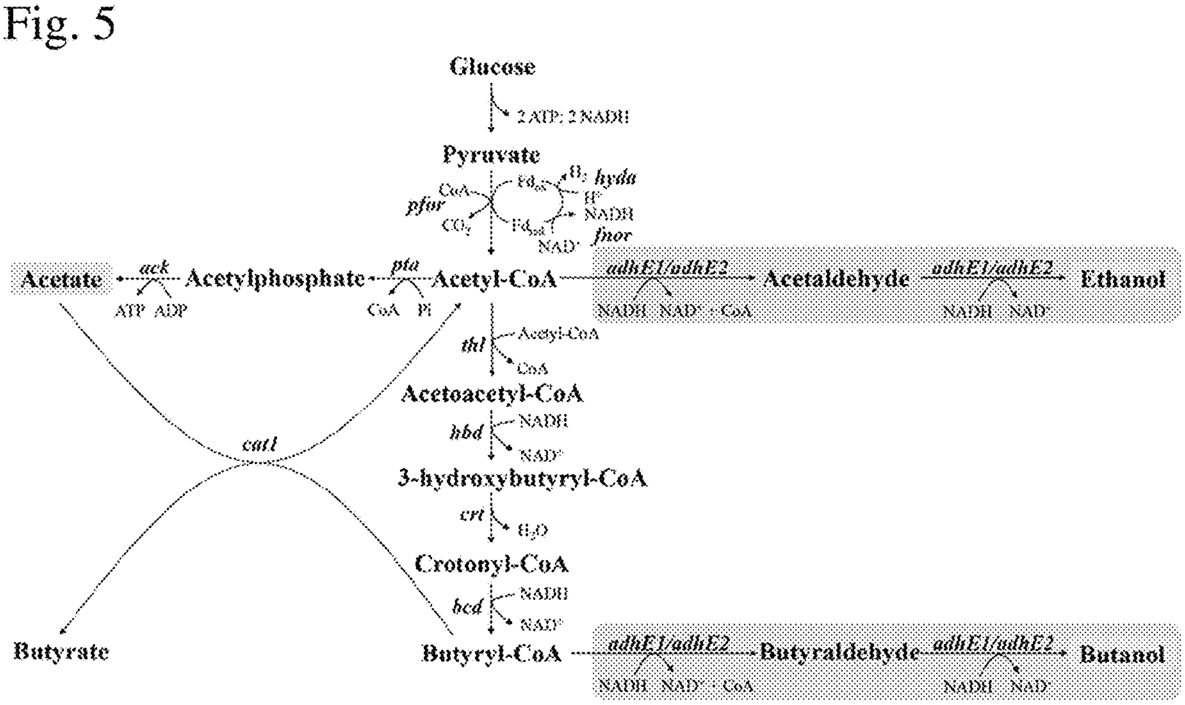
FIG. 5 provides a schematic diagram of the metabolic pathway of Δcat1::adhE1 and Δcat1::adhE2 mutants. The major products of the two mutants are ethanol and butanol and the biosynthesis pathways which are absent in the wild type strain are shown in grey boxes. The butyrate biosynthesis pathway which is disrupted from the wild type strain is shown with dotted lines. Key genes in the pathway: pfor, pyruvate::ferredoxin oxidoreductase; hyda, hydrogenase; fnor, ferredoxin $NAD^+$ oxidoreductase; pta, phosphotransacetylase; ack, acetate kinase; thl, thiolase; hbd, beta-hydroxybutyryl-CoA dehydrogenase; crt, crotonase; bcd, butyryl-CoA dehydrogenase; cat1, butyrate:acetate coenzyme A transferase; adhE1/adhE2, aldehyde-alcohol dehydrogenase.

*C. tyrobutyricum* is a hyper-butyrate producer, indicating that the metabolic pathway from glucose to butyryl-CoA is highly favorable (FIG. 5). Therefore, using the high efficient endogenous CRISPR-Cas system, we attempted to engineer the *C. tyrobutyricum* for hyper-butanol production. Two aldehyde/alcohol dehydrogenase genes (adhE1 and adhE2) which can convert butyryl-CoA to butanol were chosen to introduce into *C. tyrobutyricum*. In order to drive more metabolic flux towards C4 products, the pta-ack operon which was responsible for acetate formation was initially selected to be deleted or replaced by adhE1/adhE2 (FIG. 5). However, none of the attempts was successful (data not shown), suggesting that the pta-ack operon was vital for *C. tyrobutyricum* metabolism and thus cannot be deleted.

Figure 7A:
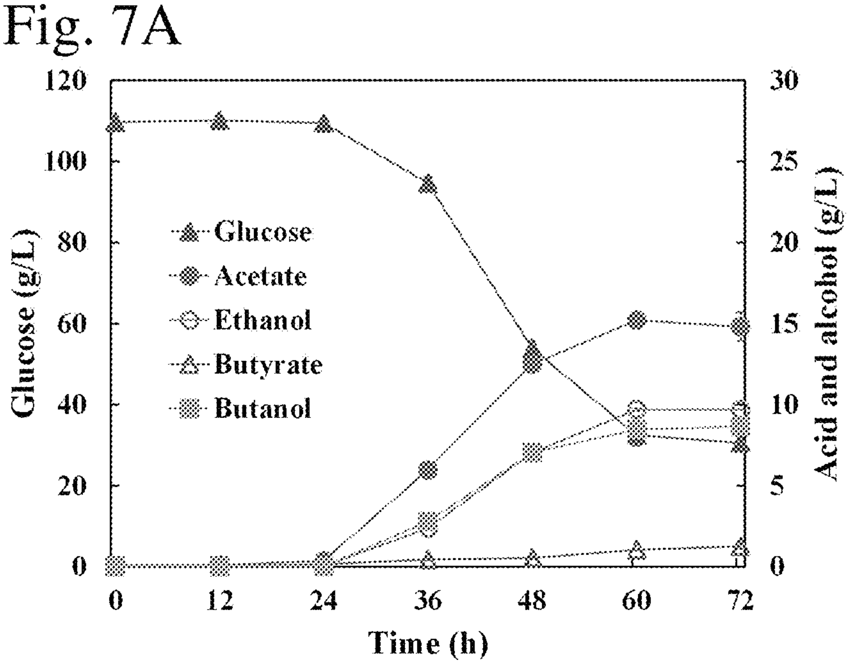
FIGS. 7A-7E: Fermentation profiles of *C. tyrobutyricum* WT(pJZ98-Pcat1-adhE1) and mutant Δcat1::adhE1 strains. Graphs are provided demonstrating the amount of glucose (▲), acetate (●), ethanol (○), butyrate (Δ) and butanol (■) detected over time when *C. tyrobutyricum* strains are cultured under different temperatures, using glucose as a carbon source.
Figure 7B:
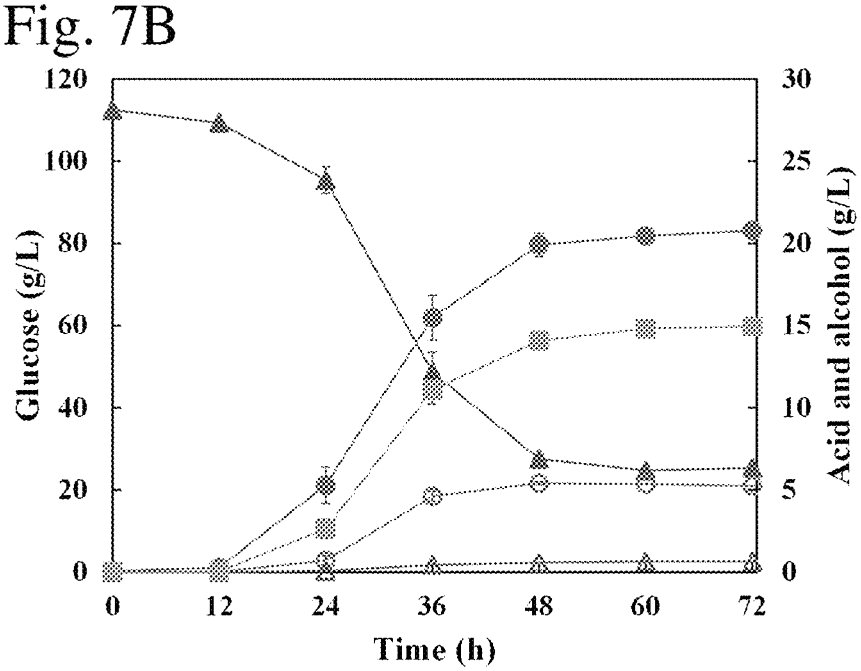
Figure 7C:
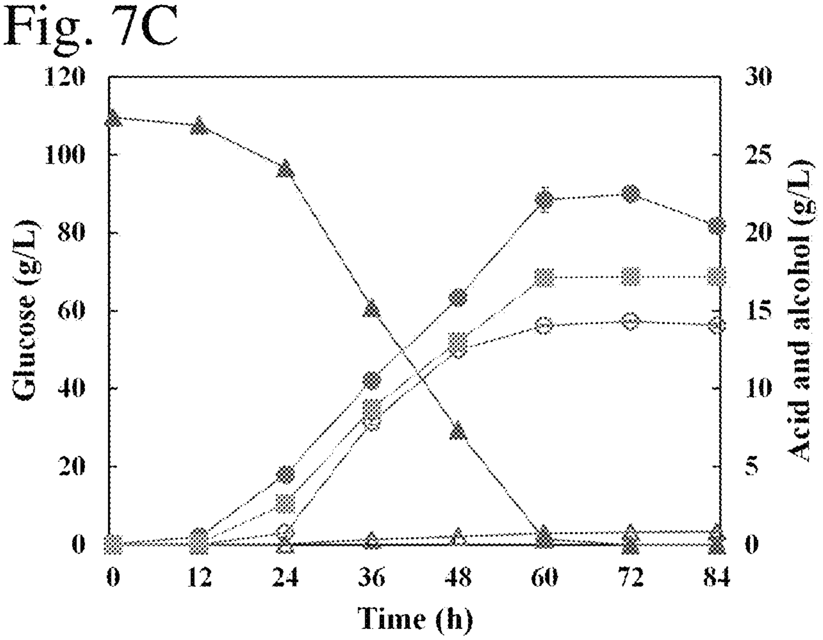
Figure 7D:
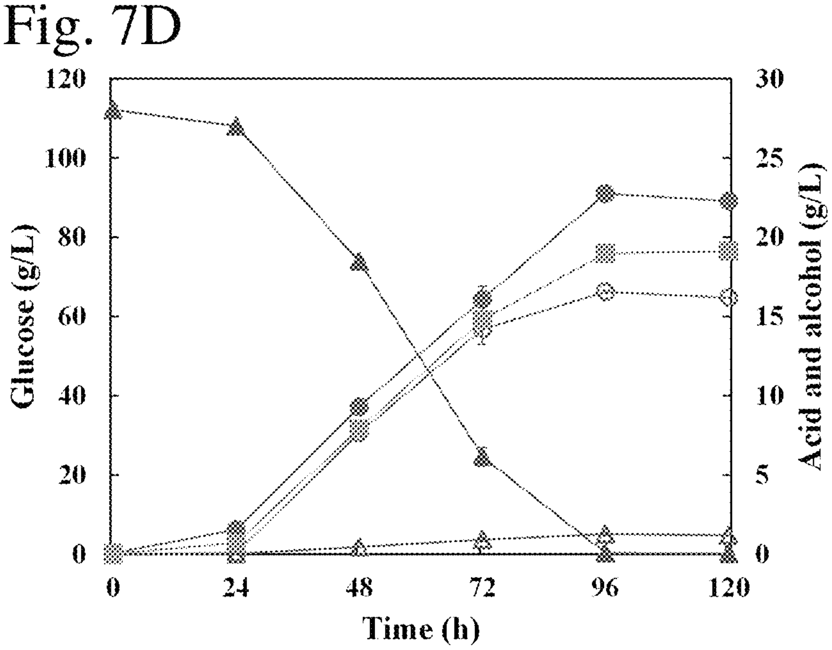
Figure 7E:
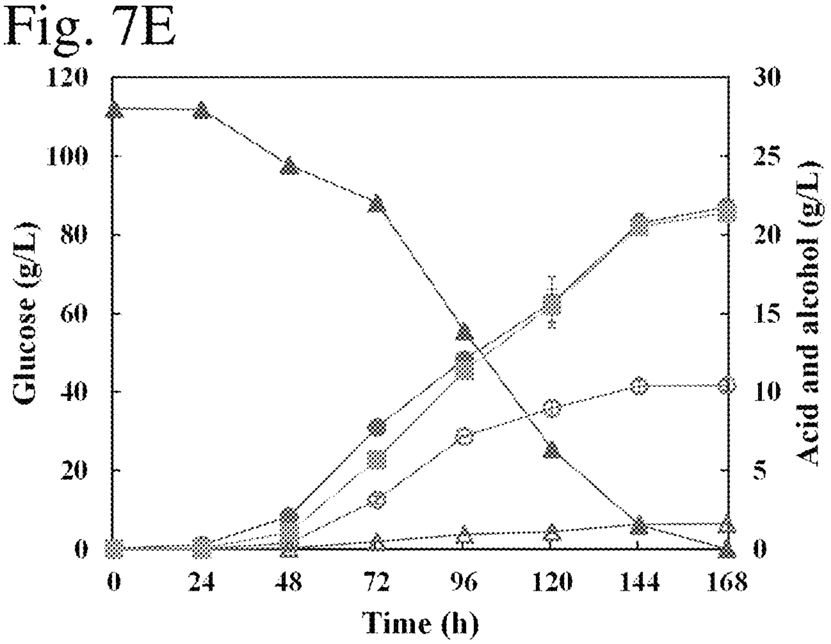
Figure 8A:
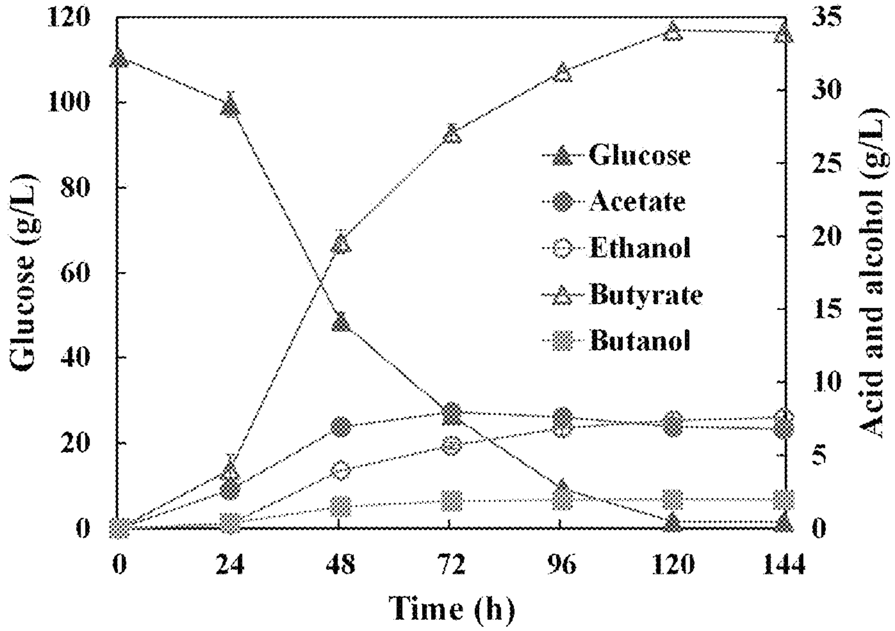
FIG. 8A-8E: Fermentation profiles of *C. tyrobutyricum* WT(pJZ98-Pcat1-adhE1) and mutant Δcat1::adhE2 strains. Graphs are provided demonstrating the amount of glucose (▲), acetate (●), ethanol (○), butyrate (Δ) and butanol (■) detected over time when *C. tyrobutyricum* strains are cultured under different temperatures, using glucose as a carbon source.
Figure 8B:
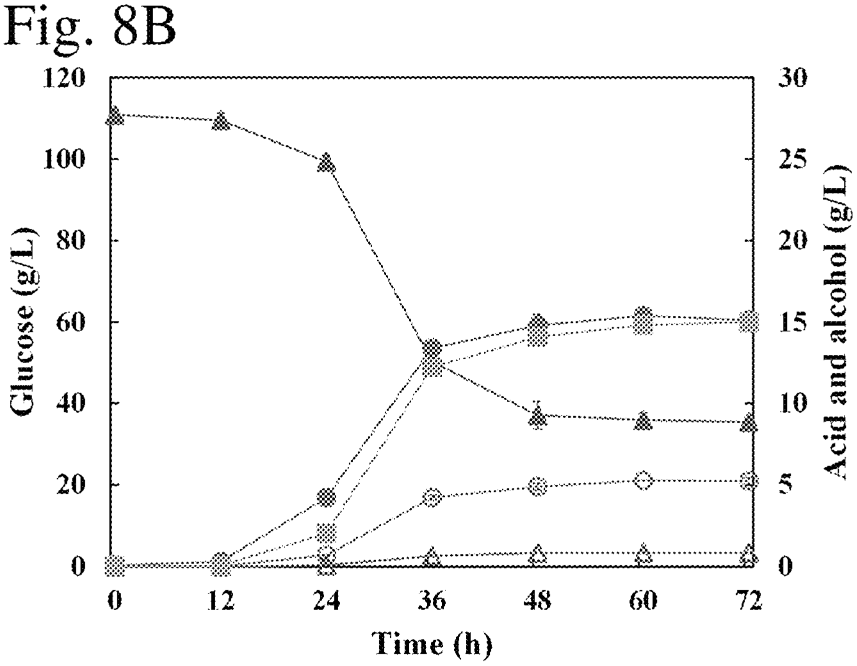
Figure 8C:
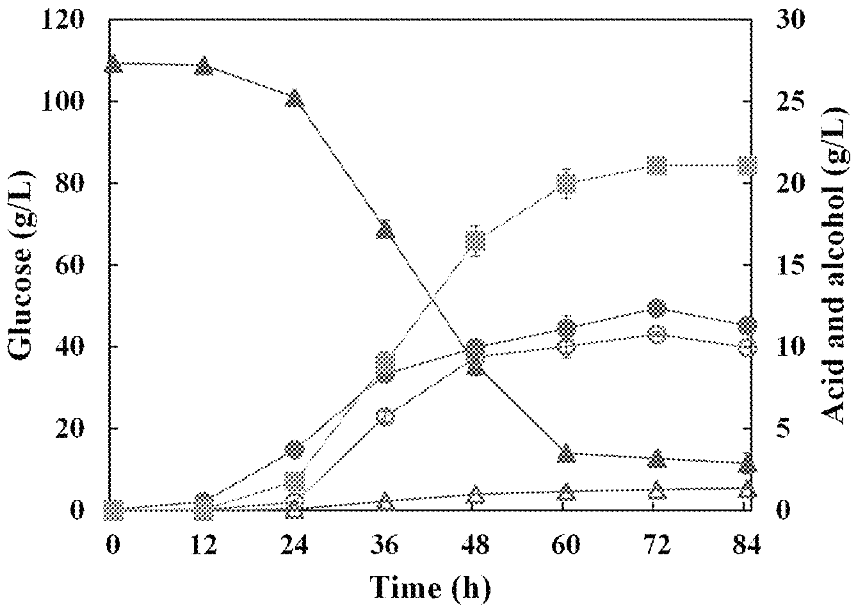
Figure 8D:
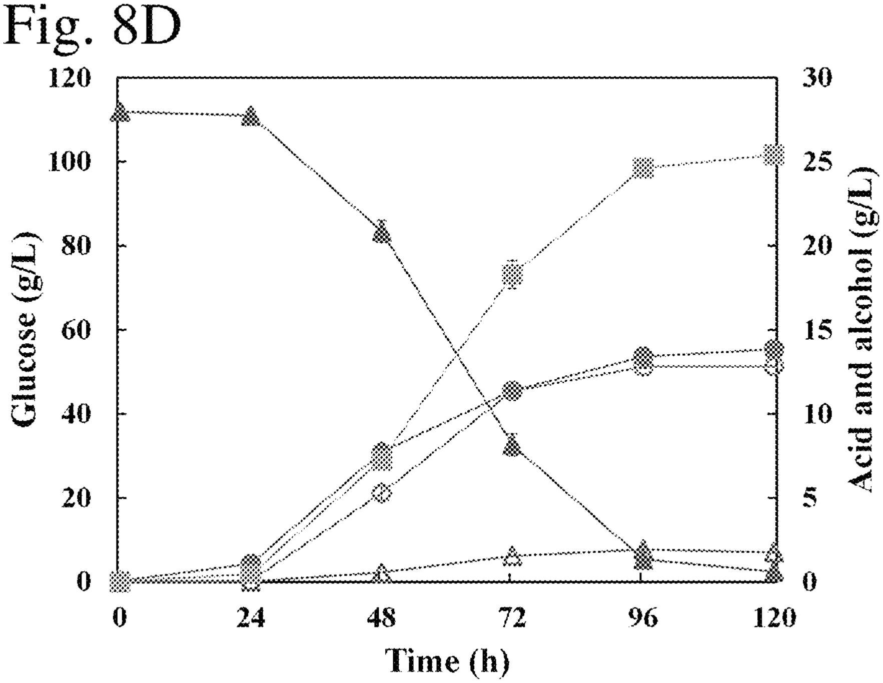
Figure 8E:
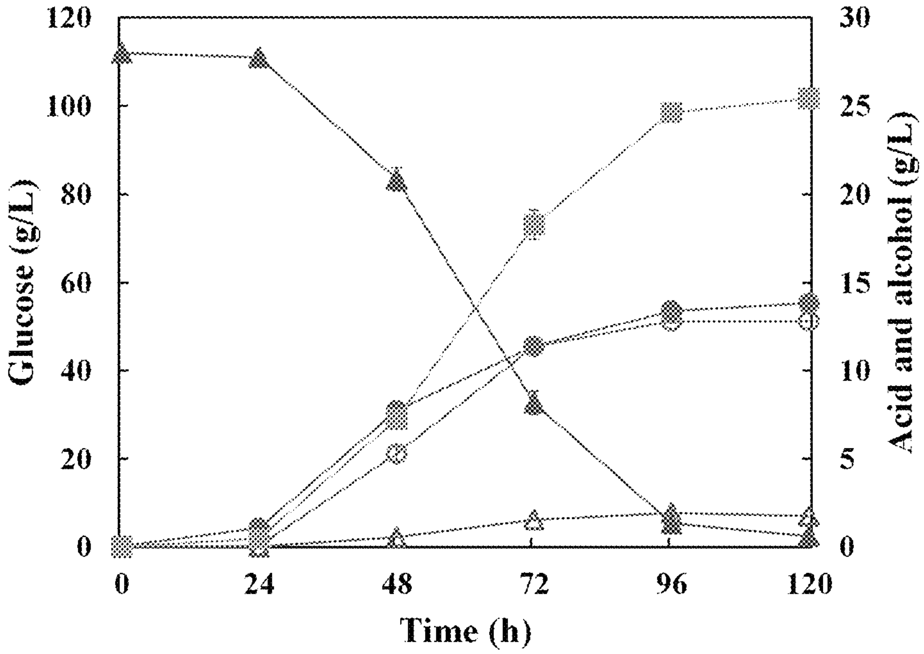

In *C. tyrobutyricum*, cat1 is the essential gene for butyrate biosynthesis, and the ptb-buk operon as seen in solventogenic clostridial strains does not exist (FIG. 5). Therefore, we hypothesized that deletion of cat1 could eliminate butyrate production, and thus the introduction of adhE1/adhE2 can lead to the conversion of butyryl-CoA for enhanced butanol production. However, it was previously reported that the disruption of cat1 was not achievable (with the mobile group II intron), because the inactivation of cat1 could likely lead to the inability of the strain for NADH oxidization (Lee et al., 2016a, mBio 7, e00743-16). Here, based on the high efficient CRISPR-Cas system for genome engineering, we attempted to delete the cat1 gene or replace it with adhE1 or adhE2. Similar as the previous report, the deletion of cat1 was fruitless despite numerous attempts, however the replacement of cat1 with adhE1 or adhE2 was successful, yielding mutants Δcat1::adhE1 and Δcat1::adhE2, respectively. As the control, the recombinants WT(pJZ98-Pcat1-adhE1) and WT(pJZ98-Pcat1-adhE2) were also obtained by introducing the plasmid-based adhE1 and adhE2 (driven by the cat1 promoter) overexpression vectors into *C. tyrobutyricum*. Initial batch fermentations were carried out at 37° C. (the optimum temperature for the cell growth of *C. tyrobutyricum*). Results demonstrated that acetate (14.8 g/L), ethanol (9.7 g/L) and butanol (8.7 g/L) were the major products with a low level of butyrate (1.3 g/L) produced for the control strain WT(pJZ98-Pcat1-adhE1) (Table 2 and FIG. 7A). However, for WT(pJZ98-Pcat1-adhE2), acetate (6.9 g/L), ethanol (7.4 g/L) and butyrate (34.1 g/L) were the major products, with only a small amount of butanol (2.0 g/L) was produced (Table 2 and FIG. 8A). As we expected, with the butyrate biosynthesis pathway replaced with the butanol producing pathway, mutants Δcat1::adhE1 and Δcat1::adhE2 produced negligible butyrate (0.6-0.8 g/L) but high levels of butanol (15.0 g/L). In addition, significant amounts of acetate (15.1-20.8 g/L) and ethanol (5.2-5.3 g/L) were also produced by the two mutants (Table 2 and FIGS. 7B & 8B).

Enhance Butanol Production by Carrying Out Fermentation at Low Temperatures

It is well known that the limited butanol tolerance of the host is a major bottleneck for butanol production in microorganisms. Recent studies showed that lower temperature could alleviate the alcohol toxicity and thus increase the alcohol production. Therefore, batch fermentations were further carried out at 30, 25 and 20° C. with Δcat1::adhE1 and Δcat1::adhE2, respectively. As seen in Table 2 and FIGS. 7B-7E & 8B-8E, the acetate production was kept at the similar levels at different temperatures. However, the production of ethanol and butanol was significantly increased at these lower temperatures. Butanol titers for Δcat1::adhE1 and Δcat1::adhE2 obtained at 20° C. were 21.4 and 26.2 g/L, respectively, which increased by 42.7% and 74.7%, respectively, compared with that obtained at 37° C. While the total BE (butanol and ethanol) production of Δcat1::adhE1 and Δcat1::adhE2 reached the maximum of 35.6 and 38.2 g/L, respectively at 25° C.

TABLE 2

Summary of fermentation results for *C. tyrobutyricum* mutants at various temperatures[a].

| Strain | Temperature (° C.) | Glucose consumption (g/L) | Acetate (g/L) | Butyrate (g/L) | Ethanol (g/L) | Butanol (g/L) | Total BE (g/L) | BE yield (g/g of glucose) |
|---|---|---|---|---|---|---|---|---|
| WT(pJZ98-Pcat1-adhE1) | 37 | 79.1 | 14.8 | 1.3 | 9.7 | 8.7 | 18.4 | 0.23 |
| WT(pJZ98-Pcat1-adhE2) | 37 | 109.0 | 6.9 | 34.1 | 7.4 | 2.0 | 9.4 | 0.09 |
| Δcat1::adhE1 | 37 | 87.1 | 20.8 | 0.6 | 5.3 | 15.0 | 20.3 | 0.23 |
| Δcat1::adhE2 | 37 | 75.5 | 15.1 | 0.8 | 5.2 | 15.0 | 20.2 | 0.27 |
| Δcat1::adhE1 | 30 | 109.6 | 22.5 | 0.8 | 14.3 | 17.2 | 31.5 | 0.29 |
| Δcat1::adhE2 | 30 | 96.7 | 12.3 | 1.3 | 10.8 | 21.1 | 31.9 | 0.33 |
| Δcat1::adhE1 | 25 | 111.9 | 22.8 | 1.3 | 16.6 | 19.0 | 35.6 | 0.32 |
| Δcat1::adhE2 | 25 | 109.4 | 13.9 | 1.8 | 12.8 | 25.4 | 38.2 | 0.35 |
| Δcat1::adhE1 | 20 | 111.9 | 21.8 | 1.6 | 10.4 | 21.4 | 31.8 | 0.28 |
| Δcat1::adhE2 | 20 | 112.2 | 15.2 | 2.4 | 8.9 | 26.2 | 35.1 | 0.31 |

[a]The fermentation profiles are provided in FIGS. 7A-7E & 8A-8E; values are based on at least two independent replicates.

TABLE 3

Bacterial strains and plasmids used in Example 1

| Strains/Plasmids | Relevant characteristic | Sources |
|---|---|---|
| | Strains | |
| *E. coli* | | |
| NEB Express | fhuA2 [Ion] ompT gal sulA11 R(mcr-73::miniTn10--$Tet^S$)2 [dcm] R(zgb-210::Tn10--$Tet^S$) endA1 Δ(mcrC-mrr)114::IS10 | New England BioLabs |
| CA434 | hsd20($r^B$-, $m^B$-), recA13, rpsL20, leu, proA2, with IncPb conjugative plasmid R702 | (Williams et al., 1990) |

TABLE 3-continued

| Bacterial strains and plasmids used in Example 1 | | |
|---|---|---|
| Strains/Plasmids | Relevant characteristic | Sources |
| *C. tyrobutyricum* | | |
| ATCC 25755 | KCTC 5387, wild type stain | ATCC |
| Δspo0A | Derived from ATCC 25755, with spo0A gene deleted | This work |
| ΔpyrF | Derived from ATCC 25755, with pyrF gene deleted | This work |
| Δspo0A ΔpyrF | Derived from ATCC 25755, with spo0A and pyrF genes deleted | This work |
| WT(pJZ98-Pcat1-adhE1) | Derived from ATCC 25755, harboring plasmid pJZ98-Pcat1-adhE1 | This work |
| WT(pJZ98-Pcat1-adhE2) | Derived from ATCC 25755, harboring plasmid pJZ98-Pcat1-adhE2 | This work |
| Δcat1::adhE1 | Derived from ATCC 25755, cat1 was replaced with adhE1 | This work |
| Δcat1::adhE2 | Derived from ATCC 25755, cat1 was replaced with adhE2 | This work |
| | Plasmids | |
| pYW34-BtgZI | CAK1 ori, ColE1 ori, $Amp^R$, $Erm^R$, Plac-Cas9, gRNA | (Wang et al., 2016) |
| pJZ23-Cas9 | pYW34-BtgZI derivative; pBP1 ori, ColE1 ori, $Amp^R$, $Cm^R$, TraJ, Plac-Cas9, gRNA | This work |
| pJZ23-Cas9-spo0A | pJZ23-Cas9 derivative; 20 nt-gRNA targeting on spo0A; two homology arms (~1 kb each) | This work |
| pJZ58-nCas9 | pJZ23-Cas9 derivative; Plac-nCas9 | This work |
| pJZ58-nCas9-spo0A | pJZ58-nCas9 derivative; 20 nt-gRNA targeting on spo0A; two homology arms (~1 kb each) | This work |
| pMTL82151 | pBP1 ori, $Cm^R$, ColE1 ori, TraJ | (Heap et al., 2009) |
| pWH36-AsCpf1 | pMTL82151 derivative; Plac-AsCpf1 | This work |
| pJZ60-AsCpf1-spo0A | pWH36-AsCpf1 derivative; 23 nt-crRNA targeting on spo0A; two homology arms (-1 kb each) | This work |
| pIF-1 | pMTL82151 derivative; protospacer Array1-17 flanked by 5' PAM sequence: 5'-CATCT-3' | This work |
| pIF-2 | pMTL82151 derivative; protospacer Array1-17 flanked by 5' PAM sequence: 5'-CATCA-3' | This work |
| pIF-3 | pMTL82151 derivative; protospacer Array1-17 flanked by 3' PAM sequence: 5'-AGGAT-3' | This work |
| pIF-4 | pMTL82151 derivative; protospacer Array1-17 flanked by 3' PAM sequence: 5'-CGGAT-3' | This work |
| pIF-5 | pMTL82151 derivative; protospacer Array1-17 flanked by 5' PAM sequence: 5'-AATTG-3' | This work |
| pIF-6 | pMTL82151 derivative; protospacer Array1-17 flanked by 5' PAM sequence: 5'-TTTCA-3' | This work |
| pIF-7 | pMTL82151 derivative; protospacer Array1-17 flanked by 5' PAM sequence: 5'-TATCT-3' | This work |
| pIF-8 | pMTL82151 derivative; protospacer Array2-1 flanked by 5' PAM sequence: 5'-CATCT-3' | This work |
| pIF-9 | pMTL82151 derivative; protospacer Array2-1 flanked by 5' PAM sequence: 5'-CATCA-3' | This work |
| pIF-10 | pMTL82151 derivative; protospacer Array2-1 flanked by 3' PAM sequence: 5'-AGGAT-3' | This work |

TABLE 3-continued

| Bacterial strains and plasmids used in Example 1 | | |
|---|---|---|
| Strains/Plasmids | Relevant characteristic | Sources |
| pIF-11 | pMTL82151 derivative; protospacer Array2-1 flanked by 3' PAM sequence: 5'-CGGAT-3' | This work |
| pIF-12 | pMTL82151 derivative; protospacer Array2-1 flanked by 5' PAM sequence: 5'-AATTG-3' | This work |
| pIF-13 | pMTL82151 derivative; protospacer Array2-1 flanked by 5' PAM sequence: 5'-TTTCA-3' | This work |
| pIF-14 | pMTL82151 derivative; protospacer Array2-1 flanked by 5' PAM sequence: 5'-TATCT-3' | This work |
| pIF-15 | pMTL82151 derivative; protospacer Array2-1 flanked by 5' PAM sequence: 5'-GTCA-3' | This work |
| pIF-16 | pMTL82151 derivative; protospacer Array2-1 flanked by 5' PAM sequence: 5'-CTCA-3' | This work |
| pIF-17 | pMTL82151 derivative; protospacer Array2-1 flanked by 5' PAM sequence: 5'-AACA-3' | This work |
| pIF-18 | pMTL82151 derivative; protospacer Array2-1 flanked by 5' PAM sequence: 5'-AGCA-3' | This work |
| pIF-19 | pMTL82151 derivative; protospacer Array2-1 flanked by 5' PAM sequence: 5'-ACCA-3' | This work |
| pIF-20 | pMTL82151 derivative; protospacer Array2-1 flanked by 5' PAM sequence: 5'-ATGA-3' | This work |
| pIF-21 | pMTL82151 derivative; protospacer Array2-1 flanked by 5' PAM sequence: 5'-ATTA-3' | This work |
| pIF-22 | pMTL82151 derivative; protospacer Array2-1 flanked by 5' PAM sequence: 5'-ATAA-3' | This work |
| pIF-23 | pMTL82151 derivative; protospacer Array2-1 flanked by 5' PAM sequence: 5'-ATCC-3' | This work |
| pIF-24 | pMTL82151 derivative; protospacer Array2-1 flanked by 5' PAM sequence: 5'-ATCG-3' | This work |
| pJZ69-leader-38spo0A | pMTL82151 derivative; Type I-B CRISPR genome editing plasmid containing the native leader and terminator sequences, the synthetic CRISPR array possessed a 38 nt spacer1 (5'-ATACCGTTTTCTTGCTCTCACTACTATTAGCTA TATCA-3') targeting on the spo0A gene, and two homology arms (~1 kb each) for spo0A deletion | This work |
| pJZ74-Plac-38spo0A | Same as pJZ69-leader-38spo0A, except that a lactose inducible promoter (instead of the native leader sequence) was used to drive the transcription of the CRISPR array | This work |
| pJZ75-Plac-38spo0A | Same as pJZ74-Plac-38spo0A, except that the 38-nt spacer1 was replaced with the 38-nt spacer2 (5'-GCAACCATAGCTATAAATTCTGAATTTGTTGG TTTACC-3') | This work |
| pJZ76-Para-38spo0A | Same as pJZ74-Plac-38spo0A, except that the lactose inducible promoter was replaced with an arabinose inducible promoter | This work |
| pJZ74-Plac-10spo0A | Same as pJZ74-Plac-38spo0A, except that the 38-nt spacer1 was replaced with the 10-nt spacer1 (5'-ATACCGTTTT-3') | This work |
| pJZ74-Plac-20spo0A | Same as pJZ74-Plac-38spo0A, except that the 38-nt spacer1 was replaced with the 20-nt spacer1 (5'-ATACCGTTTTCTTGCTCTCA-3') | This work |
| pJZ74-Plac-30spo0A | Same as pJZ74-Plac-38spo0A, except that the 38-nt spacer1 was replaced with the 30-nt spacer1 (5'-ATACCGTTTTCTTGCTCTCACTACTATTAG-3') | This work |

TABLE 3-continued

| Bacterial strains and plasmids used in Example 1 | | |
|---|---|---|
| Strains/Plasmids | Relevant characteristic | Sources |
| pJZ74-Plac-50spo0A | Same as pJZ74-Plac-38spo0A, except that the 38-nt spacer1 was replaced with the 50-nt spacer1 (5'-ATACCGTTTTCTTGCTCTCACTACTATTAGCTA TATCATTATTAAACATT-3') | This work |
| pJZ77-Plac-30spo0A | Same as pJZ74-Plac-30spo0A, except that ~300 bp homology arms were used (instead of ~1 kb arms) | This work |
| pJZ77-Plac-30pyrF | Same as pJZ74-Plac-38spo0A, except that the 38-nt spacer1 was replaced with the 30-nt spacer3 (5'-TTGGATGTTCTTATAAGGACAAATACTCCT-3') targeting on the pyrF gene and the homology arms for spo0A deletion were replaced with the homology arms (~300 bp each ×2) for pyrF deletion | This work |
| pJZ77-Plac-30spo0A/30pyrF | Combined pJZ77-Plac-30spo0A and pJZ77-Plac-30pyrF, including the 30-nt spacer1 targeting on the spo0A gene, the 30-bp spacer3 targeting on the pyrF gene, the homology arms (~300 bp each ×2) for spo0A deletion and the homology arms (~300 bp each ×2) for pyrF deletion | This work |
| pJZ86-Plac-34pta/ack | Same as pJZ74-Plac-38spo0A, except that the 38-nt spacer1 was replaced with the 34-nt spacer4 (5'-GATTGTGCTGTAAATCCTGTACCTAATACTGA AC-3') targeting on the pta-ack operon and the homology arms for spo0A deletion were replaced with the homology arms (~500 bp each ×2) for pta-ack deletion | This work |
| pJZ86-Plac-34pta/ack(adhE1) | pJZ86-Plac-34pta/ack derivative; adhE1 was inserted between the two homology arms | This work |
| pJZ86-Plac-34pta/ack(adhE2) | pJZ86-Plac-34pta/ack derivative; adhE2 was inserted between the two homology arms | This work |
| pJZ95-Plac-34cat1 | Same as pJZ74-Plac-38spo0A, except that the 38-nt spacer1 was replaced with the 34-nt spacer5 (5'-CTTGTAGAAGATGGATCAACCCTACAACTTG GTA-3'; SEQ ID NO: 4) targeting on the cat1 gene and the homology arms for spo0A deletion were replaced with the homology arms (~500 bp each ×2) for cat1 deletion | This work |
| pJZ95-Plac-34cat1(adhE1) | pJZ95-Plac-34cat1 derivative; adhE1 was inserted between the two homology arms | This work |
| pJZ95-Plac-34cat1(adhE2) | pJZ95-Plac-34cat1 derivative; adhE2 was inserted between the two homology arms | This work |
| pJZ98-Pcat1 | pMTL82151 derivative; containing cat1 promoter | This work |
| pJZ98-Pcat1-adhE1 | pJZ98-Pcat1 derivative; plasmid-based adhE1 gene overexpression driven by the cat1 gene promoter | This work |
| pJZ98-Pcat1-adhE2 | pJZ98-Pcat1 derivative; plasmid-based adhE2 gene overexpression driven by the cat1 gene promoter | This work |

TABLE 4

| Primers used in Example 1 | |
|---|---|
| Primers (pair) | Sequences |
| spo0A deletion using CRISPR-Cas9 or CRISPR-nCas9 system | |
| Cm marker | 5'-ACAATTGAATTTAAAAGAAACCGATAGGCCGGCCAGTGGGCAA GTTG-3' (SEQ ID NO: 26)<br>5'-CTTTAGTAACGTGTAACTTTCCAAATGGAGTTTAAACTTAGGG TAAC-3' (SEQ ID NO: 27) |

TABLE 4-continued

| Primers used in Example 1 | |
|---|---|
| Primers (pair) | Sequences |
| in vitro Cas9 nuclease double digestion of CAK1 | 5'-AAAAAAAGCACCGACTCGGTGCCACTTTTTCAAGTTGATAACGG ACTAGCCTTATTTTAACTT GCTATTTCTAGCTCTAAAAC-3' (SEQ ID NO: 28)<br>5'-AGAAATTAATACGACTCACTATAGGGATACTAAAACTGAATTGA TTGTTTTAGAGCTAGAAAT AGCAAGTTAAAATAAGG-3' (SEQ ID NO: 29)<br>5'-AGAAATTAATACGACTCACTATAGGGAGTGCAAAAAAAGATATA ATGTTTTAGAGCTAGAAAT AGCAAGTTAAAATAAGG-3' (SEQ ID NO: 30) |
| pBP1 replicon | 5'-CGAACACGAACCGTCTTATCTCCCATTGTTCTGAATCCTTAGCT AATGG-3' (SEQ ID NO: 31)<br>5'-TAATGACCCCGAAGCAGGGGGCCCAATGAATTTGTAAATAAACC ACAAAC-3' (SEQ ID NO: 32) |
| TraJ | 5'-GTAATACTAAAACTGAATTGATTCCTGCTTCGGGGTCATTATA G-3' (SEQ ID NO: 33)<br>5'-ATCAAGTAAATAAACCAAGTATATAAGGGCCCGATCGGTCTTGC CTTGCTCGTCG-3' (SEQ ID NO: 34) |
| PsRNA + 20 nt protospacer sequence Homology arms (~1 kb each) | 5'-AAAGTTAAAAGAAGAAAATAGAAATATAATCTTTAATTTGAAAA GATTTAAG-3' (SEQ ID NO: 35)<br>5'-TTGCTATTTCTAGCTCTAAAACCGCTACTTCAATAGCATGTCAT GGTGGAATGATAAGGG-3' (SEQ ID NO: 36)<br>5'-CTTTGTGATATGACTAATAATTAGCGGCCGCCTCAGGGTGTATT AGTTGTAG-3' (SEQ ID NO: 37)<br>5'-GTTAACCATTGATATCACTTTAATATTTTACTCCCCTTTTAT T-3' (SEQ ID NO: 38)<br>5'-AATAAAAGGGGAGTAAAATATTAAAGTGATATCAATGGTTAA C-3' (SEQ ID NO: 39)<br>5'-ATCCACTAGTAACCATCACACTGGCGGCCGCGACCAATACTGAA CTATGACC-3' (SEQ ID NO: 40) |
| Plac-nCas9 | 5'-CACCGACGAGCAAGGCAAGACCGATCGGGCCCTTATATACTTGG TTTATTTACTTG-3' (SEQ ID NO: 41)<br>5'-CCTATTGAGTATTTCTTATCCATTTCAGCCCTCCTGTGAAATT G-3' (SEQ ID NO: 42)<br>5'-CAATTTCACAGGAGGGCTGAAATGGATAAGAAATACTCAATAG G-3' (SEQ ID NO: 43)<br>5'-GATAAATTTATAAAATTCTTCTTGGC-3' (SEQ ID NO: 44) |
| spo0A deletion using CRISPR-AsCpf1 system | |
| Plac-AsCpf1 | 5'-GGAAACAGCTATGACCGCGGCCGCTGTATCTTATATACTTGGTT TATTTACTTGATTATT-3' (SEQ ID NO: 45)<br>5'-TGGTAGAGATTGGTGAAGCCTTCAAACTGTGTCATTTCAGCCCT CCTGTGAAATTGTTATCCG CTCACAA-3' (SEQ ID NO: 46)<br>5'-TTGTGAGCGGATAACAATTTCACAGGAGGGCTGAAATGACACAG TTTGAAGGCTTCACCAAT CTCTACCA-3' (SEQ ID NO: 47)<br>5'-GGGTACCGAGCTCGAATTCGTAATCATGGTTTAGTTTCTCAGTT CTTGAATGTAGGCCAG-3' (SEQ ID NO: 48) |
| PsRNA-crRNA | 5'-GATTACGAATTCGAGCTCGGTACCCGGGATAATCTTTAATTTGA AAAGATTTAAG-3' (SEQ ID NO: 49)<br>5'-TTAGCTGAAAGCACGATTACTCTCGGATCTACAAGAGTAGAAAT TAATGGTGG-3' (SEQ ID NO: 50) |
| Homology arms (~1 kb each) | 5'-GATCCGAGAGTAATCGTGCTTTCAGCTAATTTCTACTCTTGTAG ATCTCAGGGTGTATTAGTTG TAG-3' (SEQ ID NO: 51)<br>5'-CCATGGACGCGTGACGTCGACTCTAGAGGACCAATACTGAACTA TGACC-3' (SEQ ID NO: 52) |
| spo0A deletion using endogenous Type I-B CRISPR-Cas system | |
| Leader + 38-nt spacer1 + terminator | 5'-CTGTATCCATATGACCATGATTACGTAAGATCGTAGCAGATAAG GAT-3' (SEQ ID NO: 53)<br>5'-GCTAATAGTAGTGAGAGCAAGAAAACGGTATATTTAAATACATC TCATGTTAAGGTTCAACCTGTGTAAAATAGCCATTC-3' (SEQ ID NO: 54)<br>5'-TTTCTTGCTCTCACTACTATTAGCTATATCAGTTGAACCTTAAC ATGAGATGTATTTAAATCCCATAGAAGCTCTATACT-3' (SEQ ID NO: 55)<br>5'-CTACAACTAATACACCCTGAGGGTACCTGGAGATATAATAAGCT ATGCC-3' (SEQ ID NO: 56) |

TABLE 4-continued

| Primers used in Example 1 | |
|---|---|
| Primers (pair) | Sequences |
| Homology arms (~1 kb each) | 5'-CATGATTACGAATTCGAGCTCGGTACCCTCAGGGTGTATTAGTTGTAG-3' (SEQ ID NO: 57)<br>5'-GTTAACCATTGATATCACTTTAATATTTTACTCCCCTTTTATT-3' (SEQ ID NO: 58)<br>5'-AATAAAAGGGGAGTAAAATATTAAAGTGATATCAATGGTTAAC-3' (SEQ ID NO: 59)<br>5'-TGGACGCGTGACGTCGACTCTAGAGGACCAATACTGAACTATGACC-3' (SEQ ID NO: 60) |
| Plac + 38-nt spacer1 + terminator | 5'-CTGTATCCATATGACCATGATTACGGATTGGGCCCTTATATACTTGG-3' (SEQ ID NO: 61)<br>5'-GCAAGAAAACGGTATATTTAAATACATCTCATGTTAAGGTTCAACTTCAGCCCTCCTGTGAAA TTG-3' (SEQ ID NO: 62)<br>5'-CATGAGATGTATTTAAATATACCGTTTTCTTGCTCTCAC-3' (SEQ ID NO: 63)<br>5'-CTACAACTAATACACCCTGAGGGTACCTGGAGATATAATAAGCTATGCC-3' (SEQ ID NO: 64) |
| Plac + 38-nt spacer2 + terminator | 5'-CCAACAAATTCAGAATTTATAGCTATGGTTGCATTTAAATACATCTCATGTTAAGGTTCAACTTCAGCCCTCCTGTGAAATTG-3' (SEQ ID NO: 65)<br>5'-ATAGCTATAAATTCTGAATTTGTTGGTTTACCGTTGAACCTTAACATGAGATGTATTTAAATCCCATAGAAGCTCTATACT-3' (SEQ ID NO: 66) |
| Para + 38-nt spacer1 + terminator | 5'-CTGTATCCATATGACCATGATTACGTTATGAAAGCGATTACCTATAT-3' (SEQ ID NO: 67)<br>5'-GCAAGAAAACGGTATATTTAAATACATCTCATGTTAAGGTTCAACAATATTCCTCCTAAATTTATAATC-3' (SEQ ID NO: 68) |
| Plac + 10-nt spacer1 + terminator | 5'-GGTTCAACAAAACGGTATATTTAAATACATCTCATGTTAAGGTTCAACTTCAGCCCTCCTGTG AAATTG-3' (SEQ ID NO: 69)<br>5'-ATTTAAATATACCGTTTTGTTGAACCTTAACATGAGATGTATTTAAATCCCATAGAAGCTCTATACT-3' (SEQ ID NO: 70) |
| Plac + 20-nt spacer1 + terminator | 5'-CAACTGAGAGCAAGAAAACGGTATATTTAAATACATCTCATGTTAAGGTTCAACTTCAGCCCT CCTGTGAAATTG-3' (SEQ ID NO: 71)<br>5'-AAATATACCGTTTTCTTGCTCTCAGTTGAACCTTAACATGAGATGTATTTAAATCCCATAGAAG CTCTATACT-3' (SEQ ID NO: 72) |
| Plac + 30-nt spacer1 + terminator | 5'-CTAATAGTAGTGAGAGCAAGAAAACGGTATATTTAAATACATCTCATGTTAAGGTTCAACTTC AGCCCTCCTGTGAAATTG-3' (SEQ ID NO: 73)<br>5'-ATACCGTTTTCTTGCTCTCACTACTATTAGGTTGAACCTTAACATGAGATGTATTTAAATCCCA TAGAAGCTCTATACT-3' (SEQ ID NO: 74) |
| Plac + 50-nt spacer1 + terminator | 5'-GATATAGCTAATAGTAGTGAGAGCAAGAAAACGGTATATTTAAATACATCTCATGTTAAGGTTCAACTTCAGCCCTCCTGTGAAATTG-3' (SEQ ID NO: 75)<br>5'-TTGCTCTCACTACTATTAGCTATATCATTATTAAACATTGTTGAACCTTAACATGAGATGTATTTAAATCCCATAGAAGCTCTATACT-3' (SEQ ID NO: 76) |
| spo0A and pyrF double deletion using endogenous Type I-B CRISPR-Cas system | |
| spo0A deletion (arms, ~300 bp each) pyrF deletion (30-nt spacer) | 5'-CATGATTACGAATTCGAGCTCGGTACCGTTCAAGGTATGAGTGGAAGTCC-3' (SEQ ID NO: 77)<br>5'-TGGACGCGTGACGTCGACTCTAGAGACATCTTCTATATATCTGCAAAATAGCTTC-3' (SEQ ID NO: 78)<br>5'-CCTGACTCTAGAGTCGACGTCACGCGTCGATTGGGCCCTTATATACTTGG-3' (SEQ ID NO: 79)<br>5'-AGGAGTATTTGTCCTTATAAGAACATCCAAATTTAAATACATCTCATGTTAAGGTTCAACTTCAGCCCTCCTGTGAAATTG-3' (SEQ ID NO: 80)<br>5'-TTGGATGTTCTTATAAGGACAAATACTCCTGTTGAACCTTAACATGAGATGTATTTAAATCCCATAGAAGCTCTATACT-3' (SEQ ID NO: 81)<br>5'-CGACGTTGTAAAACGACGGCCAGTGCCATGGAGATATAATAAGCTATGCC-3' (SEQ ID NO: 82) |

TABLE 4-continued

Primers used in Example 1

| Primers (pair) | Sequences |
| --- | --- |
| pyrF deletion (arms, ~300 bp each) | 5'-CTGTATCCATATGACCATGATTACGGCTATATTGGGTTTCATAGATCC-3' (SEQ ID NO: 83)<br>5'-GCACACTCTGCATAGTCTGTGTAAGTATCCAGGCCTACACATAC-3' (SEQ ID NO: 84)<br>5'-GTATGTGTAGGCCTGGATACTTACACAGACTATGCAGAGTGTGC-3' (SEQ ID NO: 85)<br>5'-TGGACGCGTGACGTCGACTCTAGAGTAGTTCCATTTCCAACTACCTG-3' (SEQ ID NO: 86) |
| spo0A + pyrF deletion ((30 + 30) nt spacer) | 5'-CTGTATCCATATGACCATGATTACGCCCGGGGATTGGGCCCTTATATACTTGG-3' (SEQ ID NO: 87)<br>5'-GGAGTATTTGTCCTTATAAGAACATCCAAATTTAAATACATCTCATGTTAAGGTTCAACTTCAG CCCTCCTGTGAAATTG-3' (SEQ ID NO: 88)<br>5'-GGATGTTCTTATAAGGACAAATACTCCTGTTGAACCTTAACATGAGATGTATTTAAATATACCG TTTTCTTGCTCTCAC-3' (SEQ ID NO: 89)<br>5'-CTACAACTAATACACCCTGAGGGTACCTGGAGATATAATAAGCTATGCC-3' (SEQ ID NO: 90) |
| spo0A + pyrF deletion ((~300 + ~300) bp arms) | 5'-CATGATTACGAATTCGAGCTCGGTACCGCTATATTGGGTTTCATAGATCC-3' (SEQ ID NO: 91)<br>5'-GGACTTCCACTCATACCTTGAACTAGTTCCATTTCCAACTACCTG-3' (SEQ ID NO: 92)<br>5'-CAGGTAGTTGGAAATGGAACTAGTTCAAGGTATGAGTGGAAGTCC-3' (SEQ ID NO: 93)<br>5'-TGGACGCGTGACGTCGACTCTAGAGACATCTTCTATATATCTGCAAAATAGCTTC-3' (SEQ ID NO: 94) |
| pta/ack deletion (or replaced by adhE1/adhE2) using endogenous Type I-B CRISPR-Cas system | |
| Plac + 34-nt spacer4 + terminator | 5'-CTGTATCCATATGACCATGATTACGGATTGGGCCCTTATATACTTGG-3' (SEQ ID NO: 95)<br>5'-AGTATTAGGTACAGGATTTACAGCACAATCATTTAAATACATCTCATGTTAAGGTTCAACTTC AGCCCTCCTGTGAAATTG-3' (SEQ ID NO: 96)<br>5'-GTGCTGTAAATCCTGTACCTAATACTGAACGTTGAACCTTAACATGAGATGTATTTAAATCCCATAGAAGCTCTATACT-3' (SEQ ID NO: 97)<br>5'-GTCGACTCTAGAGGATCCCCGGGTACCTGGAGATATAATAAGCTATGCC-3' (SEQ ID NO: 98) |
| Homology arms (~500 bp each) | 5'-GGCATAGCTTATTATATCTCCAGGTACGTATCAACTACGCCTAAATTCTCC-3' (SEQ ID NO: 99)<br>5'-TAGGCTGTTCAGGGATCCCCGGGTACCTTTCGTTTCTCCCTTCAAGAT-3' (SEQ ID NO: 100)<br>5'-GGAGAAACGAAAGGTACCCGGGGATCCCTGAACAGCCTATGGAAGACC-3' (SEQ ID NO: 101)<br>5'-TGGACGCGTGACGTCGACTCTAGAGCACCGTCAATTGCACATACAC-3' (SEQ ID NO: 102) |
| adhE1 | 5'-TATCTTGAAGGGAGAAACGAAAGGTACATGAAAGTCACAACAGTAAAGG-3' (SEQ ID NO: 103)<br>5'-TTATGGTCTTCCATAGGCTGTTCAGGGTTGAAATATGAAGGTTTAAGGTTG-3' (SEQ ID NO: 104) |
| adhE2 | 5'-TATCTTGAAGGGAGAAACGAAAGGTACATGAAAGTTACAAATCAAAAAG-3' (SEQ ID NO: 105)<br>5'-TTATGGTCTTCCATAGGCTGTTCAGGTTAAAATGATTTTATATAGATATCC-3' (SEQ ID NO: 106) |
| cat1 deletion (or replaced by adhE1/adhE2) using endogenous Type I-B CRISPR-Cas system | |
| Plac + 34-nt spacer5 + terminator | 5'-CTGTATCCATATGACCATGATTACGGATTGGGCCCTTATATACTTGG-3' (SEQ ID NO: 107)<br>5'-AGTTGTAGGGTTGATCCATCTTCTACAAGATTTAAATACATCTCATGTTAAGGTTCAACTTCAGCCCTCCTGTGAAATTG-3' (SEQ ID NO: 108)<br>5'-GTAGAAGATGGATCAACCCTACAACTTGGTAGTTGAACCTTAACATGAGATGTATTTAAATCC CATAGAAGCTCTATACT-3' (SEQ ID NO: 109)<br>5'-GTCGACTCTAGAGGATCCCCGGGTACCTGGAGATATAATAAGCTATGCC-3' (SEQ ID NO: 110) |

TABLE 4-continued

| Primers used in Example 1 | |
|---|---|
| Primers (pair) | Sequences |
| Homology arms (~500 bp each) | 5'-GGCATAGCTTATTATATCTCCAGGTACACCCATGCTGCAAAGCAAGTT-3' (SEQ ID NO: 111)<br>5'-TGAGAAAGCTAAGGATCCCCGGGTACCAAAAACCACCCTTTCATAAATT-3' (SEQ ID NO: 112)<br>5'-GGGTGGTTTTTGGTACCCGGGGATCCTTAGCTTTCTCAAAAGATATTTT-3' (SEQ ID NO: 113)<br>5'-TGGACGCGTGACGTCGACTCTAGAGCCATATGCGGTGGTTATCAAC-3' (SEQ ID NO: 114) |
| adhE1 | 5'-AATTTATGAAAGGGTGGTTTTTGGTACATGAAAGTCACAACAGTAAAGG-3' (SEQ ID NO: 115)<br>5'-TTAAAAATATCTTTTGAGAAAGCTAAGGTTGAAATATGAAGGTTTAAGGTTG-3' (SEQ ID NO: 116) |
| adhE2 | 5'-AATTTATGAAAGGGTGGTTTTTGGTACATGAAAGTTACAAATCAAAAAG-3' (SEQ ID NO: 117)<br>5'-TTAAAAATATCTTTTGAGAAAGCTAAGTTAAAATGATTTTATATAGATATCC-3' (SEQ ID NO: 118) |
| Plasmid based adhE1/adhE2 overexpression | |
| cat1 promoter | 5'-CTGTATCCATATGACCATGATTACGGTAGACTTTAAGGATGGAACC-3' (SEQ ID NO: 119)<br>5'-TCGACTCTAGAGGATCCCCGGGTACCGAATTCTGTCGACTGCGATGAGCTAGGTCAGTAAAA ACCACCCTTTCATAAATT-3' (SEQ ID NO: 120) |
| adhE1 | 5'-ATATAATTTATGAAAGGGTGGTTTTTATGAAAGTCACAACAGTAAAGG-3' (SEQ ID NO: 121)<br>5'-CGACTCTAGAGGATCCCCGGGTACCGAATTCGTTGAAATATGAAGGTTTAAGGTTG-3' (SEQ ID NO: 122) |
| adhE2 | 5'-ATATAATTTATGAAAGGGTGGTTTTTATGAAAGTTACAAATCAAAAAG-3' (SEQ ID NO: 123)<br>5'-CGACTCTAGAGGATCCCCGGGTACCGGTAACCTTAAAATGATTTTATATAGATATCC-3' (SEQ ID NO: 124) |
| Mutant detection | |
| spo0A deletion | 5'-TGTTCCTGTAGGATCAGTATC-3' (SEQ ID NO: 125)<br>5'-GGACTGTACCTCTGGTAGTTC-3' (SEQ ID NO: 126) |
| pyrF deletion | 5'-GTTGAAAGACAGCTATATCTTGG-3' (SEQ ID NO: 127)<br>5'-ATGCCATGTGATTCTCCATAG-3' (SEQ ID NO: 128) |
| Pta-ack deletion | 5'-TCTATACCTTCAGATACTTCTGG-3' (SEQ ID NO: 129)<br>5'-CTCACCTCTATACATTAGCCAC-3' (SEQ ID NO: 130) |
| cat1 deletion | 5'-GCCATTAAGTACAAATGAGATAG-3' (SEQ ID NO: 131)<br>5'-GCCATTAAGTACAAATGAGATAG-3' (SEQ ID NO: 132) |

Discussion

Within the past few years, CRISPR-Cas, the adaptive immune system from bacteria and archaea, has been repurposed for versatile genome editing and transcriptional regulation in various strain. However, so far, the majority of such applications are based on the Type II CRISPR-Cas9 system derived from *S. pyogenes*.

Due to the unique feature of the chromosome of prokaryotic cells, the expression of the heterologous Cas9 is highly toxic, thus leading to poor transformation efficiency and failure of genome editing. Recently, the type V CRISPR-Cpf1 system has also been exploited for genome editing purposes. It has advantages over the CRISPR-Cas9 system due to its smaller size of the effector protein (Cpf1) and the more compact RNA guide (crRNA). Although the toxicity of Cpf1 is much lower than that of Cas9 as demonstrated in specific strains, remarkable decrease in transformation efficiency is still observed with the expression of Cpf1 in the host. Therefore, it is challenging to carry out genome editing with CRISPR-Cas9/Cpf1 systems in microorganisms with low DNA transformation efficiencies.

In this work, after many unsuccessful attempts for genome editing with the CRISPR-Cas9 or CRISPR-AsCpf1 systems, we successfully repurposed the Type I-B CRISPR-Cas system of *C. tyrobutyricum* as an efficient genome editing tool for this microorganism.

In silico analysis of the CRISPR array in *C. tyrobutyricum* identified only one spacer sequence that can match protospacers from phage (prophage) of *Clostridium* and *Geobacillus* (FIG. 1B). However, we hypothesized that, due to the possible horizontal transferring property of CRISPR-Cas loci between closely-related strain, the Type I-B CRISPR-Cas systems from different *Clostridium* strain could be very similar and share similar/same PAMs and direct repeat sequences. Indeed, our subsequent in silico analysis demonstrated high homology between the CRISPR array in *C.*

*tyrobutyricum* and that in *C. pasteurianum*. Therefore, the three PAM sequences from *C. pasteurianum* along with the putative PAMs identified in *C. tyrobutyricum* were employed to assess the activity of the endogenous CRISPR-Cas system of *C. tyrobutyricum*. The in vivo plasmid interference assay revealed that the Cas protein in *C. tyrobutyricum* had high affinity to the 5' adjacent PAM sequences TCA and TCG (FIG. 2B). These results verified our hypothesis that the Type I-B CRISPR-Cas system from *C. tyrobutyricum* shares the same PAM sequence (TCA) as that in *C. pasteurianum*, as well as those in *Clostridium tetani* and *C. thermocellum*.

In attempt for the genome editing with the endogenous CRISPR-Cas system, initially, the native leader sequence was used as the promoter to drive the transcription of the synthetic CRISPR array. However, no transformants were obtained, likely due to the toxicity of the endogenous CRISPR-Cas system when it was instantly expressed. A lactose inducible promoter was employed to replace the leader sequence to drive the expression of the CRISPR-Cas system, resulting in an overall transformation efficiency of 1.7 CFU/mL donor (FIG. 3C). This transformation efficiency is still low, but is enough to enable us to obtain desirable mutants with a high editing efficiency. With this, we demonstrated that the inducible expression of the endogenous CRISPR-Cas array is achievable (although the configuration of the original native leader sequence for the CRISPR array regulation was complex) and effective to realize efficient genome editing in the host microorganism. It is also worthwhile to point out that, the same inducible promoter was also used to drive the expression of Cas9, nCas9 or AsCpf1 proteins to achieve genome editing for the same microorganism, however no successful transformation was achieved with any of the plasmids containing these heterologous nuclease (or nickase) proteins. This confirmed that the toxicity of the endogenous CRISPR-Cas system is much lower than that of heterologous CRISPR-Cas9/nCas9/AsCpf1 systems and thus more implementable for genome editing purposes (FIGS. 3B & 3C).

Although the markerless genome engineering platform was developed, and high editing efficiency could be obtained, the transformation efficiency was still low which would restrict the application of the genome editing platform in *C. tyrobutyricum*. The length of spacers identified from the CRISPR Array1 and Array2 are not all the same (ranging from 34-38 nt). We reasoned that the length of the spacer might have an impact on the transformation efficiency and/or genome editing efficiency. Therefore, various lengths of spacers were systematically evaluated in the developed CRISPR-Cas system in the context for spo0A deletion. Results indicated that, the transformation was not successful when the spacer ≤20 nt was used, suggesting possible severe off-target effects (FIG. 3C). Spacers ranging from 30 to 50 nt can be used for targeting purposes for the successful genome editing. Comparatively, when shorter spacers were used, the genome editing efficiency was slightly decreased (for 30-nt spacer, an editing efficiency of 93.3% was obtained based on the large colonies), but meanwhile the transformation efficiency was dramatically enhanced (by approximately 500-fold for the 30-nt spacer). Therefore, depending on the different genome editing purposes, one can make a tradeoff between the transformation efficiency and genome editing efficiency by using a spacer of an appropriate length. Briefly, based on the above results for the deletion of spo0A particularly, spacers of 30-38 nt seems good options. It should be pointed out that, one of the advantages with such an endogenous CRISPR-Cas system comparing to the type II CRISPR-Cas9 system for genome editing is that, the employment of the longer spacer sequence (30-38 nt vs. 20 nt for the spCRISPR-Cas9) can abate the potential off-target effect. Apparently, the longer the spacer sequence is, the more specific the targeting of the crRNA. For eukaryotic cells, the off-target effect can lead to unspecific mutations on the chromosome, which is highly problematic for various applications. This won't occur for the prokaryotic cells due to their inefficient endogenous nonhomologous end-joining (NHEJ) capability for the automatic DNA repairing. However, the off-target effect in prokaryotic cells can lead to cell death and thus failure of genome editing.

In this study, multiplex genome editing was achieved by using the endogenous CRISPR-Cas system of *C. tyrobutyricum* (FIG. 4A). A synthetic CRISPR array carrying two spacers was used for the chromosome targeting to delete spo0A and pyrF simultaneously, yielding an editing efficiency of up to 100% (FIG. 4C). To date, this is the first success for multiplex genome editing in microorganisms with underdeveloped genome engineering tools such as *Clostridium.*

*C. tyrobutyricum* is a natural hyper-butyrate producer, which has been engineered for butanol production previously. The cat1 gene is believed to be the essential gene for butyrate production in *C. tyrobutyricum*, and the deletion of cat1 was not previously achievable. In this study, based on the developed CRISPR-Cas genome engineering system, we successfully replaced the cat1 gene with adhE1/adhE2. In this way, the butyrate production in *C. tyrobutyricum* was almost eliminated and the microorganism was converted into a hyper-butanol producer (FIG. 5). Previous studies have demonstrated that the lower temperature is beneficial to enhance the butanol tolerance of host strains, which may be because of the change of cell membrane composition and fluidity under lower temperatures. Therefore, fermentations for butanol production with the *C. tyrobutyricum* mutant were further carried out at lower temperatures. At 20° C., the butanol production in the mutant Δcat1::adhE2 reached 26.2 g/L in a regular batch fermentation. To the best of our knowledge, this is the highest butanol production that has ever been reported in a batch fermentation. We also investigated the butanol production of *C. beijerinckii* NCIMB 8052 and *C. saccharoperbutylacetonicum* N1-4 at lower temperatures (Table 5), to confirm whether carrying out fermentations at low temperatures is a broadly applicable mechanism to achieve high butanol production with other strains as well. Although the butanol production of these two solventogenic clostridia was increased at lower temperatures, the increment was far lower than that obtained with mutant Δcat1::adhE2, indicating that *C. tyrobutyricum* has much greater potential and thus is a more favorable host for butanol production. Furthermore, there is no acetone production in the fermentation of Δcat1::adhE2 as seen in the ABE fermentation; butanol, ethanol and acetate are the only primary end products. This on one hand simplifies the downstream recovery process; on the other, these end products could be further upgraded to high-value biochemicals (such as diesel, esters, etc.) through chemical or biochemical processes.

TABLE 5

Summary of fermentation results for *C. beijerinckii* NCIMB 8052 and *C. saccharoperbutylacetonicum* N1-4 at various temperatures[a]

| Strain | Temperature (° C.) | Acetate (g/L) | Butyrate (g/L) | Acetone (g/L) | Ethanol (g/L) | Butanol (g/L) | Total ABE (g/L) | ABE yield (g/g of glucose) |
|---|---|---|---|---|---|---|---|---|
| 8052 | 35 | 0.10 ± 0.01 | 0.59 ± 0.04 | 5.70 ± 0.14 | 0.26 ± 0.02 | 9.68 ± 0.33 | 15.64 | 0.38 |
| 8052 | 30 | 0.13 ± 0.01 | 0.16 ± 0.05 | 6.31 ± 0.10 | 0.32 ± 0.03 | 9.96 ± 0.18 | 16.59 | 0.36 |
| 8052 | 25 | 0.39 ± 0.02 | 1.28 ± 0.13 | 3.33 ± 0.50 | 0.40 ± 0.03 | 9.71 ± 0.12 | 13.44 | 0.35 |
| 8052 | 20 | 0.22 ± 0.02 | 2.13 ± 0.13 | 3.75 ± 0.06 | 0.24 ± 0.01 | 11.12 ± 0.29 | 15.11 | 0.31 |
| N1-4 | 30 | 0.94 ± 0.14 | 1.88 ± 0.28 | 5.89 ± 0.12 | 1.02 ± 0.15 | 17.10 ± 0.25 | 24.01 | 0.35 |
| N1-4 | 25 | 1.23 ± 0.12 | 0.53 ± 0.05 | 4.21 ± 0.21 | 2.08 ± 0.04 | 18.07 ± 0.97 | 24.36 | 0.42 |
| N1-4 | 20 | 0.41 ± 0.04 | 0.85 ± 0.08 | 4.10 ± 0.60 | 0.71 ± 0.01 | 18.09 ± 0.78 | 22.58 | 0.41 |

[a]Values are based on at least two independent replicates.

What is claimed is:

1. A *Clostridium* strain modified for enhanced butanol production relative to wild type *C. tyrobutyricum* (ATCC 25755), said *Clostridium* strain comprising a modification to the native cat1 gene, said modification preventing expression of a functional cat1 gene product; and an exogenous sequence encoding i) an aldehyde dehydrogenase;

ii) a bifunctional aldehyde/alcohol dehydrogenase; or iii) an aldehyde dehydrogenase and an alcohol dehydrogenase.

2. The *Clostridium* strain of claim 1 wherein said *Clostridium* cat1 gene is modified by the insertion of said exogenous sequence into the cat1 gene rendering the cat1 gene incapable of expressing a functional gene product.

3. The *Clostridium* strain of claim 2 wherein said exogenous sequences comprises a bifunctional alcohol/aldehyde dehydrogenase gene selected from the group consisting of adhE1 and adhE2.

4. The *Clostridium* strain of claim 3 wherein said modified strain, when cultured at a temperature of less than 30° C. using glucose as a carbon source, produces at least 20 g/L of butanol after 72 hours of culture.

5. The strain of claim 1 wherein the strain is the *Clostridium tyrobutyricum* strain deposited with Agriculture Research Service Culture Collection (NRRL) and assigned accession no. NRRL B-67519.

6. A method of producing butanol, said method comprising the steps of culturing the *Clostridium* strain of claim 1 under conditions suitable for growth of the strain; and recovering the butanol produced by said cell.

7. The method of claim 6 wherein the strain is cultured at a temperature selected from the range of about 20° C. to about 30° C.

8. A *Clostridium* strain modified for enhanced butanol production relative to wild type *C. tyrobutyricum* (ATCC 25755), said *Clostridium* strain being selected from the group consisting of *Clostridium butyricum, Clostridium thermobutyricum, Clostridium cellulovorans, Clostridium carboxidivorans, Clostridium tyrobutyricum, Clostridium polysaccharolyticum, Clostridium populeti*, and *Clostridium kluyveri* and comprising a modification to the native cat1 gene, said modification preventing expression of a functional cat1 gene product; and an adhE gene introduced into said cell and having at least 95% sequence identity to a *C. acetobutylicum* aldehyde/alcohol dehydrogenase gene of SEQ ID NO: 133 or SEQ ID NO: 134.

9. The *Clostridium* strain of claim 8 wherein said *Clostridium* cat1 gene is modified by the insertion of said adhE gene into the cat1 gene rendering the cat1 gene incapable of expressing a functional gene product.

10. The *Clostridium* strain of claim 9 wherein said *Clostridium* strain is *Clostridium tyrobutyricum*.

11. The *Clostridium* strain of claim 9 wherein the entire coding region of said *Clostridium* cat1 gene is replaced with the inserted adhE gene.

* * * * *

SEQUENCE LISTING

<160> NUMBER OF SEQ ID NOS: 134

<210> SEQ ID NO 1
<211> LENGTH: 291
<212> TYPE: DNA
<213> ORGANISM: Clostridium tyrobutyricum

<400> SEQUENCE: 1
taagatcgta gcagataagg attttgtcac aatcataaaa cttataaatg atagttgctt 60
tgaggaggaa actttaggta taaatgataa aaatactgaa aacttgatac tttgaatttt 120
ccaacctgtt tgctatttag aatcacttca atttatttag aatcaatggg ttacgttatt 180
tcttataaaa tatatgcata ataaaaattg gttggaaaaa attcagcgaa aacctttatt 240
tatatgcttt caaagcttat aatgaaatta aagaatggct attttacaca g 291

<210> SEQ ID NO 2
<211> LENGTH: 30
<212> TYPE: DNA
<213> ORGANISM: Clostridium tyrobutyricum

<400> SEQUENCE: 2
gttgaacctt aacatgagat gtatttaaat 30

<210> SEQ ID NO 3
<211> LENGTH: 277
<212> TYPE: DNA
<213> ORGANISM: Clostridium tyrobutyricum

<400> SEQUENCE: 3
aatcaaacat tttaattaaa gagacaatta ttataaataa attggtatag aattatattg 60
aataaatcta taccaatttt taatttgata tcaagccttt gttaaaatat ctgttaaacc 120
caatttttct attctctttt ttatctcatt tttatctgta gtatatagtc ccttttcttt 180
cattctgtta aaatactctg cacctgcaaa agtgtatctg ttttttctac cctctgcagt 240
tttaattttg taattggcat agcttattat atctcca 277

<210> SEQ ID NO 4
<211> LENGTH: 666
<212> TYPE: DNA
<213> ORGANISM: Clostridium tyrobutyricum

<400> SEQUENCE: 4
taagatcgta gcagataagg attttgtcac aatcataaaa cttataaatg atagttgctt 60
tgaggaggaa actttaggta taaatgataa aaatactgaa aacttgatac tttgaatttt 120

```
ccaacctgtt tgctatttag aatcacttca atttatttag aatcaatggg ttacgttatt    180

tcttataaaa tatatgcata ataaaaattg gttggaaaaa attcagcgaa aacctttatt    240

tatatgcttt caaagcttat aatgaaatta aagaatggct attttacaca ggttgaacct    300

taacatgaga tgtatttaaa tataccgttt tcttgctctc actactatta gctatatcag    360

ttgaacctta acatgagatg tatttaaata atcaaacatt ttaattaaag agacaattat    420

tataaataaa ttggtataga attatattga ataaatctat accaattttt aatttgatat    480

caagcctttg ttaaaatatc tgttaaaccc aatttttcta ttctcttttt tatctcattt    540

ttatctgtag tatatagtcc cttttctttc attctgttaa aatactctgc acctgcaaaa    600

gtgtatctgt tttttctacc ctctgcagtt ttaattttgt aattggcata gcttattata    660

tctcca                                                               666


<210> SEQ ID NO 5
<211> LENGTH: 34
<212> TYPE: DNA
<213> ORGANISM: Clostridium tyrobutyricum

<400> SEQUENCE: 5

cttgtagaag atggatcaac cctacaactt ggta                                 34


<210> SEQ ID NO 6
<211> LENGTH: 20
<212> TYPE: DNA
<213> ORGANISM: Clostridium tyrobutyricum

<400> SEQUENCE: 6

gacatgctat tgaagtagcg                                                 20


<210> SEQ ID NO 7
<211> LENGTH: 20
<212> TYPE: DNA
<213> ORGANISM: Clostridium tyrobutyricum

<400> SEQUENCE: 7

taatttctac tcttgtagat                                                 20


<210> SEQ ID NO 8
<211> LENGTH: 23
<212> TYPE: DNA
<213> ORGANISM: Clostridium tyrobutyricum

<400> SEQUENCE: 8

ccgagagtaa tcgtgctttc agc                                             23


<210> SEQ ID NO 9
<211> LENGTH: 38
<212> TYPE: DNA
<213> ORGANISM: Clostridium tyrobutyricum

<400> SEQUENCE: 9

ataccgtttt cttgctctca ctactattag ctatatca                             38


<210> SEQ ID NO 10
<211> LENGTH: 38
<212> TYPE: DNA
<213> ORGANISM: Clostridium tyrobutyricum

<400> SEQUENCE: 10
```

-continued gcaaccatag ctataaattc tgaatttgtt ggtttacc 38

<210> SEQ ID NO 11
<211> LENGTH: 10
<212> TYPE: DNA
<213> ORGANISM: Clostridium tyrobutyricum

<400> SEQUENCE: 11
ataccgtttt 10

<210> SEQ ID NO 12
<211> LENGTH: 20
<212> TYPE: DNA
<213> ORGANISM: Clostridium tyrobutyricum

<400> SEQUENCE: 12
ataccgtttt cttgctctca 20

<210> SEQ ID NO 13
<211> LENGTH: 30
<212> TYPE: DNA
<213> ORGANISM: Clostridium tyrobutyricum

<400> SEQUENCE: 13
ataccgtttt cttgctctca ctactattag 30

<210> SEQ ID NO 14
<211> LENGTH: 50
<212> TYPE: DNA
<213> ORGANISM: Clostridium tyrobutyricum

<400> SEQUENCE: 14
ataccgtttt cttgctctca ctactattag ctatatcatt attaaacatt 50

<210> SEQ ID NO 15
<211> LENGTH: 30
<212> TYPE: DNA
<213> ORGANISM: Clostridium tyrobutyricum

<400> SEQUENCE: 15
ttggatgttc ttataaggac aaatactcct 30

<210> SEQ ID NO 16
<211> LENGTH: 34
<212> TYPE: DNA
<213> ORGANISM: Clostridium tyrobutyricum

<400> SEQUENCE: 16
gattgtgctg taaatcctgt acctaatact gaac 34

<210> SEQ ID NO 17
<211> LENGTH: 34
<212> TYPE: DNA
<213> ORGANISM: Clostridium tyrobutyricum

<400> SEQUENCE: 17
cttgtagaag atggatcaac cctacaactt ggta 34

<210> SEQ ID NO 18
<211> LENGTH: 30
<212> TYPE: DNA
<213> ORGANISM: Clostridium tyrobutyricum

<400> SEQUENCE: 18
attgaacctt aacatgagat gtatttaaat 30

<210> SEQ ID NO 19
<211> LENGTH: 36
<212> TYPE: DNA
<213> ORGANISM: Clostridium tyrobutyricum

<400> SEQUENCE: 19
tggtatcacc aacttttgtc caggatatat gaggtt 36

<210> SEQ ID NO 20
<211> LENGTH: 46
<212> TYPE: DNA
<213> ORGANISM: Clostridium tyrobutyricum

<400> SEQUENCE: 20
catctcggta tcaccaactt ctgcccggga tatatgagat taggat 46

<210> SEQ ID NO 21
<211> LENGTH: 51
<212> TYPE: DNA
<213> ORGANISM: Clostridium tyrobutyricum

<400> SEQUENCE: 21
catcatggta tcaccagctt ttggccggga taaatgagat tcggatcgga t 51

<210> SEQ ID NO 22
<211> LENGTH: 38
<212> TYPE: DNA
<213> ORGANISM: Clostridium tyrobutyricum

<400> SEQUENCE: 22
gcattcagac ttgcaactgt aactccctag tactcccc 38

<210> SEQ ID NO 23
<211> LENGTH: 124
<212> TYPE: DNA
<213> ORGANISM: Clostridium tyrobutyricum

<400> SEQUENCE: 23
gggttacgtt atttcttata aaatatatgc ataataaaaa ttggttggaa aaaattcagc 60
gaaaaccttt atttatatgc tttcaaagct tataatgaaa ttaaagaatg gctattttac 120
acag 124

<210> SEQ ID NO 24
<211> LENGTH: 127
<212> TYPE: DNA
<213> ORGANISM: Clostridium tyrobutyricum

<400> SEQUENCE: 24
ggcttatagg tgtttttcta ttaaaattta cgtaagacta aaaatagctg gtaaaatttt 60
tgctaaatcc tttattttta atgaatagag cattataatt atagtaaaga atggctagtt 120
ttaagta 127

<210> SEQ ID NO 25
<211> LENGTH: 30
<212> TYPE: DNA
<213> ORGANISM: Clostridium tyrobutyricum

<400> SEQUENCE: 25

-continued

```
gttgaacctt aacataggat gtatttaaat                                        30


<210> SEQ ID NO 26
<211> LENGTH: 47
<212> TYPE: DNA
<213> ORGANISM: Clostridium tyrobutyricum

<400> SEQUENCE: 26

acaattgaat ttaaaagaaa ccgataggcc ggccagtggg caagttg                     47


<210> SEQ ID NO 27
<211> LENGTH: 47
<212> TYPE: DNA
<213> ORGANISM: Clostridium tyrobutyricum

<400> SEQUENCE: 27

ctttagtaac gtgtaacttt ccaaatggag tttaaactta gggtaac                     47


<210> SEQ ID NO 28
<211> LENGTH: 83
<212> TYPE: DNA
<213> ORGANISM: Clostridium tyrobutyricum

<400> SEQUENCE: 28

aaaaaaagca ccgactcggt gccacttttt caagttgata acggactagc cttattttaa      60

cttgctattt ctagctctaa aac                                               83


<210> SEQ ID NO 29
<211> LENGTH: 80
<212> TYPE: DNA
<213> ORGANISM: Clostridium tyrobutyricum

<400> SEQUENCE: 29

agaaattaat acgactcact atagggatac taaaactgaa ttgattgttt tagagctaga      60

aatagcaagt taaaataagg                                                   80


<210> SEQ ID NO 30
<211> LENGTH: 80
<212> TYPE: DNA
<213> ORGANISM: Clostridium tyrobutyricum

<400> SEQUENCE: 30

agaaattaat acgactcact atagggagtg caaaaaaaga tataatgttt tagagctaga      60

aatagcaagt taaaataagg                                                   80


<210> SEQ ID NO 31
<211> LENGTH: 49
<212> TYPE: DNA
<213> ORGANISM: Clostridium tyrobutyricum

<400> SEQUENCE: 31

cgaacacgaa ccgtcttatc tcccattgtt ctgaatcctt agctaatgg                   49


<210> SEQ ID NO 32
<211> LENGTH: 50
<212> TYPE: DNA
<213> ORGANISM: Clostridium tyrobutyricum

<400> SEQUENCE: 32

taatgacccc gaagcagggg gcccaatgaa tttgtaaata aaccacaaac                  50
```

-continued

<210> SEQ ID NO 33
<211> LENGTH: 44
<212> TYPE: DNA
<213> ORGANISM: Clostridium tyrobutyricum

<400> SEQUENCE: 33
gtaatactaa aactgaattg attcctgctt cggggtcatt atag 44

<210> SEQ ID NO 34
<211> LENGTH: 55
<212> TYPE: DNA
<213> ORGANISM: Clostridium tyrobutyricum

<400> SEQUENCE: 34
atcaagtaaa taaaccaagt atataagggc ccgatcggtc ttgccttgct cgtcg 55

<210> SEQ ID NO 35
<211> LENGTH: 52
<212> TYPE: DNA
<213> ORGANISM: Clostridium tyrobutyricum

<400> SEQUENCE: 35
aaagttaaaa gaagaaaata gaaatataat ctttaatttg aaaagattta ag 52

<210> SEQ ID NO 36
<211> LENGTH: 60
<212> TYPE: DNA
<213> ORGANISM: Clostridium tyrobutyricum

<400> SEQUENCE: 36
ttgctatttc tagctctaaa accgctactt caatagcatg tcatggtgga atgataaggg 60

<210> SEQ ID NO 37
<211> LENGTH: 52
<212> TYPE: DNA
<213> ORGANISM: Clostridium tyrobutyricum

<400> SEQUENCE: 37
ctttgtgata tgactaataa ttagcggccg cctcagggtg tattagttgt ag 52

<210> SEQ ID NO 38
<211> LENGTH: 43
<212> TYPE: DNA
<213> ORGANISM: Clostridium tyrobutyricum

<400> SEQUENCE: 38
gttaaccatt gatatcactt taatatttta ctccccttttt att 43

<210> SEQ ID NO 39
<211> LENGTH: 43
<212> TYPE: DNA
<213> ORGANISM: Clostridium tyrobutyricum

<400> SEQUENCE: 39
aataaaaggg gagtaaaata ttaaagtgat atcaatggtt aac 43

<210> SEQ ID NO 40
<211> LENGTH: 52
<212> TYPE: DNA
<213> ORGANISM: Clostridium tyrobutyricum

<400> SEQUENCE: 40
atccactagt aaccatcaca ctggcggccg cgaccaatac tgaactatga cc 52

-continued

<210> SEQ ID NO 41
<211> LENGTH: 56
<212> TYPE: DNA
<213> ORGANISM: Clostridium tyrobutyricum

<400> SEQUENCE: 41
caccgacgag caaggcaaga ccgatcgggc ccttatatac ttggtttatt tacttg 56

<210> SEQ ID NO 42
<211> LENGTH: 44
<212> TYPE: DNA
<213> ORGANISM: Clostridium tyrobutyricum

<400> SEQUENCE: 42
cctattgagt atttcttatc catttcagcc ctcctgtgaa attg 44

<210> SEQ ID NO 43
<211> LENGTH: 44
<212> TYPE: DNA
<213> ORGANISM: Clostridium tyrobutyricum

<400> SEQUENCE: 43
caatttcaca ggagggctga aatggataag aaatactcaa tagg 44

<210> SEQ ID NO 44
<211> LENGTH: 26
<212> TYPE: DNA
<213> ORGANISM: Clostridium tyrobutyricum

<400> SEQUENCE: 44
gataaattta taaaattctt cttggc 26

<210> SEQ ID NO 45
<211> LENGTH: 60
<212> TYPE: DNA
<213> ORGANISM: Clostridium tyrobutyricum

<400> SEQUENCE: 45
ggaaacagct atgaccgcgg ccgctgtatc ttatatactt ggtttattta cttgattatt 60

<210> SEQ ID NO 46
<211> LENGTH: 70
<212> TYPE: DNA
<213> ORGANISM: Clostridium tyrobutyricum

<400> SEQUENCE: 46
tggtagagat tggtgaagcc ttcaaactgt gtcatttcag ccctcctgtg aaattgttat 60
ccgctcacaa 70

<210> SEQ ID NO 47
<211> LENGTH: 70
<212> TYPE: DNA
<213> ORGANISM: Clostridium tyrobutyricum

<400> SEQUENCE: 47
ttgtgagcgg ataacaattt cacaggaggg ctgaaatgac acagtttgaa ggcttcacca 60
atctctacca 70

<210> SEQ ID NO 48
<211> LENGTH: 60
<212> TYPE: DNA
<213> ORGANISM: Clostridium tyrobutyricum

<400> SEQUENCE: 48
gggtaccgag ctcgaattcg taatcatggt ttagtttctc agttcttgaa tgtaggccag 60

<210> SEQ ID NO 49
<211> LENGTH: 55
<212> TYPE: DNA
<213> ORGANISM: Clostridium tyrobutyricum

<400> SEQUENCE: 49
gattacgaat tcgagctcgg tacccgggat aatctttaat ttgaaaagat ttaag 55

<210> SEQ ID NO 50
<211> LENGTH: 53
<212> TYPE: DNA
<213> ORGANISM: Clostridium tyrobutyricum

<400> SEQUENCE: 50
ttagctgaaa gcacgattac tctcggatct acaagagtag aaattaatgg tgg 53

<210> SEQ ID NO 51
<211> LENGTH: 67
<212> TYPE: DNA
<213> ORGANISM: Clostridium tyrobutyricum

<400> SEQUENCE: 51
gatccgagag taatcgtgct ttcagctaat ttctactctt gtagatctca gggtgtatta 60
gttgtag 67

<210> SEQ ID NO 52
<211> LENGTH: 49
<212> TYPE: DNA
<213> ORGANISM: Clostridium tyrobutyricum

<400> SEQUENCE: 52
ccatggacgc gtgacgtcga ctctagagga ccaatactga actatgacc 49

<210> SEQ ID NO 53
<211> LENGTH: 47
<212> TYPE: DNA
<213> ORGANISM: Clostridium tyrobutyricum

<400> SEQUENCE: 53
ctgtatccat atgaccatga ttacgtaaga tcgtagcaga taaggat 47

<210> SEQ ID NO 54
<211> LENGTH: 80
<212> TYPE: DNA
<213> ORGANISM: Clostridium tyrobutyricum

<400> SEQUENCE: 54
gctaatagta gtgagagcaa gaaaacggta tatttaaata catctcatgt taaggttcaa 60
cctgtgtaaa atagccattc 80

<210> SEQ ID NO 55
<211> LENGTH: 80
<212> TYPE: DNA
<213> ORGANISM: Clostridium tyrobutyricum

<400> SEQUENCE: 55
tttcttgctc tcactactat tagctatatc agttgaacct taacatgaga tgtatttaaa 60
tcccatagaa gctctatact 80

<210> SEQ ID NO 56
<211> LENGTH: 49
<212> TYPE: DNA
<213> ORGANISM: Clostridium tyrobutyricum

<400> SEQUENCE: 56
ctacaactaa tacaccctga gggtacctgg agatataata agctatgcc 49

<210> SEQ ID NO 57
<211> LENGTH: 48
<212> TYPE: DNA
<213> ORGANISM: Clostridium tyrobutyricum

<400> SEQUENCE: 57
catgattacg aattcgagct cggtaccctc agggtgtatt agttgtag 48

<210> SEQ ID NO 58
<211> LENGTH: 43
<212> TYPE: DNA
<213> ORGANISM: Clostridium tyrobutyricum

<400> SEQUENCE: 58
gttaaccatt gatatcactt taatatttta ctccccttt att 43

<210> SEQ ID NO 59
<211> LENGTH: 43
<212> TYPE: DNA
<213> ORGANISM: Clostridium tyrobutyricum

<400> SEQUENCE: 59
aataaaaggg gagtaaaata ttaaagtgat atcaatggtt aac 43

<210> SEQ ID NO 60
<211> LENGTH: 46
<212> TYPE: DNA
<213> ORGANISM: Clostridium tyrobutyricum

<400> SEQUENCE: 60
tggacgcgtg acgtcgactc tagaggacca atactgaact atgacc 46

<210> SEQ ID NO 61
<211> LENGTH: 47
<212> TYPE: DNA
<213> ORGANISM: Clostridium tyrobutyricum

<400> SEQUENCE: 61
ctgtatccat atgaccatga ttacggattg ggcccttata tacttgg 47

<210> SEQ ID NO 62
<211> LENGTH: 66
<212> TYPE: DNA
<213> ORGANISM: Clostridium tyrobutyricum

<400> SEQUENCE: 62
gcaagaaaac ggtatattta aatacatctc atgttaaggt tcaacttcag ccctcctgtg 60
aaattg 66

<210> SEQ ID NO 63
<211> LENGTH: 39
<212> TYPE: DNA
<213> ORGANISM: Clostridium tyrobutyricum

<400> SEQUENCE: 63
catgagatgt atttaaatat accgttttct tgctctcac 39

<210> SEQ ID NO 64
<211> LENGTH: 49
<212> TYPE: DNA
<213> ORGANISM: Clostridium tyrobutyricum

<400> SEQUENCE: 64
ctacaactaa tacaccctga gggtacctgg agatataata agctatgcc 49

<210> SEQ ID NO 65
<211> LENGTH: 83
<212> TYPE: DNA
<213> ORGANISM: Clostridium tyrobutyricum

<400> SEQUENCE: 65
ccaacaaatt cagaatttat agctatggtt gcatttaaat acatctcatg ttaaggttca 60
acttcagccc tcctgtgaaa ttg 83

<210> SEQ ID NO 66
<211> LENGTH: 81
<212> TYPE: DNA
<213> ORGANISM: Clostridium tyrobutyricum

<400> SEQUENCE: 66
atagctataa attctgaatt tgttggttta ccgttgaacc ttaacatgag atgtatttaa 60
atcccataga agctctatac t 81

<210> SEQ ID NO 67
<211> LENGTH: 47
<212> TYPE: DNA
<213> ORGANISM: Clostridium tyrobutyricum

<400> SEQUENCE: 67
ctgtatccat atgaccatga ttacgttatg aaagcgatta cctatat 47

<210> SEQ ID NO 68
<211> LENGTH: 69
<212> TYPE: DNA
<213> ORGANISM: Clostridium tyrobutyricum

<400> SEQUENCE: 68
gcaagaaaac ggtatattta aatacatctc atgttaaggt tcaacaatat tcctcctaaa 60
tttataatc 69

<210> SEQ ID NO 69
<211> LENGTH: 69
<212> TYPE: DNA
<213> ORGANISM: Clostridium tyrobutyricum

<400> SEQUENCE: 69
ggttcaacaa aacggtatat ttaaatacat ctcatgttaa ggttcaactt cagccctcct 60
gtgaaattg 69

<210> SEQ ID NO 70
<211> LENGTH: 67
<212> TYPE: DNA
<213> ORGANISM: Clostridium tyrobutyricum

<400> SEQUENCE: 70
atttaaatat accgttttgt tgaaccttaa catgagatgt atttaaatcc catagaagct 60
ctatact 67

<210> SEQ ID NO 71
<211> LENGTH: 75
<212> TYPE: DNA
<213> ORGANISM: Clostridium tyrobutyricum

<400> SEQUENCE: 71
caactgagag caagaaaacg gtatatttaa atacatctca tgttaaggtt caacttcagc 60
cctcctgtga aattg 75

<210> SEQ ID NO 72
<211> LENGTH: 73
<212> TYPE: DNA
<213> ORGANISM: Clostridium tyrobutyricum

<400> SEQUENCE: 72
aaatataccg ttttcttgct ctcagttgaa ccttaacatg agatgtattt aaatcccata 60
gaagctctat act 73

<210> SEQ ID NO 73
<211> LENGTH: 81
<212> TYPE: DNA
<213> ORGANISM: Clostridium tyrobutyricum

<400> SEQUENCE: 73
ctaatagtag tgagagcaag aaaacggtat atttaaatac atctcatgtt aaggttcaac 60
ttcagccctc ctgtgaaatt g 81

<210> SEQ ID NO 74
<211> LENGTH: 79
<212> TYPE: DNA
<213> ORGANISM: Clostridium tyrobutyricum

<400> SEQUENCE: 74
ataccgtttt cttgctctca ctactattag gttgaacctt aacatgagat gtatttaaat 60
cccatagaag ctctatact 79

<210> SEQ ID NO 75
<211> LENGTH: 88
<212> TYPE: DNA
<213> ORGANISM: Clostridium tyrobutyricum

<400> SEQUENCE: 75
gatatagcta atagtagtga gagcaagaaa acggtatatt taaatacatc tcatgttaag 60
gttcaacttc agccctcctg tgaaattg 88

<210> SEQ ID NO 76
<211> LENGTH: 88
<212> TYPE: DNA
<213> ORGANISM: Clostridium tyrobutyricum

<400> SEQUENCE: 76
ttgctctcac tactattagc tatatcatta ttaaacattg ttgaacctta acatgagatg 60
tatttaaatc ccatagaagc tctatact 88

<210> SEQ ID NO 77
<211> LENGTH: 50
<212> TYPE: DNA
<213> ORGANISM: Clostridium tyrobutyricum

<400> SEQUENCE: 77
catgattacg aattcgagct cggtaccgtt caaggtatga gtggaagtcc 50

<210> SEQ ID NO 78
<211> LENGTH: 55
<212> TYPE: DNA
<213> ORGANISM: Clostridium tyrobutyricum

<400> SEQUENCE: 78
tggacgcgtg acgtcgactc tagagacatc ttctatatat ctgcaaaata gcttc 55

<210> SEQ ID NO 79
<211> LENGTH: 50
<212> TYPE: DNA
<213> ORGANISM: Clostridium tyrobutyricum

<400> SEQUENCE: 79
cctgactcta gagtcgacgt cacgcgtcga ttgggccctt atatacttgg 50

<210> SEQ ID NO 80
<211> LENGTH: 81
<212> TYPE: DNA
<213> ORGANISM: Clostridium tyrobutyricum

<400> SEQUENCE: 80
aggagtattt gtccttataa gaacatccaa atttaaatac atctcatgtt aaggttcaac 60
ttcagccctc ctgtgaaatt g 81

<210> SEQ ID NO 81
<211> LENGTH: 79
<212> TYPE: DNA
<213> ORGANISM: Clostridium tyrobutyricum

<400> SEQUENCE: 81
ttggatgttc ttataaggac aaatactcct gttgaacctt aacatgagat gtatttaaat 60
cccatagaag ctctatact 79

<210> SEQ ID NO 82
<211> LENGTH: 50
<212> TYPE: DNA
<213> ORGANISM: Clostridium tyrobutyricum

<400> SEQUENCE: 82
cgacgttgta aaacgacggc cagtgccatg gagatataat aagctatgcc 50

<210> SEQ ID NO 83
<211> LENGTH: 48
<212> TYPE: DNA
<213> ORGANISM: Clostridium tyrobutyricum

<400> SEQUENCE: 83
ctgtatccat atgaccatga ttacggctat attgggtttc atagatcc 48

<210> SEQ ID NO 84
<211> LENGTH: 44
<212> TYPE: DNA
<213> ORGANISM: Clostridium tyrobutyricum -continued

<400> SEQUENCE: 84
gcacactctg catagtctgt gtaagtatcc aggcctacac atac 44

<210> SEQ ID NO 85
<211> LENGTH: 44
<212> TYPE: DNA
<213> ORGANISM: Clostridium tyrobutyricum

<400> SEQUENCE: 85
gtatgtgtag gcctggatac ttacacagac tatgcagagt gtgc 44

<210> SEQ ID NO 86
<211> LENGTH: 47
<212> TYPE: DNA
<213> ORGANISM: Clostridium tyrobutyricum

<400> SEQUENCE: 86
tggacgcgtg acgtcgactc tagagtagtt ccatttccaa ctacctg 47

<210> SEQ ID NO 87
<211> LENGTH: 53
<212> TYPE: DNA
<213> ORGANISM: Clostridium tyrobutyricum

<400> SEQUENCE: 87
ctgtatccat atgaccatga ttacgcccgg ggattgggcc cttatatact tgg 53

<210> SEQ ID NO 88
<211> LENGTH: 80
<212> TYPE: DNA
<213> ORGANISM: Clostridium tyrobutyricum

<400> SEQUENCE: 88
ggagtatttg tccttataag aacatccaaa tttaaataca tctcatgtta aggttcaact 60
tcagccctcc tgtgaaattg 80

<210> SEQ ID NO 89
<211> LENGTH: 79
<212> TYPE: DNA
<213> ORGANISM: Clostridium tyrobutyricum

<400> SEQUENCE: 89
ggatgttctt ataaggacaa atactcctgt tgaaccttaa catgagatgt atttaaatat 60
accgttttct tgctctcac 79

<210> SEQ ID NO 90
<211> LENGTH: 49
<212> TYPE: DNA
<213> ORGANISM: Clostridium tyrobutyricum

<400> SEQUENCE: 90
ctacaactaa tacaccctga gggtacctgg agatataata agctatgcc 49

<210> SEQ ID NO 91
<211> LENGTH: 50
<212> TYPE: DNA
<213> ORGANISM: Clostridium tyrobutyricum

<400> SEQUENCE: 91
catgattacg aattcgagct cggtaccgct atattgggtt tcatagatcc 50

-continued

<210> SEQ ID NO 92
<211> LENGTH: 45
<212> TYPE: DNA
<213> ORGANISM: Clostridium tyrobutyricum

<400> SEQUENCE: 92
ggacttccac tcataccttg aactagttcc atttccaact acctg 45

<210> SEQ ID NO 93
<211> LENGTH: 45
<212> TYPE: DNA
<213> ORGANISM: Clostridium tyrobutyricum

<400> SEQUENCE: 93
caggtagttg gaaatggaac tagttcaagg tatgagtgga agtcc 45

<210> SEQ ID NO 94
<211> LENGTH: 55
<212> TYPE: DNA
<213> ORGANISM: Clostridium tyrobutyricum

<400> SEQUENCE: 94
tggacgcgtg acgtcgactc tagagacatc ttctatatat ctgcaaaata gcttc 55

<210> SEQ ID NO 95
<211> LENGTH: 47
<212> TYPE: DNA
<213> ORGANISM: Clostridium tyrobutyricum

<400> SEQUENCE: 95
ctgtatccat atgaccatga ttacggattg ggcccttata tacttgg 47

<210> SEQ ID NO 96
<211> LENGTH: 81
<212> TYPE: DNA
<213> ORGANISM: Clostridium tyrobutyricum

<400> SEQUENCE: 96
agtattaggt acaggattta cagcacaatc atttaaatac atctcatgtt aaggttcaac 60
ttcagccctc ctgtgaaatt g 81

<210> SEQ ID NO 97
<211> LENGTH: 79
<212> TYPE: DNA
<213> ORGANISM: Clostridium tyrobutyricum

<400> SEQUENCE: 97
gtgctgtaaa tcctgtacct aatactgaac gttgaacctt aacatgagat gtatttaaat 60
cccatagaag ctctatact 79

<210> SEQ ID NO 98
<211> LENGTH: 49
<212> TYPE: DNA
<213> ORGANISM: Clostridium tyrobutyricum

<400> SEQUENCE: 98
gtcgactcta gaggatcccc gggtacctgg agatataata agctatgcc 49

<210> SEQ ID NO 99
<211> LENGTH: 51
<212> TYPE: DNA
<213> ORGANISM: Clostridium tyrobutyricum -continued

<400> SEQUENCE: 99
ggcatagctt attatatctc caggtacgta tcaactacgc ctaaattctc c 51

<210> SEQ ID NO 100
<211> LENGTH: 48
<212> TYPE: DNA
<213> ORGANISM: Clostridium tyrobutyricum

<400> SEQUENCE: 100
taggctgttc agggatcccc gggtaccttt cgtttctccc ttcaagat 48

<210> SEQ ID NO 101
<211> LENGTH: 48
<212> TYPE: DNA
<213> ORGANISM: Clostridium tyrobutyricum

<400> SEQUENCE: 101
ggagaaacga aaggtacccg gggatccctg aacagcctat ggaagacc 48

<210> SEQ ID NO 102
<211> LENGTH: 46
<212> TYPE: DNA
<213> ORGANISM: Clostridium tyrobutyricum

<400> SEQUENCE: 102
tggacgcgtg acgtcgactc tagagcaccg tcaattgcac atacac 46

<210> SEQ ID NO 103
<211> LENGTH: 49
<212> TYPE: DNA
<213> ORGANISM: Clostridium tyrobutyricum

<400> SEQUENCE: 103
tatcttgaag ggagaaacga aaggtacatg aaagtcacaa cagtaaagg 49

<210> SEQ ID NO 104
<211> LENGTH: 51
<212> TYPE: DNA
<213> ORGANISM: Clostridium tyrobutyricum

<400> SEQUENCE: 104
ttatggtctt ccataggctg ttcagggttg aaatatgaag gtttaaggtt g 51

<210> SEQ ID NO 105
<211> LENGTH: 49
<212> TYPE: DNA
<213> ORGANISM: Clostridium tyrobutyricum

<400> SEQUENCE: 105
tatcttgaag ggagaaacga aaggtacatg aaagttacaa atcaaaaag 49

<210> SEQ ID NO 106
<211> LENGTH: 51
<212> TYPE: DNA
<213> ORGANISM: Clostridium tyrobutyricum

<400> SEQUENCE: 106
ttatggtctt ccataggctg ttcaggttaa aatgatttta tatagatatc c 51

<210> SEQ ID NO 107
<211> LENGTH: 47
<212> TYPE: DNA
<213> ORGANISM: Clostridium tyrobutyricum

<400> SEQUENCE: 107
ctgtatccat atgaccatga ttacggattg ggcccttata tacttgg 47

<210> SEQ ID NO 108
<211> LENGTH: 80
<212> TYPE: DNA
<213> ORGANISM: Clostridium tyrobutyricum

<400> SEQUENCE: 108
agttgtaggg ttgatccatc ttctacaaga tttaaataca tctcatgtta aggttcaact 60
tcagccctcc tgtgaaattg 80

<210> SEQ ID NO 109
<211> LENGTH: 80
<212> TYPE: DNA
<213> ORGANISM: Clostridium tyrobutyricum

<400> SEQUENCE: 109
gtagaagatg gatcaaccct acaacttggt agttgaacct taacatgaga tgtatttaaa 60
tcccatagaa gctctatact 80

<210> SEQ ID NO 110
<211> LENGTH: 49
<212> TYPE: DNA
<213> ORGANISM: Clostridium tyrobutyricum

<400> SEQUENCE: 110
gtcgactcta gaggatcccc gggtacctgg agatataata agctatgcc 49

<210> SEQ ID NO 111
<211> LENGTH: 48
<212> TYPE: DNA
<213> ORGANISM: Clostridium tyrobutyricum

<400> SEQUENCE: 111
ggcatagctt attatatctc caggtacacc catgctgcaa agcaagtt 48

<210> SEQ ID NO 112
<211> LENGTH: 49
<212> TYPE: DNA
<213> ORGANISM: Clostridium tyrobutyricum

<400> SEQUENCE: 112
tgagaaagct aaggatcccc gggtaccaaa aaccaccctt tcataaatt 49

<210> SEQ ID NO 113
<211> LENGTH: 49
<212> TYPE: DNA
<213> ORGANISM: Clostridium tyrobutyricum

<400> SEQUENCE: 113
gggtggtttt tggtacccgg ggatccttag ctttctcaaa agatatttt 49

<210> SEQ ID NO 114
<211> LENGTH: 46
<212> TYPE: DNA
<213> ORGANISM: Clostridium tyrobutyricum

<400> SEQUENCE: 114
tggacgcgtg acgtcgactc tagagccata tgcggtggtt atcaac 46

-continued

<210> SEQ ID NO 115
<211> LENGTH: 49
<212> TYPE: DNA
<213> ORGANISM: Clostridium tyrobutyricum

<400> SEQUENCE: 115
aatttatgaa agggtggttt ttggtacatg aaagtcacaa cagtaaagg 49

<210> SEQ ID NO 116
<211> LENGTH: 52
<212> TYPE: DNA
<213> ORGANISM: Clostridium tyrobutyricum

<400> SEQUENCE: 116
ttaaaaatat cttttgagaa agctaaggtt gaaatatgaa ggtttaaggt tg 52

<210> SEQ ID NO 117
<211> LENGTH: 49
<212> TYPE: DNA
<213> ORGANISM: Clostridium tyrobutyricum

<400> SEQUENCE: 117
aatttatgaa agggtggttt ttggtacatg aaagttacaa atcaaaaag 49

<210> SEQ ID NO 118
<211> LENGTH: 52
<212> TYPE: DNA
<213> ORGANISM: Clostridium tyrobutyricum

<400> SEQUENCE: 118
ttaaaaatat cttttgagaa agctaagtta aaatgatttt atatagatat cc 52

<210> SEQ ID NO 119
<211> LENGTH: 46
<212> TYPE: DNA
<213> ORGANISM: Clostridium tyrobutyricum

<400> SEQUENCE: 119
ctgtatccat atgaccatga ttacggtaga ctttaaggat ggaacc 46

<210> SEQ ID NO 120
<211> LENGTH: 80
<212> TYPE: DNA
<213> ORGANISM: Clostridium tyrobutyricum

<400> SEQUENCE: 120
tcgactctag aggatccccg ggtaccgaat tctgtcgact gcgatgagct aggtcagtaa 60
aaaccaccct ttcataaatt 80

<210> SEQ ID NO 121
<211> LENGTH: 48
<212> TYPE: DNA
<213> ORGANISM: Clostridium tyrobutyricum

<400> SEQUENCE: 121
atataattta tgaaagggtg gtttttatga aagtcacaac agtaaagg 48

<210> SEQ ID NO 122
<211> LENGTH: 56
<212> TYPE: DNA
<213> ORGANISM: Clostridium tyrobutyricum

<400> SEQUENCE: 122
cgactctaga ggatccccgg gtaccgaatt cgttgaaata tgaaggttta aggttg 56

<210> SEQ ID NO 123
<211> LENGTH: 48
<212> TYPE: DNA
<213> ORGANISM: Clostridium tyrobutyricum

<400> SEQUENCE: 123
atataattta tgaaagggtg gtttttatga aagttacaaa tcaaaaag 48

<210> SEQ ID NO 124
<211> LENGTH: 57
<212> TYPE: DNA
<213> ORGANISM: Clostridium tyrobutyricum

<400> SEQUENCE: 124
cgactctaga ggatccccgg gtaccggtaa ccttaaaatg attttatata gatatcc 57

<210> SEQ ID NO 125
<211> LENGTH: 21
<212> TYPE: DNA
<213> ORGANISM: Clostridium tyrobutyricum

<400> SEQUENCE: 125
tgttcctgta ggatcagtat c 21

<210> SEQ ID NO 126
<211> LENGTH: 21
<212> TYPE: DNA
<213> ORGANISM: Clostridium tyrobutyricum

<400> SEQUENCE: 126
ggactgtacc tctggtagtt c 21

<210> SEQ ID NO 127
<211> LENGTH: 23
<212> TYPE: DNA
<213> ORGANISM: Clostridium tyrobutyricum

<400> SEQUENCE: 127
gttgaaagac agctatatct tgg 23

<210> SEQ ID NO 128
<211> LENGTH: 21
<212> TYPE: DNA
<213> ORGANISM: Clostridium tyrobutyricum

<400> SEQUENCE: 128
atgccatgtg attctccata g 21

<210> SEQ ID NO 129
<211> LENGTH: 23
<212> TYPE: DNA
<213> ORGANISM: Clostridium tyrobutyricum

<400> SEQUENCE: 129
tctatacctt cagatacttc tgg 23

<210> SEQ ID NO 130
<211> LENGTH: 22
<212> TYPE: DNA
<213> ORGANISM: Clostridium tyrobutyricum

<400> SEQUENCE: 130
ctcacctcta tacattagcc ac 22

<210> SEQ ID NO 131
<211> LENGTH: 23
<212> TYPE: DNA
<213> ORGANISM: Clostridium tyrobutyricum

<400> SEQUENCE: 131
gccattaagt acaaatgaga tag 23

<210> SEQ ID NO 132
<211> LENGTH: 23
<212> TYPE: DNA
<213> ORGANISM: Clostridium tyrobutyricum

<400> SEQUENCE: 132
gccattaagt acaaatgaga tag 23

<210> SEQ ID NO 133
<211> LENGTH: 862
<212> TYPE: PRT
<213> ORGANISM: Clostridium acetobutylicum

<400> SEQUENCE: 133

```
Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220

Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
                245                 250                 255
```

-continued

```
Tyr Asn Lys Val Lys Asp Glu Phe Gln Glu Arg Gly Ala Tyr Ile Ile
            260                 265                 270

Lys Lys Asn Glu Leu Asp Lys Val Arg Glu Val Ile Phe Lys Asp Gly
        275                 280                 285

Ser Val Asn Pro Lys Ile Val Gly Gln Ser Ala Tyr Thr Ile Ala Ala
    290                 295                 300

Met Ala Gly Ile Lys Val Pro Lys Thr Thr Arg Ile Leu Ile Gly Glu
305                 310                 315                 320

Val Thr Ser Leu Gly Glu Glu Glu Pro Phe Ala His Glu Lys Leu Ser
                325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Gly Leu Gly His Thr Ser Gly
        355                 360                 365

Ile Tyr Ala Asp Glu Ile Lys Ala Arg Asp Lys Ile Asp Arg Phe Ser
    370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
            420                 425                 430

Pro Lys His Leu Leu Asn Ile Lys Thr Val Ala Glu Arg Arg Glu Asn
        435                 440                 445

Met Leu Trp Phe Arg Val Pro His Lys Val Tyr Phe Lys Phe Gly Cys
    450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
            500                 505                 510

Lys Val Gly Arg Glu Ala Asp Leu Lys Thr Ile Lys Lys Ala Thr Glu
        515                 520                 525

Glu Met Ser Ser Phe Met Pro Asp Thr Ile Ile Ala Leu Gly Gly Thr
    530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
            580                 585                 590

Ile Thr Thr Ser Ala Gly Ser Gly Ser Glu Val Thr Pro Phe Ala Leu
        595                 600                 605

Val Thr Asp Asn Asn Thr Gly Asn Lys Tyr Met Leu Ala Asp Tyr Glu
    610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

Ile Glu Ala Tyr Thr Ser Val Tyr Ala Ser Glu Tyr Thr Asn Gly Leu
            660                 665                 670
```

-continued

Ala Leu Glu Ala Ile Arg Leu Ile Phe Lys Tyr Leu Pro Glu Ala Tyr
675 680 685

Lys Asn Gly Arg Thr Asn Glu Lys Ala Arg Glu Lys Met Ala His Ala
690 695 700

Ser Thr Met Ala Gly Met Ala Ser Ala Asn Ala Phe Leu Gly Leu Cys
705 710 715 720

His Ser Met Ala Ile Lys Leu Ser Ser Glu His Asn Ile Pro Ser Gly
725 730 735

Ile Ala Asn Ala Leu Leu Ile Glu Glu Val Ile Lys Phe Asn Ala Val
740 745 750

Asp Asn Pro Val Lys Gln Ala Pro Cys Pro Gln Tyr Lys Tyr Pro Asn
755 760 765

Thr Ile Phe Arg Tyr Ala Arg Ile Ala Asp Tyr Ile Lys Leu Gly Gly
770 775 780

Asn Thr Asp Glu Glu Lys Val Asp Leu Leu Ile Asn Lys Ile His Glu
785 790 795 800

Leu Lys Lys Ala Leu Asn Ile Pro Thr Ser Ile Lys Asp Ala Gly Val
805 810 815

Leu Glu Glu Asn Phe Tyr Ser Ser Leu Asp Arg Ile Ser Glu Leu Ala
820 825 830

Leu Asp Asp Gln Cys Thr Gly Ala Asn Pro Arg Phe Pro Leu Thr Ser
835 840 845

Glu Ile Lys Glu Met Tyr Ile Asn Cys Phe Lys Lys Gln Pro
850 855 860

<210> SEQ ID NO 134
<211> LENGTH: 858
<212> TYPE: PRT
<213> ORGANISM: Clostridium acetobutylicum

<400> SEQUENCE: 134

Met Lys Val Thr Asn Gln Lys Glu Leu Lys Gln Lys Leu Asn Glu Leu
1 5 10 15

Arg Glu Ala Gln Lys Lys Phe Ala Thr Tyr Thr Gln Glu Gln Val Asp
20 25 30

Lys Ile Phe Lys Gln Cys Ala Ile Ala Ala Ala Lys Glu Arg Ile Asn
35 40 45

Leu Ala Lys Leu Ala Val Glu Glu Thr Gly Ile Gly Leu Val Glu Asp
50 55 60

Lys Ile Ile Lys Asn His Phe Ala Ala Glu Tyr Ile Tyr Asn Lys Tyr
65 70 75 80

Lys Asn Glu Lys Thr Cys Gly Ile Ile Asp His Asp Asp Ser Leu Gly
85 90 95

Ile Thr Lys Val Ala Glu Pro Ile Gly Ile Val Ala Ala Ile Val Pro
100 105 110

Thr Thr Asn Pro Thr Ser Thr Ala Ile Phe Lys Ser Leu Ile Ser Leu
115 120 125

Lys Thr Arg Asn Ala Ile Phe Phe Ser Pro His Pro Arg Ala Lys Lys
130 135 140

Ser Thr Ile Ala Ala Ala Lys Leu Ile Leu Asp Ala Ala Val Lys Ala
145 150 155 160

Gly Ala Pro Lys Asn Ile Ile Gly Trp Ile Asp Glu Pro Ser Ile Glu
165 170 175

Leu Ser Gln Asp Leu Met Ser Glu Ala Asp Ile Ile Leu Ala Thr Gly
180 185 190

-continued

```
Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605
```

-continued

```
Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855
```